United States Patent
Weiss et al.

(10) Patent No.: US 11,795,455 B2
(45) Date of Patent: Oct. 24, 2023

(54) RNA CLEAVAGE-INDUCED TRANSCRIPT STABILIZER AND USES THEREOF

(71) Applicant: Massachusetts Institute of Technology, Cambridge, MA (US)

(72) Inventors: Ron Weiss, Newton, MA (US); Breanna E. DiAndreth, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1270 days.

(21) Appl. No.: 16/049,042

(22) Filed: Jul. 30, 2018

(65) Prior Publication Data

US 2019/0032054 A1 Jan. 31, 2019

Related U.S. Application Data

(60) Provisional application No. 62/539,375, filed on Jul. 31, 2017.

(51) Int. Cl.
*C12N 15/113* (2010.01)
*A61K 48/00* (2006.01)
*C12N 15/63* (2006.01)
*C12N 15/67* (2006.01)

(52) U.S. Cl.
CPC ........ *C12N 15/113* (2013.01); *A61K 48/0066* (2013.01); *C12N 15/63* (2013.01); *C12N 15/67* (2013.01); *C12N 2310/121* (2013.01); *C12N 2310/122* (2013.01); *C12N 2310/126* (2013.01); *C12N 2310/14* (2013.01); *C12N 2840/105* (2013.01)

(58) Field of Classification Search
CPC .................................................... C12N 15/113
See application file for complete search history.

(56) References Cited

FOREIGN PATENT DOCUMENTS

WO  WO 2012/056440 A1  5/2012

OTHER PUBLICATIONS

Borchardt et al., Controlling mRNA stability and translation with the CRISPR endoribonuclease Csy4. RNA. Nov. 2015;21(11):1921-30. doi: 10.1261/rna.051227.115. Epub Sep. 9, 2015.
Kandul et al., A positive readout single transcript reporter for site-specific mRNA cleavage. PeerJ. Jul. 20, 2017;5:e3602. doi: 10.7717/peerj.3602.
Brown et al., Structural insights into the stabilization of MALAT1 noncoding RNA by a bipartite triple helix. Nat Struct Mol Biol. Jul. 2014;21(7):633-40. doi: 10.1038/nsmb.2844. Epub Jun. 22, 2014. PMID: 24952594; PMCID: PMC4096706.
Carbonell et al., Trans-cleaving hammerhead ribozymes with tertiary stabilizing motifs: in vitro and in vivo activity against a structured viroid RNA. Nucleic Acids Res. Mar. 2011;39(6):2432-44. doi: 10.1093/nar/gkq1051. Epub Nov. 21, 2010. PMID: 21097888; PMCID: PMC3064770.
Carte et al., Cas6 is an endoribonuclease that generates guide RNAs for invader defense in prokaryotes. Genes Dev. Dec. 15, 2008;22(24):3489-96. doi: 10.1101/gad.1742908. PMID: 19141480; PMCID: PMC2607076.
Choudhury et al., Engineering RNA endonucleases with customized sequence specificities. Nat Commun. 2012;3:1147. doi: 10.1038/ncomms2154. PMID: 23093184; PMCID: PMC3612931.
Cooke et al., Translational repression by deadenylases. J Biol Chem. Sep. 10, 2010;285(37):28506-13. doi: 10.1074/jbc.M110.150763. Epub Jul. 15, 2010. PMID: 20634287; PMCID: PMC2937876.
Geissler et al., A widespread sequence-specific mRNA decay pathway mediated by hnRNPs A1 and A2/B1. Genes Dev. May 1, 2016;30(9):1070-85. doi: 10.1101/gad.277392.116. PMID: 27151978; PMCID: PMC4863738.
Matoulkova et al., The role of the 3' untranslated region in post-transcriptional regulation of protein expression in mammalian cells. RNA Biol. May 2012;9(5):563-76. doi: 10.4161/rna.20231. Epub May 1, 2012. PMID: 22614827.
Saito et al. Synthetic translational regulation by an L 7 Ae-kink-turn RNP switch. Nat. Chem. Biol. 6, 71-78 (2010).
Scott et al., The hammerhead ribozyme: structure, catalysis, and gene regulation. Prog Mol Biol Transl Sci. 2013;120:1-23. doi: 10.1016/B978-0-12-381286-5.00001-9. PMID: 24156940; PMCID: PMC4008931.
Weston et al., Xp54 and related (DDX6-like) RNA helicases: roles in messenger RNP assembly, translation regulation and RNA degradation. Nucleic Acids Res. Jun. 12, 2006;34(10):3082-94. doi: 10.1093/nar/gkl409. PMID: 16769775; PMCID: PMC1477856.
Wilusz et al., A triple helix stabilizes the 3' ends of long noncoding RNAs that lack poly(A) tails. Genes Dev. Nov. 1, 2012;26(21):2392-407. doi: 10.1101/gad.204438.112. Epub Oct. 16, 2012. PMID: 23073843; PMCID: PMC3489998.
Zhang et al., Ultrasensitive response motifs: basic amplifiers in molecular signalling networks. Open Biol. 3, 130031 (2013).

*Primary Examiner* — Samuel C Woolwine
*Assistant Examiner* — Tiffany Nicole Grooms
(74) *Attorney, Agent, or Firm* — Wolf, Greenfield & Sacks, P.C.

(57) ABSTRACT

Provided herein are genetic circuits and encoded RNA transcripts that produce an output molecule in response to an RNA cleavage event that removes a degradation signal. In some embodiments, the genetic circuits described herein may be used for detecting RNA cleaver activities (e.g., in a cell). Methods of using the genetic circuits described herein in diagnostic or therapeutic applications are also provided.

14 Claims, 11 Drawing Sheets
Specification includes a Sequence Listing.

RNA CLEAVAGE-INDUCED TRANSCRIPT STABILIZER AND USES THEREOF

RELATED APPLICATION

This application claims the benefit under 35 U.S.C. § 119(e) to U.S. Provisional Application No. 62/539,375, filed Jul. 31, 2017, and entitled "RNA CLEAVAGE-INDUCED TRANSCRIPT STABILIZER AND USES THEREOF," the entire contents of which are incorporated herein by reference.

GOVERNMENT SUPPORT

This invention was made with Government support under Grant No. R01 CA207029 awarded by National Institutes of Health. The Government has certain rights in the invention.

REFERENCE TO A SEQUENCE LISTING SUBMITTED AS A TEXT FILE VIA EFS-WEB RELATED APPLICATIONS

The present application contains a Sequence Listing which has been submitted in ASCII format via EFS-Web and is hereby incorporated by reference in its entirety. Said ASCII copy, created on Jul. 30, 2018, is named M065670421US01-SEQ-ZJG and is 42,246 bytes in size.

BACKGROUND

RNA cleavage is an important process during cellular RNA processing. Existing methods of detecting RNA cleavage activities (e.g., RNA cleavage mediated by a microRNA) usually involve a "double-inversion" strategy, where the RNA cleavage sites are engineered into a transcript encoding a translational or transcriptional repressor of a reporter. As such, high levels of RNA cleavage leads to low repressor expression, which in turn rescues reporter expression. A "time delay" exists between the detection of the RNA cleavage and the production of the reporter.

SUMMARY

The present disclosure, in some aspects, relates to genetic circuits and modules that directly respond to RNA cleavage (e.g., cleavage mediated by RNAi, cis- or trans-acting ribozymes and ribonucleases) and produce an output molecule (e.g., a detectable molecule, a therapeutic molecule, or a functional molecule). Such genetic circuits incorporate RNA degradation signals that lead to the degradation of the RNA molecule. The RNA degradation signals are removed via RNA cleavage, stabilizing the RNA and resulting in expression of the output molecule.

Some aspects of the present disclosure provide cleavage-induced transcript stabilizers, containing: (i) a first promoter operably linked to a nucleotide sequence encoding an output molecule followed, from 5' to 3', by an RNA stabilizer, a cleavage site for an RNA cleaver, and a degradation signal. In some embodiments, the cleavage-induced transcript stabilizer further contains (ii) a second promoter operably linked to a nucleotide sequence encoding the RNA cleaver.

In some embodiments, the RNA cleaver is selected from the group consisting of: endoribonucleases, RNAi molecules, and ribozymes. In some embodiments, the RNA cleaver is an endoribonuclease. In some embodiments, the endoribonuclease is selected from the group consisting of: Cse3, Cas6, CasE, and Csy4. In some embodiments, the cleavage site contains a recognition sequence for the endoribonuclease.

In some embodiments, the RNA cleaver is an RNAi molecule. In some embodiments, the RNAi molecule is a microRNA, siRNA, or shRNA. In some embodiments, the cleavage site contains one or more target sites for the RNAi molecule.

In some embodiments, the RNA cleaver is a ribozyme. In some embodiments, the ribozyme is selected from the group consisting of: RNase P, HDV ribozyme, hammerhead ribozyme, hairpin ribozyme, twister ribozyme, twister sister ribozyme, pistol ribozyme, hatchet ribozyme, glmS ribozyme, varkud satellite ribozyme, and spliceozyme. In some embodiments, the ribozyme is a trans-acting ribozyme. In some embodiments, the cleavage site contains a recognition site for the trans-acting ribozyme. In some embodiments, the ribozyme is a cis-acting ribozyme. In some embodiments, the cleavage site contains the cis-acting ribozyme.

In some embodiments, the cleavage-induced transcript stabilizer further contains a third promoter operably linked to a third nucleotide sequence encoding an RNA repressor, and one or more the cleavage sites for the RNA cleaver. In some embodiments, the cleavage-induced transcript stabilizer further contains one or more recognition sites for an RNA repressor operably linked of the nucleotide sequence encoding the output molecule.

In some embodiments, the RNA repressor is an RNA binding protein. In some embodiments, the RNA binding protein is selected from the group consisting of: TetR, CNOT7, DDX6, PPR10, and L7Ae.

In some embodiments, the cleavage-induced transcript stabilizer contains 1-50 repeats of the degradation signal. In some embodiments, the cleavage-induced transcript stabilizer contains 10 repeats of the degradation signal. In some embodiments, the cleavage-induced transcript stabilizer contains 30 repeats of the degradation signal. In some embodiments, the degradation signal contains the nucleotide sequence of TAASTTAT (SEQ ID NO: 1), wherein S is deoxyguanosine or deoxycytosine. In some embodiments, the degradation signal contains the nucleotide sequence of TAAGTTAT (SEQ ID NO: 2). In some embodiments, the degradation signal contains the nucleotide sequence of TAAGACAT (SEQ ID NO: 3).

In some embodiments, the RNA stabilizer is selected from the group consisting of: MALAT1 triplex, MENβ triplex, KSHV PAN triplex, histone stem loop, and a polyA signal. In some embodiments, the RNA stabilizer is a MALAT1 triplex. In some embodiments, the output molecule is a detectable molecule. In some embodiments, the output molecule is a therapeutic molecule. In some embodiments, the output molecule is a functional molecule. In some embodiments, wherein the functional molecule is selected from the group consisting of: TetR, CNOT7, DDX6, PPR10, L7Ae, Csy4, Cas6, CasE, and Cse3.

In some embodiments, the second promoter of (ii) is an inducible promoter.

An "RNA version" of the cleavage-induced transcript stabilizer is also provided, containing: (i) an RNA transcript containing a ribonucleotide sequence encoding an output molecule followed, in order, by an RNA stabilizer, a cleavage site for an RNA cleaver, and a degradation signal that leads to degradation of the RNA transcript. In some embodiments, the RNA version of the cleavage-induced transcript stabilizer further contains: (ii) a promoter operably linked to a nucleotide sequence encoding an RNA cleaver that cleaves the RNA transcript at the cleavage site. In some embodiments, the promoter of (ii) is an inducible promoter. In some embodiments, the RNA transcript is degraded without in the absence of the RNA cleaver. In some embodiments, the RNA cleaver is expressed in the presence of the RNA cleaver. In some embodiments, the cleavage of the RNA transcript stabilizes the RNA transcript and results in expression of the output molecule.

In some embodiments, the output molecule is a detectable molecule. In some embodiments, the output molecule is a therapeutic molecule. In some embodiments, the output molecule is a functional molecule. In some embodiments, wherein the functional molecule is selected from the group consisting of: TetR, CNOT7, DDX6, PPR10, L7Ae, Csy4, Cas6, CasE, and Cse3.

Cells containing the cleavage-induced transcript stabilizers described herein are provided. In some embodiments, the cell is a prokaryotic cell. In some embodiments, the prokaryotic cell is a bacterial cell. In some embodiments, the cell is a eukaryotic cell. In some embodiments, the eukaryotic cell is a plant cell, an insect cell, or a mammalian cell. In some embodiments, the mammalian cell is a human cell. In some embodiments, the cell is a diseased cell. In some embodiments, the cell is a cancer cell. In some embodiments, the cleavage-induced transcript stabilizer is inserted into the genome of the cell.

Other aspects of the present disclosure provide methods of using the cleavage-induced transcript stabilizer described herein. In some embodiments, the method contains maintaining the cells containing the cleavage-induced transcript stabilizer. In some embodiments, the method further contains detecting the output molecule. In some embodiments, the method further contains classifying the cell.

In some embodiments, the method contains delivering the cleavage-induced transcript stabilizer described herein to a cell and detecting the output molecule.

In some embodiments, the cleavage-induced transcript stabilizer are used in a method of detecting an RNA cleaver activity, the method contains: delivering the cleavage-induced transcript stabilizer described herein to a cell and detecting the output molecule. In some embodiments, the RNA cleaver is an endoribonuclease, a siRNA transcript, or a ribozyme.

Methods of treating a disease or disorder are provided, the method contains delivering the cleavage-induced transcript stabilizer described herein to a cell, wherein the output molecule is a therapeutic molecule that is effective for treating the disease or disorder. In some embodiments, the method contains administering an effective amount of a composition containing the cleavage-induced transcript stabilizer described herein to a subject in need thereof, wherein the output molecule is a therapeutic molecule that is effective for treating the disease or disorder. In some embodiments, the composition further contains a pharmaceutically acceptable carrier. In some embodiments, the cell is a diseased cell. In some embodiments, the cell is a cancer cell.

Methods of diagnosing a disease or disorder are provided, the method contains delivering the cleavage-induced transcript stabilizer described herein to a cell. In some embodiments, the method contains administering an effective amount of a composition containing the cleavage-induced transcript stabilizer described herein to a subject in need thereof. In some embodiments, the composition further contains a pharmaceutically acceptable carrier. In some embodiments, the cell is a diseased cell. In some embodiments, the cell is a cancer cell. In some embodiments, the method further contains detecting the output molecule. In some embodiments, the lack of expression of the output molecule indicates the disease or disorder. In some embodiments, the expression of the output molecule indicates the disease or disorder.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

BRIEF DESCRIPTION OF THE DRAWINGS

The accompanying drawings are not intended to be drawn to scale. For purposes of clarity, not every component may be labeled in every drawing.

(FIG. 1A) A schematic of the signal inversion module described herein. (FIG. 1B) A comparison between a traditional module that detects RNA cleavage and the module described herein. Scissors represent an RNA cleaver such as a ribonuclease, miRNA, or ribozyme. Line plots show sample curves for transgene expression response to RNA cleaver level (FIG. 1B).

(FIG. 3A) Expression response to degradation sequences. "wt1" indicates the wild type Geissler degradation sequence while "mut1" indicates the mutated version. Lines, from top to bottom at right end: EYFP, EYFP-10xmut1, EYFP-10xwt1, background. (FIG. 3B) Effects of the triplex on degradation domains. "Trpx" indicates triplex sequence. Lines, from top to bottom at right end: EYFP, EYFP-Trpx, EYFP-Trpx-10xwt1, EYFP-10xwt1, background. (FIG. 3C) Effects of Geissler degradation sequence repeat count. Lines, from top to bottom at right end: EYFP-Trpx, EYFP-Trpx-10xwt1, EYFP-Trpx-20xwt1, EYFP-Trpx-30xwt1, background. (FIG. 3D) Bar plots of geometric mean normalized to background fluorescence. Colors and patterns match those indicated in line plots (FIGS. 3A-3C), from left to right: EYFP, EYFP-10xwt1, EYFP-10xmut1, EYFP-Trpx, EYFP-Trpx-10xwt1, EYFP-Trpx-20xwt1, EYFP-Trpx-30xwt1.

(FIG. 4A) Titration curves of for Csy4. The line that slopes down from left to right indicates traditional "OFF" switch while the line that slopes up from left to right indicates novel "ON" switch. (FIGS. 4B-4E) Response of the cleavage-induced transcript stabilizer described herein cleavage by Csy4, Cse3, Cas6, and CasE respectively.

(FIG. 5A) Response of the cleavage-induced transcript stabilizer described herein to siRNA FF5. Lines, from top to bottom at right end: EYFP-Trpx, EYFP-Trpx-30xwt1, EYFP-Trpx-FF5ts-30xwt1 (+siRFF5), EYFP-Trpx-FF5ts-30xwt1 (−siRFF5), background. (FIG. 5B) Bar plots of geometric mean normalized to background fluorescence. Colors and patterns match those indicated in line plots. From left to right: EYFP-Trpx, EYFP-Trpx-30xwt1, EYFP-Trpx-FF5ts- 30xwt1 (−siRFF5), EYFP-Trpx-FF5ts-30xwt1 (+siRFF5). (FIG. 5C) Response of the cleavage-induced transcript stabilizer described herein to siRNA FF3. An increase in the level of output molecule was observed. (FIG. 5D) Response of the cleavage-induced transcript stabilizer described herein to microRNA FF5.

(FIG. 6A) Response of the cleavage-induced transcript stabilizer described herein to inactive (iHHR) and active (HHR) hammerhead ribozymes. Lines, from top to bottom at right end: EYFP-iHHR, EYFP, EYFP-HHR, background. (FIG. 6B) Bar plots of geometric mean normalized to background fluorescence. Colors and pattern match those indicated in line plots. From left to right: EYFP, EYFP-iHHR, EYFP-HHR. (FIG. 6C) In the absence of a polyA tail (the transcript should get degraded) fluorescence is rescued when the mascRNA sequence (which is targeted by RNase P) is added after the triplex.

(FIG. 7A) Titration curves for L7Ae. (FIG. 7B) Background of the "ON"-switch is decreased (as indicated by a shift of the curve to the right) by incorporating the L7Ae construct for an ultrasensitive response.

DETAILED DESCRIPTION OF CERTAIN EMBODIMENTS

Provided herein, in some aspects, are genetic circuits and modules that express an output molecule in response to RNA cleavage (e.g., cleavage mediated by RNAi, cis- or trans-acting ribozymes and ribonucleases). Such genetic circuits incorporates RNA degradation signals that leads to the degradation of the RNA molecule. The RNA degradation signals are removed via RNA cleavage, stabilizing the RNA and resulting in expression of the output molecule. The genetic circuits described herein may be used for the detection of RNA cleaver activities (e.g., in a cell), and for diagnostic or therapeutic applications.

Figure 1A:
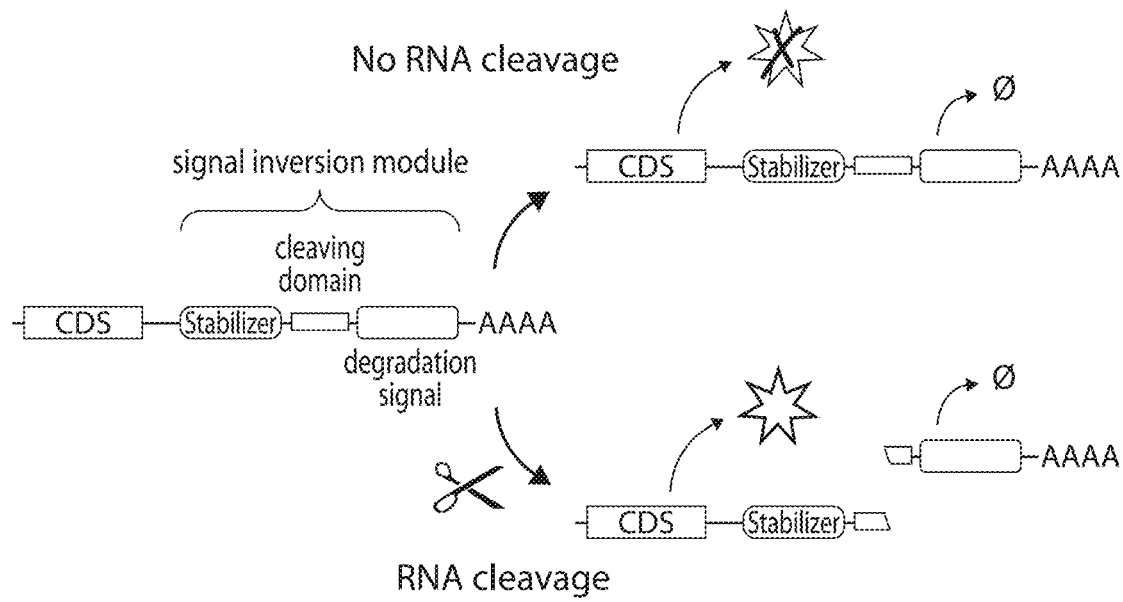
FIGS. 1A-1B: Inverter module schematic.

Some aspects of the present disclosure provide a cleavage-induced transcript stabilizer. A "cleavage-induced transcript stabilizer," as used herein, refers to an RNA transcript that is rapidly degraded due to the presence of a degradation signal in the RNA transcript, but is stabilized upon an RNA cleavage event (e.g., by an endonuclease or a ribozyme) that removes the degradation signal. A genetic circuit that encodes such RNA transcript (i.e., the DNA version of the transcript) is also referred to herein as a "cleavage-induced transcript stabilizer." The "DNA version" of the cleavage-induced transcript stabilizer comprises a first promoter operably linked to a nucleotide sequence encoding an output molecule followed, from 5' to 3', by an RNA stabilizer, a cleavage site for an RNA cleaver, and a degradation signal. The "RNA version" of the cleavage-induced transcript stabilizer comprises a nucleotide sequence encoding an output molecule followed, from 5' to 3', by an RNA stabilizer, a cleavage site for an RNA cleaver, and a degradation signal. The order of the RNA stabilizer, the cleavage site for the RNA cleaver and the degradation signal needs to be such that the RNA stabilizer is downstream of and next to the nucleotide sequence encoding the output molecule; the cleavage site for the RNA cleaver is downstream of and next to the RNA stabilizer; and the degradation signal is downstream and next to the cleavage site of the RNA cleaver (i.e., at the 3' end). An exemplary structure of the cleavage-induced transcript stabilizer is shown in FIG. 1A.

As described herein, a "degradation signal," refers to a cis-acting nucleotide sequence that directs the RNA transcript to degradation, e.g., via the recruitment of enzymes involved in RNA degradation to the RNA molecule. Being "cis-acting" means that the degradation signal is part of the RNA transcript that it directs to degradation. In some embodiments, the degradation signal is present in the 3' untranslated region (3'UTR) or the RNA transcript. In some embodiments, the degradation signals are appended at the 3' end of the RNA transcript. In some embodiments, appending the degradation signal at the 3' end of the RNA transcript maximizes its degradative strength.

In some embodiments, the degradation signal is 5-30 nucleotides long. For example, the degradation signal may be 5-30, 5-25, 5-20, 5-15, 5-10, 10-30, 10-25, 10-20, 10-15, 15-30, 15-25, 15-20, 20-30, 20-25, or 25-30 nucleotides long. In some embodiments, the degradation signal is 5, 6, 7, 8, 9, 10, 11, 12, 13, 14, 15, 16, 17, 18, 19, 20, 21, 22, 23, 24, 25, 26, 27, 28, 29, or 30 nucleotides long. In some embodiments, longer (e.g., >30 nt) or shorter (e.g., <5 nt) degradation signals are used.

In some embodiments, the degradation signal comprises a 8-nt RNA motif that naturally occurs in the 3' UTR of human transcripts and directs the transcripts to degrade (e.g., as described in Geissler et al., Genes & Dev. 2016. 30: 1070-1085, incorporated herein by reference). In some embodiments, in the DNA version of the cleavage-induced transcript stabilizer, the degradation signal comprises the nucleotide sequence of TAASTTAT (SEQ ID NO: 1), wherein S is deoxyguanosine or deoxycytosine. In some embodiments, in the DNA version of the cleavage-induced transcript stabilizer, the degradation signal comprises the nucleotide sequence of TAAGTTAT (SEQ ID NO: 2) or TAACTTAT (SEQ ID NO: 4). In some embodiments, in the DNA version of the cleavage-induced transcript stabilizer, the degradation signal comprises the nucleotide sequence of TAAGACAT (SEQ ID NO: 3), which was shown herein the have induced more robust RNA degradation than the TAAGTTAT (SEQ ID NO: 2) degradation signals (e.g., in FIGS. 3A and 3D).

In some embodiments, in the RNA version of the cleavage-induced transcript stabilizer, the degradation signal comprises the nucleotide sequence of UAASUUAU (SEQ ID NO: 5), wherein S is guanosine or cytosine. In some embodiments, in the RNA version of the cleavage-induced transcript stabilizer, the degradation signal comprises the nucleotide sequence of UAAGUUAU (SEQ ID NO: 6) or UAACUUAU (SEQ ID NO: 7). In some embodiments, in the DNA version of the cleavage-induced transcript stabilizer, the degradation signal comprises the nucleotide sequence of UAAGACAU (SEQ ID NO: 8).

Other known degradation signals that lead to degradation of RNA transcripts (e.g., as described in Matoulkova et al., RNA Biology, 9:5, 563-576, 2012, incorporated herein by reference) may also be used in accordance with the present disclosure, including, without limitation: AU-rich elements, GU-rich elements, CA-rich elements, and introns.

In some embodiments, the RNA transcript comprises 1-50 repeats of the degradation signal. For example, the RNA transcript may comprise 1-10, 1-20, 1-30, 1-40, 1-50, 10-50, 10-40, 10-30, 10-20, 20-50, 20-40, 20-30, 30-50, 30-40, or 40-50 repeats of the degradation signal. In some embodiments, the RNA transcript comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 repeats of the degradation signal. In some embodiments, the RNA transcript comprises more than 50 (e.g., 60, 70, 80, 90, 100, or more) repeats of the degradation signal.

In some embodiments, the presence of the degradation signal in the RNA transcript reduces the level and/or the half-life of the RNA transcript by at least 30%. For example, the presence of the degradation signal in the RNA transcript may reduce the level and/or the half-life of the RNA transcript by at least 30%, at least 40%, at least 50%, at least 100%, at least 3-fold, at least 5-fold, at least 10-fold, at least 20-fold, at least 30-fold, at least 40-fold, at least 50-fold, at least 60-fold, at least 70-fold, at least 80-fold, at least 90-fold, at least 100-fold, or more. In some embodiments, the presence of the degradation signal in the RNA transcript reduces the level and/or the half-life of the RNA transcript by 30%, 40%, 50%, 100%, 3-fold, 5-fold, 10-fold, 20-fold, 30-fold, 40-fold, 50-fold, 60-fold, 70-fold, 80-fold, 90-fold, 100-fold, or more.

The RNA transcript to which the degradation signal is appended encodes the output molecule. As such, the presence of the degradation signal in the RNA transcript reduces the level and/or activity of the output molecule by at least 30%. For example, the presence of the degradation signal in the RNA transcript may reduce the level and/or activity of the output molecule by at least 30%, at least 40%, at least 50%, at least 100%, at least 3-fold, at least 5-fold, at least 10-fold, at least 20-fold, at least 30-fold, at least 40-fold, at least 50-fold, at least 60-fold, at least 70-fold, at least 80-fold, at least 90-fold, at least 100-fold, or more. In some embodiments, the presence of the degradation signal in the RNA transcript reduces the level and/or activity of the RNA transcript by 30%, 40%, 50%, at least 100%, 3-fold, 5-fold, 10-fold, 20-fold, 30-fold, 40-fold, 50-fold, 60-fold, 70-fold, 80-fold, 90-fold, 100-fold, or more. In some embodiments, in the presence of the degradation signal in the RNA transcript, the output molecule does not expression or has a level of expression that is not detectable (e.g., by routine methods such as western blotting).

The present disclosure provides a strategy where the RNA transcript is cleaved between the nucleotide sequence encoding the output molecule and the degradation signal, such that the degradation signal is removed and the RNA transcript is stabilized. The cleavage may be carried out by an RNA cleaver.

An "RNA cleaver," as used herein, refers to a molecule that cleaves the phosphodiester bond between two ribonucleotides, thus resulting two fragments of the RNA transcript, a 5' fragment and a 3' fragment. The RNA cleavers of the present disclosure cleaves the RNA transcript in a sequence-specific manner. Exemplary sequence-specific RNA cleavers include, without limitation, certain endoribonucleases, RNA interference (RNAi) molecules, and ribozymes (e.g., cis-acting ribozyme or trans-acting ribozyme). The RNA cleaver of the present disclosure may directly cleave the RNA transcript (e.g., an endoribonuclease or a ribozyme) or indirectly leads to the cleavage of the RNA transcript (e.g., via the recruitment of other factors that carrier out the cleavage). A non-limiting example of an RNA cleaver that indirectly cleaves the RNA transcript is an RNAi molecule, which is incorporated in a the RNA-induced silencing complex (RISC) that binds and cleaves a target sequence in the RNA transcript.

In some embodiments, the RNA cleaver is an endoribonuclease. An "endoribonuclease," as used herein, refers to a nuclease that cleaves an RNA molecule in a sequence specific manner, e.g., at a recognition site. Sequence-specific endoribonucleases have been described in the art. For example, the *Pyrococcus furiosus* CRISPR-associated endoribonuclease 6 (Cas6) is found to cleave RNA molecules in a sequence-specific manner (Carte et al., Genes & Dev. 2008. 22: 3489-3496, incorporated herein by reference). In another example, endoribonucleases that cleave RNA molecules in a sequence-specific manner are engineered, which recognize an 8-nucleotide (nt) RNA sequence and make a single cleavage in the target (Choudhury et al., Nature Communications 3, 1147 (2012), incorporated herein by reference).

In some embodiments, the endoribonuclease belongs to the CRISPR-associated endoribonuclease 6 (Cas6) family. Cas6 nucleases from different bacterial species may be used. Non-limiting examples of Cas6 family nucleases include Cas6, Csy4 (also known as Cas6f), Cse3, and CasE.

When an endoribonuclease is used as the RNA cleaver, the recognition site for the RNA cleaver in the RNA transcript comprises one or more (e.g., 1, 2, 3, 4, 5, 6, 7, 8, 9, 10 or more) recognition sites for the endoribonuclease. A "recognition site for an endoribonuclease" refers to a ribonucleotide sequence that is recognized, bound, and cleaved by the endoribonuclease. The recognition site for an endoribonuclease may be 4-20 nucleotides long. For example, the recognition site may be 4, 5, 6, 7, 8, 9, 10, 11, 12, 13, 14, 15, 16, 17, 18, 19, or 20 nucleotides long. In some embodiments, endoribonuclease recognition sites that are shorter than 4 ribonucleotides or longer than 20 nucleotides are used. Table 1 provides the amino acid and nucleotide sequences of exemplary endoribonucleases and their respective recognition sites.

TABLE 1

Non-limiting, Exemplary Endoribonucleases and Recognition Sites

| Endoribonuclease/ Bacterial species | Amino acid sequence | Gene Sequence | Recognition site sequence |
|---|---|---|---|
| Cas6/*Pyrococcus furiosus* | MRFLIRLVPEDKDR AFKVPYNHQYYLQ GLIYNAIKSSNPKL ATYLHEVGPKLFT YSLFMAEKREHPK GLPYFLGYKKGFFY FSTCVPEIAEALVN GLLMNPEVRLWDE RFYLHEIKVLREPK KFNGSTFVTLSPIA VTVVRKGKSYDVP PMEKEFYSIIKDDL QDKYVMAYGDKPP SEFEMEVLIAKPKR FRIKPGIYQTAWHL | ATGCGCTTCCTCATTCGTCTCGTGCCT GAGGATAAGGATCGGGCCTTTAAAGT GCCATATAACCATCAGTATTACCTGC AGGGCCTCATCTATAATGCCATCAAA TCCTCCAATCCGAAGCTGGCCACCTA CCTGCATGAGGTGAAGGGTCCCAAAC TGTTCACCTACAGCCTGTTTATGGCCG AAAAACGCGAACACCCTAAGGGGCTG CCTTACTTTTTGGGGTACAAGAAGGG CTTCTTCTACTTTTCTACCTGCGTGCC GGAGATCGCTGAAGCACTGGTCAACG GACTCCTGATGAATCCAGAGGTGCGC CTGTGGGACGAACGCTTCTACCTGCA CGAAATTAAGGTTTTGAGAGAGCCTA AGAAGTTCAACGGCTCTACCTTCGTC | GTTACAAT AAGACTAA ATAGAATT GAAAG (SEQ ID NO: 11) |

TABLE 1-continued

Non-limiting, Exemplary Endoribonucleases and Recognition Sites

| Endoribonuclease/ Bacterial species | Amino acid sequence | Gene Sequence | Recognition site sequence |
|---|---|---|---|
|  | VFRAYGNDDLLKV GYEVGFGEKNSLG FGMVKVEGNKTTK EAEEQEKITFNSRE ELKTGV (SEQ ID NO: 9) | ACCCTGTCTCCGATTGCTGTGACTGTC GTGAGGAAGGGTAAGAGTTATGATGT CCCCCCTATGGAGAAGGAGTTTTACA GTATCATCAAAGACGACCTGCAAGAT AAGTATGTGATGCCTACGGCGACAA GCCCCCATCCGAATTCGAGATGGAGG TGCTGATTGCTAAGCCGAAACGGTTT CGTATTAAGCCTGGCATCTATCAGAC AGCCTGGCACCTGGTTTTTAGGGCCTA CGGAAACGACGACCTGCTGAAGGTTG GTTACGAGGTTGGGTTCGGAGAAAAG AACTCCCTGGGATTCGGCATGGTGAA GGTGGAGGGGAACAAGACCACAAAA GAAGCTGAAGAGCAGGAAAAGATCA CCTTCAACTCTCGCGAGGAGCTGAAG ACCGGCGTGTGA (SEQ ID NO: 10) |  |
| Csy4/Pseudomonas aeruginosa | MDHYLDIRLRPDPE FPPAQLMSVLFGKL HQALVAQGGDRIG VSFPDLDESRSRLG ERLRIHASADDLRA LLARPWLEGLRDH LQFGEPAVVPHPTP YRQVSRVQAKSNP ERLRRRLMRRHDL SEEEARKRIPDTVA RALDLPFVTLRSQS TGQHFRLFIRHGPL QVTAEEGGFTCYG LSKGGFVPWF (SEQ ID NO: 12) | ATGGACCACTATCTGGACATCAGACT GAGGCCCGATCCTGAGTTCCCTCCCG CCCAGCTGATGAGCGTGCTGTTTGGC AAGCTGCATCAGGCTCTGGTCGCCCA AGGCGGAGACAGAATCGGCGTGTCCT TCCCCGACCTGGACGAGTCCCGGAGT CGCCTGGGCGAGCGGCTGAGAATCCA CGCCAGCGCAGACGATCTGCGCGCCC TGCTGGCCCGGCCTTGGCTGGAGGGC CTGCGGGATCATCTGCAGTTTGGCGA GCCCGCCGTGGTGCCACACCCAACAC CCTACCGCCAGGTGAGCCGCGTGCAG GCCAAGTCAAATCCCGAGAGACTGCG GCGGAGGCTGATGAGGCGACATGATC TGAGCGAGGAGGAGGCCAGAAAGAG AATCCCCGACACAGTGGCCAGAGCCC TGGATCTGCCATTTGTGACCCTGCGGA GCCAGAGCACTGGCCAGCATTTCAGA CTGTTCATCAGACACGGGCCCCTGCA GGTGACAGCCGAGGAGGGCGGATTTA CATGCTATGGCCTGTCTAAAGGCGGC TTCGTGCCCTGGTTCTGA (SEQ ID NO: 13) | GTTCACTG CCGTATAG GCAGCTAA GAAA (SEQ ID NO: 14) |
| CasE/Escherichia coli | MYLSKIIIARAWSR DLYQLHQEDWHLF PNRPDAARDFLFHV EKRNTPEGCHVLL QSAQMWVSTAVAT VIKTKQVEFQLQVG VPLYFRLRANPIKTI LDNQKRLDSKGNI KRCRVPLIKEAEQI AWLQRKLGNAAR VEDVHPISERPQYF SGEGKNGKIQTVCF EGVLTINDAPALID LLQQGIGPAKSMG CGLLSLAPL(SEQ ID NO: 15) | ATGTACCTCAGTAAGATCATCATCGC CCGCGCTTGGTCCCGTGACCTGTACCA ACTGCACCAAGAGCTCTGGCACCTCT TCCCCAACAGGCCAGATGCCGCTAGA GACTTCCTGTTCCACGTGGAGAAGCG TAACACCCCCGAAGGGTGCCACGTGC TGTTGCAGAGTGCCCAGATGCCAGTG AGTACCGCTGTTGCCACTGTCATCAA GACTAAACAAGTTGAATTCCAACTGC AAGTGGGCGTCCCTCTGTATTTCCGCC TCAGGGCCAACCCCATCAAAACCATC CTGGACAACCAGAAGCGGCTGGATAG CAAAGGTAATATCAAGAGATGCCGCG TGCCTCTGATCAAGGAGGCCGAGCAG ATCGCTTGGCTGCAACGCAAGCTGGG TAACGCCGCGAGAGTGGAAGATGTGC ACCCAATCTCCGAGCGCCCGCAGTAT TTCTCCGGGGAGGGGAAGAACGGCAA AATTCAGACTGTCTGCTTCGAGGGGG TGCTCACTATTAACGACGCCCCTGCTC TGATCGACCTCCTGCAGCAGGGCATT GGGCCCGCGAAGAGCATGGGATGCGG ATTGTTGAGCCTGGCACCCCTG (SEQ ID NO: 16) | GAGTTCCC CGCGCCAG CGGGGATA AACCG (SEQ ID NO: 17) |
| Cse3/Thermus thermophilus | MWLTKLVLNPASR AARRDLANPYEWH RTLSKAVSRALEEG RERLLWRLEPARG LEPPVVLVQTLTEP DWSVLDEGYAQVF PPKPFHPALKPGQR LRFRLRANPAKRLA ATGKRVALKTPAE | ATGTGGTTGACCAAATTGGTTCTGAAT CCTGCGAGCCGCGCAGCACGGCGCGA TTTGGCTAACCCTTACGAGATGCATCG GACTCTTTCAAAAGCGGTTAGCAGGG CTTTGGAAGAAGGGCGCGAGCGCCTT TTGTGGAGGCTGGAGCCAGCTCGGGG ACTGGAGCCCCCTGTCGTCCTGGTGC AGACCCTCACTGAGCCTGATTGGTCC GTACTTGATGAAGGTTACGCACAGGT | GTAGTCCC CACGCGTG TGGGGATG GACCG (SEQ ID NO: 20) |

TABLE 1-continued

Non-limiting, Exemplary Endoribonucleases and Recognition Sites

| Endoribonuclease/ Bacterial species | Amino acid sequence | Gene Sequence | Recognition site sequence |
|---|---|---|---|
| | KVAWLERRLEEGG FRLLEGERGPWVQI LQDTFLEVRRKKD GEEAGKLLQVQAV LFEGRLEVVDPERA LATLRRGVGPGKA LGLGLLSVAP (SEQ ID NO: 18) | CTTTCCTCCTAAGCCTTTCCACCCAGC ATTGAAGCCGGGCCAGCGGCTCCGCT TTAGGCTCCGGGCGAATCCCGCCAAA CGGTTGGCTGCCACCGGAAAGCGAGT TGCGTTGAAAACGCCCGCCGAAAAAG TGGCGTGGCTTGAGAGGCGGCTGGAG GAGGGTGGTTTTCGACTCCTTGAAGG GGAAAGGGGACCATGGGTACAGATAC TTCAAGATACGTTCCTGGAGGTGCGG AGAAAAAAAGACGGAGAAGAGGCAG GCAAGCTGCTTCAAGTCCAAGCCGTC TTGTTCGAGGGGAGACTCGAAGTTGT TGATCCTGAGAGAGCACTTGCGACAC TGAGACGAGGGGTGGGACCTGGTAAA GCGCTGGGTCTTGGACTTCTTAGTGTT GCACCATGA (SEQ ID NO: 19) | |

In some embodiments, the RNA cleaver is a ribozyme (e.g., a cis-acting ribozyme or a trans-acting ribozyme). A "ribozyme" is an RNA molecule that is capable of catalyzing specific biochemical reactions, similar to the action of protein enzymes. In some embodiments, the ribozyme is a cis-acting ribozyme. A "cis-acting ribozyme" refers to a ribozyme that catalyzes self-cleavage (intramolecular or "in-cis" catalysis) from the RNA molecule that contains the ribozyme itself. In these instances, the cleavage site for the RNA cleaver in the RNA transcript of the present disclosure comprises the cis-acting ribozyme, which upon cleavage, excises itself and leaving two separated fragments of the RNA transcript. In some embodiments, the ribozyme is a trans-acting ribozyme. A "trans-acting ribozyme," as used herein, refers to a ribozyme that cleaves an external substrate in a specific-manner. In these instances, the cleavage site for the RNA cleaver in the RNA transcript of the present disclosure comprises the recognition and cleavage sites for the trans-acting ribozyme. Suitable ribozymes that may be used in accordance with the present disclosure and their respective sequences include, without limitation: RNase P, hammerhead ribozymes, Hepatitis delta virus ribozymes, hairpin ribozymes, twister ribozymes, twister sister ribozymes, pistol ribozymes, hatchet ribozymes, glmS ribozymes, varkud satellite ribozymes, and spliceozyme. Naturally occurring ribozymes may be used. Further, ribozymes engineered such that they cleave their substrates in cis or in trans, e.g., as described in Carbonell et al. *Nucleic Acids Res.* 2011 March; 39(6): 2432-2444, incorporated herein by reference. Minimal ribozymes (i.e., the minimal sequence a ribozyme needs for its function, e.g., as described in Scott et al., *Prog Mol Biol Transl Sci.* 2013; 120: 1-23, incorporated herein by reference) may also be used in accordance with the present disclosure. Non-limiting, exemplary ribozymes and their sequences are provided in Table 2.

TABLE 2

Non-limiting, Exemplary Ribozymes and Sequences

| Ribozyme | Cis or trans | Nucleotide sequence |
|---|---|---|
| Hammerhead | Cis | CACCACGAACCTGATGAGTCCGTGAGGACGAAACGAGCTAGCTCGTCGTTC GTGCTG (SEQ ID NO: 21) |
| Schistosoma-like hammerhead ribozyme | Cis | GGCGTCGGAGTATCCAATCAGTGGATGTACTACTCCCTGATGAGTCCCAAAT AGGACGAAACGCC (SEQ ID NO: 22) |
| Satellite virus hammerhead ribozyme | Cis | GGGTGCCCTGTCGGAGGATGTGCTTTCCTCCCTGATGAGTCCGTGAGGACGA AACAGGGCACCC (SEQ ID NO: 23) |
| Hepatitis delta virus ribozymes | Cis | GGCCGGCATGGTCCCAGCCTCCTCGCTGGCGCCGGCTGGGCAACATGCTTC GGCATGGCGAATGGGAC (SEQ ID NO: 24) |
| RNase P | trans | ATAGGGCGGAGGGAAGCTCATCAGTGGGGCCACGAGCTGAGTGCGTCCTGT CACTCCACTCCCATGTCCCTTGGGAAGGTCTGAGACTAGGGCCAGAGGCGG CCCTAACAGGGCTCTCCCTGAGCTTCGGGGAGGTGAGTTCCCAGAGAACGG GGCTCCGCGCGAGGTCAGACTGGGCAGGAGATGCCGTGGACCCCGCCCTTC GGGGAGGGGCCCGGCGGATGCCTCCTTTGCCGGAGCTTGGAACAGACTCAC GGCCAGCGAAGTGAGTTCAATGGCTGAGGTGAGGTACCCCGCAGGGGACCT CATAACCCAATTCAGACTACTCTCCTCCGCCCATT (SEQ ID NO: 25) Exemplary RNase P recognition sequence: GACGCTGGTGGCTGGCACTCCTGGTTTCCAGGACGGGGTTCAAGTCCCTGCG GTGTCT (SEQ ID NO: 26) |

In some embodiments, the RNA cleaver is an RNA interference (RNAi) molecule. An "RNAi molecule" refers to an RNA molecule that inhibit gene expression or translation, by recruiting RNA degradation factors to targeted mRNA molecules to degrade the mRNA. As the RNA cleaver of the present disclosure, RNAi molecules do not directly cleave the RNA transcript, but rather binds to their target sites in the mRNA transcript and induces cleavage of the RNA transcript by the RNA-induced silencing complex (RISC), which contains multiple proteins that can cleave and degrade the RNA transcript. Non-limiting examples of RNAi molecules include: microRNAs, small interfering RNAs (siRNA), and short hairpin RNAs (shRNA). These RNAi molecules vary in their origin and structure, but function in a similar manner in cleaving their target RNA transcript and gene silencing.

A "microRNA" or "miRNA" is a small non-coding RNA molecule that functions in RNA silencing and post-transcriptional regulation of gene expression (e.g., as described in Ambros et al., *Nature* 431 (7006): 350-5, 2004; and Bartel et al., *Cell.* 136 (2): 215-33, 2004).

A microRNA may be 15-30 nucleotides in length. For example, a microRNA may be 15-30, 15-25, 15-20, 20-30, 20-25, or 25-30 nucleotides in length. In some embodiments, a microRNA may be 16-24 nucleotides in length. In some embodiments, a microRNA may be 20-24 nucleotides in length. In some embodiments, a microRNA may be 15, 16, 17, 18, 19, 20, 21, 22, 23, 24, 25, 26, 27, 28, 29, or 30 nucleotides in length.

The microRNAs that may be used as the RNA cleavers of the present disclosure may be naturally occurring or synthetic. Information about the sequences, origins, and functions of known microRNAs maybe found in publically available databases (e.g., mirbase.org/, all versions, as described in Kozomara et al., *Nucleic Acids Res* 2014 42:D68-D73; Kozomara et al., *Nucleic Acids Res* 2011 39:D152-D157; Griffiths-Jones et al., *Nucleic Acids Res* 2008 36:D154-D158; Griffiths-Jones et al., *Nucleic Acids Res* 2006 34:D140-D144; and Griffiths-Jones et al., *Nucleic Acids Res* 2004 32:D109-D111, including the most recently released version miRBase 21, which contains "high confidence" microRNAs). Non-limiting examples of microRNAs that may be used as the RNA cleaver of the present disclosure are: FF4, FF5, let-7b, let-7c, let-7d, let-7e, let-7f, let-7g, let-7i, miR-100, miR-103, miR-106a, miR-107, miR-10a, miR-10b, miR-122, miR-125a, miR-125b, miR-126, miR-126*, miR-127-3p, miR-128a, miR-129, miR-133b, miR-135b, miR-137, miR-141, miR-143, miR-145, miR-146a, miR-146b, miR-148a, miR-149, miR-150, miR-155, miR-15a, miR-17-3p, miR-17-5p, miR-181a, miR-181b, miR-181c, miR-183, miR-184, miR-186, miR-187, miR-189, miR-18a, miR-190, miR-191, miR-192, miR-195, miR-197, miR-199a, miR-199a*, miR-19a, miR-19b, miR-200a, miR-200a*, miR-200b, miR-200c, miR-202, miR-203, miR-205, miR-20a, miR-21, miR-210, miR-216, miR-218, miR-22, miR-221, miR-222, miR-223, miR-224, miR-23a, miR-23b, miR-24, miR-25, miR-26a, miR-26b, miR-27a, miR-27b, miR-29a, miR-29b, miR-296-5p, miR-301, miR-302a, miR-302a*, miR-30a, miR-30b, miR-30c, miR-30d, miR-30e-3p, miR-30e-5p, miR-31, miR-320, miR-323, miR-324-5p, miR-326, miR-330, miR-331, miR-335, miR-346, miR-34a, miR-370, miR-372, miR-373, miR-373*, miR-497, miR-498, miR-503, miR-92, miR-93, miR-96, and miR-99a.

In some embodiments, the microRNA used as the RNA cleaver is selected from: hsa-let-7a-2-3p, hsa-let-7a-3p, hsa-let-7a-5p, hsa-let-7b-3p, hsa-let-7b-5p, hsa-let-7c-5p, hsa-let-7d-3p, hsa-let-7d-5p, hsa-let-7e-3p, hsa-let-7e-5p, hsa-let-7f-1-3p, hsa-let-7f-2-3p, hsa-let-7f-5p, hsa-let-7g-3p, hsa-let-7g-5p, hsa-let-7i-5p, hsa-miR-1, hsa-miR-1-3p, hsa-miR-1-5p, hsa-miR-100-3p, hsa-miR-100-5p, hsa-miR-101-3p, hsa-miR-101-5p, hsa-miR-103a-2-5p, hsa-miR-103a-3p, hsa-miR-105-3p, hsa-miR-105-5p, hsa-miR-106a-3p, hsa-miR-106a-5p, hsa-miR-106b-3p, hsa-miR-106b-5p, hsa-miR-107, hsa-miR-10a-3p, hsa-miR-10a-5p, hsa-miR-10b-3p, hsa-miR-10b-5p, hsa-miR-1185-1-3p, hsa-miR-1185-2-3p, hsa-miR-1185-5p, hsa-miR-122a-5p, hsa-miR-1249-3p, hsa-miR-1249-5p, hsa-miR-124a-3p, hsa-miR-125a-3p, hsa-miR-125a-5p, hsa-miR-125b-1-3p, hsa-miR-125b-2-3p, hsa-miR-125b-5p, hsa-miR-126-3p, hsa-miR-126-5p, hsa-miR-127-3p, hsa-miR-1271-3p, hsa-miR-1271-5p, hsa-miR-1278, hsa-miR-128-1-5p, hsa-miR-128-2-5p, hsa-miR-128-3p, hsa-miR-1285-3p, hsa-miR-1285-5p, hsa-miR-1287-3p, hsa-miR-1287-5p, hsa-miR-129-1-3p, hsa-miR-129-2-3p, hsa-miR-129-5p, hsa-miR-1296-3p, hsa-miR-1296-5p, hsa-miR-1304-3p, hsa-miR-1304-5p, hsa-miR-1306-3p, hsa-miR-1306-5p, hsa-miR-1307-3p, hsa-miR-1307-5p, hsa-miR-130a-3p, hsa-miR-130b-3p, hsa-miR-130b-5p, hsa-miR-132-3p, hsa-miR-132-5p, hsa-miR-133a-3p, hsa-miR-133a-5p, hsa-miR-133b, hsa-miR-134-3p, hsa-miR-134-5p, hsa-miR-135a-3p, hsa-miR-135a-5p, hsa-miR-135b-3p, hsa-miR-135b-5p, hsa-miR-136-3p, hsa-miR-136-5p, hsa-miR-138-1-3p, hsa-miR-138-5p, hsa-miR-139-3p, hsa-miR-139-5p, hsa-miR-140-3p, hsa-miR-140-5p, hsa-miR-141-3p, hsa-miR-141-5p, hsa-miR-142-3p, hsa-miR-142-5p, hsa-miR-143-3p, hsa-miR-143-5p, hsa-miR-144-3p, hsa-miR-144-5p, hsa-miR-145-5p, hsa-miR-146a-3p, hsa-miR-146a-5p, hsa-miR-147a, hsa-miR-148a-3p, hsa-miR-148a-5p, hsa-miR-148b-3p, hsa-miR-148b-5p, hsa-miR-149-3p, hsa-miR-144-3p, hsa-miR-150-3p, hsa-miR-150-5p, hsa-miR-151a-3p, hsa-miR-151a-5p, hsa-miR-152-3p, hsa-miR-152-5p, hsa-miR-154-3p, hsa-miR-154-5p, hsa-miR-155-3p, hsa-miR-155-5p, hsa-miR-15a-3p, hsa-miR-15a-5p, hsa-miR-15b-3p, hsa-miR-15b-5p, hsa-miR-16-1-3p, hsa-miR-16-2-3p, hsa-miR-16-5p, hsa-miR-17-3p, hsa-miR-17-5p, hsa-miR-181a-3p, hsa-miR-181a-5p, hsa-miR-181b-2-3p, hsa-miR-181b-5p, hsa-miR-181c-5p, hsa-miR-181d-3p, hsa-miR-181d-5p, hsa-miR-182-3p, hsa-miR-182-5p, hsa-miR-183-3p, hsa-miR-183-5p, hsa-miR-185-3p, hsa-miR-185-5p, hsa-miR-186-3p, hsa-miR-186-5p, hsa-miR-188-3p, hsa-miR-188-5p, hsa-miR-18a-3p, hsa-miR-18a-5p, hsa-miR-18b-5p, hsa-miR-1908-3p, hsa-miR-1908-5p, hsa-miR-190a-3p, hsa-miR-190a-5p, hsa-miR-191-3p, hsa-miR-191-5p, hsa-miR-1910-3p, hsa-miR-1910-5p, hsa-miR-192-3p, hsa-miR-192-5p, hsa-miR-193a-3p, hsa-miR-193a-5p, hsa-miR-193b-3p, hsa-miR-193b-5p, hsa-miR-194-3p, hsa-miR-194-5p, hsa-miR-195-3p, hsa-miR-195-5p, hsa-miR-196a-3p, hsa-miR-196a-5p, hsa-miR-196b-3p, hsa-miR-196b-5p, hsa-miR-197-3p, hsa-miR-197-5p, hsa-miR-199a-3p, hsa-miR-199a-5p, hsa-miR-199b-3p, hsa-miR-199b-5p, hsa-miR-19a-3p, hsa-miR-19a-5p, hsa-miR-19b-1-5p, hsa-miR-19b-2-5p, hsa-miR-19b-3p, hsa-miR-200a-3p, hsa-miR-200a-5p, hsa-miR-200b-3p, hsamiR-200b-5p, hsa-miR-200c-3p, hsa-miR-200c-5p, hsa-miR-202-3p, hsa-miR-202-5p, hsa-miR-203a-3p, hsa-miR-203a-5p, hsa-miR-204-5p, hsa-miR-208b-3p, hsa-miR-208b-5p, hsa-miR-20a-3p, hsa-miR-20a-5p, hsa-miR-20b-3p, hsa-miR-20b-5p, hsa-miR-21-5p, hsa-miR-210-3p, hsa-miR-210-5p, hsa-miR-211-3p, hsa-miR-211-5p, hsa-miR-2116-3p, hsa-miR-2116-5p, hsa-miR-212-3p, hsa-miR-214-3p, hsa-miR-215-5p, hsa-miR-217, JG_miR-218-1-3p, hsa-miR-218-5p, hsa-miR-219a-1-3p, hsa-miR-219a-2-3p, hsa-miR-219a-5p, hsa-miR-219b-3p, hsa-miR-219b-5p, hsa-miR-22-3p, hsa-miR-22-5p, hsa-miR-221-3p, hsa-miR-221-5p, hsa-miR-222-3p, hsa-miR-222-5p, hsa-miR-223-3p, hsa-miR-223-5p, hsa-miR-23a-3p, hsa-miR-23a-5p, hsa-miR-23b-3p, hsa-miR-24-1-5p, hsa-miR-25-3p, hsa-miR-25-5p, hsa-miR-26a-1-3p, hsa-miR-26a-2-3p, hsa-miR-26a-5p, hsa-miR-26b-5p, hsa-miR-27a-3p, hsa-miR-27a-5p, hsa-miR-27b-3p, hsa-miR-27b-5p, hsa-miR-28-3p, hsa-miR-28-5p, hsa-miR-296-3p, hsa-miR-296-5p, hsa-miR-299-3p, hsa-miR-299-5p, hsa-miR-29a-3p, hsa-miR-29a-5p, hsa-miR-29b-1-5p, hsa-miR-29b-3p, hsa-miR-29c-3p, hsa-miR-301a-3p, hsa-miR-301a-5p, hsa-miR-301b-3p, hsa-miR-301b-5p, hsa-miR-302a-3p, hsa-miR-302a-5p, hsa-miR-302b-5p, hsa-miR-302c-3p, hsa-miR-302c-5p, hsa-miR-3065-3p, hsa-miR-3065-5p, hsa-miR-3074-3p, hsa-miR-3074-5p, hsa-miR-30a-3p, hsa-miR-30a-5p, hsa-miR-30b-3p, hsa-miR-30b-5p, hsa-miR-30c-1-3p, hsa-miR-30c-2-3p, hsa-miR-30c-5p, hsa-miR-30d-3p, hsa-miR-30d-5p, hsa-miR-30e-3p, hsa-miR-30e-5p, hsa-miR-31-3p, hsa-miR-31-5p, hsa-miR-3130-3p, hsa-miR-3130-5p, hsa-miR-3140-3p, hsa-miR-3140-5p, hsa-miR-3144-3p, hsa-miR-3144-5p, hsa-miR-3158-3p, hsa-miR-3158-5p, hsa-miR-32-3p, hsa-miR-32-5p, hsa-miR-320a, hsa-miR-323a-3p, hsa-miR-323a-5p, hsa-miR-324-3p, hsa-miR-324-5p, hsa-miR-326, hsa-miR-328-3p, hsa-miR-328-5p, hsa-miR-329-3p, hsa-miR-329-5p, hsa-miR-330-3p, hsa-miR-330-5p, hsa-miR-331-3p, hsa-miR-331-5p, hsa-miR-335-3p, hsa-miR-335-5p, hsa-miR-337-3p, hsa-miR-337-5p, hsa-miR-338-3p, hsa-miR-338-5p, hsa-miR-339-3p, hsa-miR-339-5p, hsa-miR-33a-3p, hsa-miR-33a-5p, hsa-miR-33b-3p, hsa-miR-33b-5p, hsa-miR-340-3p, hsa-miR-340-5p, hsa-miR-342-3p, hsa-miR-342-5p, hsa-miR-345-3p, hsa-miR-345-5p, hsa-miR-34a-3p, hsa-miR-34a-5p, hsa-miR-34b-3p, hsa-miR-34b-5p, hsa-miR-34c-3p, hsa-miR-34c-5p, hsa-miR-3605-3p, hsa-miR-3605-5p, hsa-miR-361-3p, hsa-miR-361-5p, hsa-miR-3613-3p, hsa-miR-3613-5p, hsa-miR-3614-3p, hsa-miR-3614-5p, hsa-miR-362-3p, hsa-miR-362-5p, hsa-miR-363-3p, hsa-miR-363-5p, hsa-miR-365a-3p, hsa-miR-365a-5p, hsa-miR-365b-3p, hsa-miR-365b-5p, hsa-miR-369-3p, hsa-miR-369-5p, hsa-miR-370-3p, hsa-miR-370-5p, hsa-miR-374a-3p, hsa-miR-374a-5p, hsa-miR-374b-3p, hsa-miR-374b-5p, hsa-miR-375, hsa-miR-376a-2-5p, hsa-miR-376a-3p, hsa-miR-376a-5p, hsa-miR-376c-3p, hsa-miR-376c-5p, hsa-miR-377-3p, hsa-miR-377-5p, hsa-miR-378a-3p, hsa-miR-378a-5p, hsa-miR-379-3p, hsa-miR-379-5p, hsa-miR-381-3p, hsa-miR-381-5p, hsa-miR-382-3p, hsa-miR-382-5p, hsa-miR-409-3p, hsa-miR-409-5p, hsa-miR-411-3p, hsa-miR-411-5p, hsa-miR-412-3p, hsa-miR-421, hsa-miR-423-3p, hsa-miR-423-5p, hsa-miR-424-3p, hsa-miR-424-5p, hsa-miR-425-3p, hsa-miR-425-5p, hsa-miR-431-3p, hsa-miR-431-5p, hsa-miR-432-5p, hsa-miR-433-3p, hsa-miR-433-5p, hsa-miR-449a, hsa-miR-449b-5p, hsa-miR-450a-1-3p, hsa-miR-450a-2-3p, hsa-miR-450a-5p, hsa-miR-450b-3p, hsa-miR-450b-5p, hsa-miR-451a, hsa-miR-452-3p, hsa-miR-4524a-3p, hsa-miR-4524a-5p, hsa-miR-4536-3p, hsa-miR-4536-5p, hsa-miR-454-3p, hsa-miR-454-5p, hsa-miR-4707-3p, hsa-miR-4707-5p, hsa-miR-4755-3p, hsa-miR-4755-5p, hsa-miR-4787-3p, hsa-miR-4787-5p, hsa-miR-483-3p, hsa-miR-483-5p, hsa-miR-484, hsa-miR-485-3p, hsa-miR-485-5p, hsa-miR-487b-3p, hsa-miR-487b-5p, hsa-miR-488-3p, hsa-miR-488-5p, hsa-miR-489-3p, hsa-miR-490-3p, hsa-miR-490-5p, hsa-miR-491-3p, hsa-miR-491-5p, hsa-miR-493-3p, hsa-miR-493-5p, hsa-miR-494-3p, hsa-miR-494-5p, hsa-miR-495-3p, hsa-miR-495-5p, hsa-miR-497-3p, hsa-miR-497-5p, hsa-miR-498, hsa-miR-5001-3p, hsa-miR-5001-5p, hsa-miR-500a-3p, hsa-miR-500a-5p, hsa-miR-5010-3p, hsa-miR-5010-5p, hsa-miR-503-3p, hsa-miR-503-5p, hsa-miR-504-3p, hsa-miR-504-5p, hsa-miR-505-3p, hsa-miR-505-5p, hsa-miR-506-3p, hsa-miR-506-5p, hsa-miR-508-3p, hsa-miR-508-5p, hsa-miR-509-3-5p, hsa-miR-509-3p, hsa-miR-509-5p, hsa-miR-510-3p, hsa-miR-510-5p, hsa-miR-512-5p, hsa-miR-513c-3p, hsa-miR-513c-5p, hsa-miR-514a-3p, hsa-miR-514a-5p, hsa-miR-514b-3p, hsa-miR-514b-5p, hsa-miR-516b-5p, hsa-miR-518c-3p, hsa-miR-518f-3p, hsa-miR-5196-3p, hsa-miR-5196-5p, hsa-miR-519a-3p, hsa-miR-519a-5p, hsa-miR-519c-3p, hsa-miR-519e-3p, hsa-miR-520c-3p, hsa-miR-520f-3p, hsa-miR-520g-3p, hsa-miR-520h, hsa-miR-522-3p, hsa-miR-525-5p, hsa-miR-526b-5p, hsa-miR-532-3p, hsa-miR-532-5p, hsa-miR-539-3p, hsa-miR-539-5p, hsa-miR-542-3p, hsa-miR-542-5p, hsa-miR-543, hsa-miR-545-3p, hsa-miR-545-5p, hsa-miR-548a-3p, hsa-miR-548a-5p, hsa-miR-548ar-3p, hsa-miR-548ar-5p, hsa-miR-548b-3p, hsa-miR-548d-3p, hsa-miR-548d-5p, hsa-miR-548e-3p, hsa-miR-548e-5p, hsa-miR-548h-3p, hsa-miR-548h-5p, hsa-miR-548j-3p, hsa-miR-548j-5p, hsa-miR-548o-3p, hsa-miR-548o-5p, hsa-miR-548v, hsa-miR-551b-3p, hsa-miR-551b-5p, hsa-miR-552-3p, hsa-miR-556-3p, hsa-miR-556-5p, hsa-miR-561-3p, hsa-miR-561-5p, hsa-miR-562, hsa-miR-567, hsa-miR-569, hsa-miR-570-3p, hsa-miR-570-5p, hsa-miR-571, hsa-miR-574-3p, hsa-miR-574-5p, hsa-miR-576-3p, hsa-miR-576-5p, hsa-miR-577, hsa-miR-579-3p, hsa-miR-579-5p, hsa-miR-582-3p, hsa-miR-582-5p, hsa-miR-584-3p, hsa-miR-584-5p, hsa-miR-589-3p, hsa-miR-589-5p, hsa-miR-590-3p, hsa-miR-590-5p, hsa-miR-595, hsa-miR-606, hsa-miR-607, hsa-miR-610, hsa-miR-615-3p, hsa-miR-615-5p, hsa-miR-616-3p, hsa-miR-616-5p, hsa-miR-617, hsa-miR-619-5p, hsa-miR-624-3p, hsa-miR-624-5p, hsa-miR-625-3p, hsa-miR-625-5p, hsa-miR-627-3p, hsa-miR-627-5p, hsa-miR-628-3p, hsa-miR-628-5p, hsa-miR-629-3p, hsa-miR-629-5p, hsa-miR-630, hsa-miR-633, hsa-miR-634, hsa-miR-635, hsa-miR-636, hsa-miR-640, hsa-miR-642a-3p, hsa-miR-642a-5p, hsa-miR-643, hsa-miR-645, hsa-miR-648, hsa-miR-6503-3p, hsa-miR-6503-5p, hsa-miR-651-3p, hsa-miR-651-5p, hsa-miR-6511a-3p, hsa-miR-6511a-5p, hsa-miR-652-3p, hsa-miR-652-5p, hsa-miR-653-5p, hsa-miR-654-3p, hsa-miR-654-5p, hsa-miR-657, hsa-miR-659-3p, hsa-miR-660-3p, hsa-miR-660-5p, hsa-miR-664b-3p, hsa-miR-664b-5p, hsa-miR-671-3p, hsa-miR-671-5p, hsa-miR-675-3p, hsa-miR-675-5p, hsa-miR-7-1-3p, hsa-miR-7-5p, hsa-miR-708-3p, hsa-miR-708-5p, hsa-miR-744-3p, hsa-miR-744-5p, hsa-miR-758-3p, hsa-miR- 758-5p, hsa-miR-765, hsa-miR-766-3p, hsa-miR-766-5p, hsa-miR-767-3p, hsa-miR-767-5p, hsa-miR-769-3p, hsa-miR-769-5p, hsa-miR-802, hsa-miR-873-3p, hsa-miR-873-5p, hsa-miR-874-3p, hsa-miR-874-5p, hsa-miR-876-3p, hsa-miR-876-5p, hsa-miR-885-3p, hsa-miR-885-5p, hsa-miR-887-3p, hsa-miR-887-5p, hsa-miR-9-3p, hsa-miR-9-5p, hsa-miR-92a-1-5p, hsa-miR-92a-2-5p, hsa-miR-92a-3p, hsa-miR-92b-3p, hsa-miR-92b-5p, hsa-miR-93-3p, hsa-miR-93-5p, hsa-miR-941, hsa-miR-942-3p, hsa-miR-942-5p, hsa-miR-96-3p, hsa-miR-96-5p, hsa-miR-98-3p, hsa-miR-98-5p, hsa-miR-99a-3p, hsa-miR-99a-5p, hsa-miR-99b-3p, and hsa-miR-99b-5p.

A "siRNA" is a class of double-stranded RNA molecules, which, similar to miRNA, interferes with the expression of specific genes with complementary nucleotide sequences by degrading mRNA after transcription. A siRNA may be 20-25 base pairs (e.g., 20, 21, 22, 23, 24, or 25 base pairs) in length. Typical, siRNA is a synthetic RNA molecule that may be signed to target any target genes of interest.

A "shRNA" an artificial RNA molecule with a tight hairpin turn that can be used to silence target gene expression via RNAi. Expression of shRNA in cells is typically accomplished by delivery of plasmids or through viral or bacterial vectors. shRNA is an advantageous mediator of RNAi in that it has a relatively low rate of degradation and turnover.

In some embodiments, the cleavage site for the RNA cleaver in the RNA transcript of the present disclosure comprises one or more (e.g., 1, 2, 3, 4, 5, 6, 7, 8, 9, 10 or more) target sites for the RNAi molecule.

A "target site for an RNAi molecule (e.g., a microRNA, siRNA, or shRNA)" is a nucleotide sequence that is complementary to a core nucleotide sequence (the sequence that binds to the target) of the RNAi molecule. Naturally, microRNA targeting sites exist in messenger RNAs (mRNA), typically in the 3' untranslated regions of mRNAs. Binding of the microRNA to its target site in via sequence complementarity leads to silencing of an output molecule either via degrading the mRNA or suppressing translation of the mRNA (e.g., as described in Bartel et al., *Cell* 136 (2): 215-33 (2009), incorporated herein by reference) containing the microRNA binding sites. Herein, when microRNA target sites are referred in the context of DNA, it means the nucleotide sequence that encodes the microRNA target sites in the mRNA that is produced from the genetic circuit. Non-limiting, exemplary microRNA and respective target site sequences are provided in Table 3.

In some embodiments, the RNA cleaver is naturally expressed in the context where cleavage-induced transcript stabilizer is used. For example, the cleavage-induced transcript stabilizer may be used in a cell, and the cell naturally expresses any of the RNA cleavers described herein (e.g., microRNA, endoribonuclease, or ribozyme). In some embodiments, the RNA cleaver is not naturally expressed but is provided (e.g., to a cell) via any known methods in the art, e.g., transfection of a microRNA, siRNA, or ribozyme, delivering of a nucleic acid encoding any of the RNA cleavers. Accordingly, in some embodiments, the cleavage-induced transcript stabilizer further comprises a second promoter operably linked to a nucleotide sequence encoding an RNA cleaver that cleaves at the cleavage site in the RNA transcript. In some embodiments, the second promoter may be a constitutive promoter. In some embodiments, the second promoter is an inducible promoter. In some embodiments, the expression of the RNA cleaver is coupled with an upstream signal, e.g., an environment signal or a cellular event, such that the cleavage of the RNA transcript and the expression of the output molecule can be used to "sense" the signal.

As described herein, cleavage of the RNA transcript by the RNA cleaver removes the degradation signal from the RNA transcript, which in turn stabilizes the RNA transcript. However, cleavage of the RNA transcript generates RNA fragments with free and unprotected 3' ends (in the 5' fragment) and 5' ends (in the 3' fragment), which are rapidly degraded if unprotected. The present disclosure further provides strategies of protecting the 5' fragment of the RNA transcript containing the nucleotide sequence encoding the output molecule. In some embodiments, the RNA transcript of the present disclosure further comprises an RNA stabilizer between the nucleotide sequence encoding the output molecule and the cleavage site for the RNA cleaver.

An "RNA stabilizer," refers to an RNA sequence that, when present in an RNA molecule (e.g., at the 5' end or 3' end), protects the RNA molecule from degradation. In some embodiments, the RNA stabilizer sequence forms secondary structures that blocks access of exoribonucleases to the unprotected ends of the RNA molecule. The RNA stabilizer of the present disclosure is at the 3' end of the 5' fragment (the fragment that contains the nucleotide sequence encoding the output molecule) and prevents degradation of the 5' fragment. Non-limiting examples of RNA stabilizers that may be used in accordance with the present disclosure include: synthetic poly-adenylated tails, and stabilizing

TABLE 3

Non-limiting, Exemplary Synthetic microRNA and Target Sites

| microRNA Name | Nucleotide Sequence Encoding microRNA | SEQ ID NO: | Target Sequence | SEQ ID NO: |
|---|---|---|---|---|
| FF3 | TTTGTATTCAGCCCATATCG | 27 | AACGATATGGGCTGAATACAAA | 32 |
| FF4 | TTTAATTAAAGACTTCAAGCG | 28 | CCGCTTGAAGTCTTTAATTAAA | 33 |
| FF5 | TAATTGTCAAATCAGAGTGC | 29 | AAGCACTCTGATTTGACAATTA | 34 |
| FF6 | TTTATGAGGAATCTCTTTGG | 30 | AACCAAAGAGATTCCTCATAAA | 35 |
| T1 | TTCGAAGTATTCCGCGTACG | 31 | CACGTACGCGGAATACTTCGAA | 36 |

RNA triple helix structures such as MALAT1 (e.g., as described in Brown et al., *Nature Structural & Molecular Biology* 21, 633-640, 2014, incorporated herein by reference), MENβ triplex, KSHV PAN triplex, and histone stem loop. The nucleotide sequences of non-limiting, exemplary RNA stabilizer sequences are provided in Table 4.

TABLE 4

Non-limiting, Exemplary RNA Stabilizers

| 3' RNA stabilizer | Nucleotide sequence |
|---|---|
| MALAT1 | GAUUCGUCAGUAGGGUUGUAAAGGUUUUUCUUUUCCUGAGAAAACAA CCUUUUGUUUUCUCAGGUUUUGCUUUUUGGCCUUUCCCUAGCUUUAA AAAAAAAAAAGCAAAA (SEQ ID NO: 37) |
| MENβ triplex | GCCGCCGCAGGUGUUUCUUUUACUGAGUGCAGCCCAUGGCCGCACUC AGGUUUUGCUUUUCACCUUCCCAUCUG (SEQ ID NO: 38) |
| KSHV PAN triplex | GCUGGGUUUUCCUUGUUCGCACCGGACACCUCCAGUGACCAGACGG CAAGGUUUUAUCCCAGU (SEQ ID NO: 39) |
| histone stem loop | AAAAAGGCUCUUUUCAGAGCACCCA (SEQ ID NO: 40) |

The RNA stabilizer stabilizes the RNA fragment containing nucleotide sequence encoding the output molecule, generated by cleavage of the RNA transcript by the RNA cleaver. An RNA fragment is considered to be stabilized when the half-life of the RNA fragment is at least 20% longer with of the RNA stabilizer, compared to without the RNA stabilizer. For example, an RNA fragment is considered to be stabilized when the half-life of the RNA fragment is increased by at least 20%, at least 30%, at least 40%, at least 50%, at least 60%, at least 70%, at least 80%, at least 90%, at least 100%, at least 2-fold, at least 5-fold, at least 10-fold, at least 50-fold, at least 100-fold or more, compared to without the RNA stabilizer. In some embodiments, the half-life of the RNA fragment is increased by 20%, 30%, 40%, 50%, 60%, 70%, 80%, 90%, 100%, 2-fold, 5-fold, 10-fold, 50-fold, 100-fold or more, with the RNA stabilizer, compared to without the RNA stabilizer.

In some embodiments, the stabilizer further contributes to the stabilization of the RNA fragment containing nucleotide sequence encoding the output molecule, generated by cleavage of the RNA transcript by the RNA cleaver. In some embodiments, the half-life of the RNA transcript is increased by at least 30%, with the RNA stabilizer, compared to without the RNA stabilizer. For example, the half-life of the RNA transcript may be increased by at least 30%, at least 40%, at least 50%, at least 60%, at least 70%, at least 80%, at least 90%, at least 100%, at least 2-fold, at least 5-fold, at least 10-fold, at least 50-fold, at least 100-fold or more, with the RNA stabilizer, compared to without the RNA stabilizer. In some embodiments, the half-life of the RNA fragment is increased by 20%, 30%, 40%, 50%, 60%, 70%, 80%, 90%, 100%, 2-fold, 5-fold, 10-fold, 50-fold, 100-fold or more, with the RNA stabilizer, compared to without the RNA stabilizer.

In some embodiments, stabilization of the RNA transcript leads to increased expression of the output molecule. In some embodiments, the expression level of the output molecule is increased by at least 20%, when the degradation signal is cleaved, compared to before it was cleaved. For example, the expression level of the output molecule may be increased by at least 20%, at least 30%, at least 40%, at least 50%, at least 60%, at least 70%, at least 80%, at least 90%, at least 100%, at least 2-fold, at least 5-fold, at least 10-fold, at least 50-fold, at least 100-fold or more, when the degradation signal is cleaved, compared to before it was cleaved. In some embodiments, the expression level of the output molecule is increased by 20%, 30%, 40%, 50%, 60%, 70%, 80%, 90%, 100%, 2-fold, 5-fold, 10-fold, 50-fold, 100-fold or more, when the degradation signal is cleaved, compared to before it was cleaved.

In some embodiments, additional regulatory elements and genetic circuits are added to the cleavage-induced transcript stabilizer described herein to enhance its performance (e.g., sensitivity). For example, the expression of the output molecule may further be repressed by an RNA repressor. An "RNA repressor," as used herein, refers to a protein that inhibits the expression of the output molecule. Inhibition of output molecule expression may be achieved via different methods. For example, one or more (e.g., 1, 2, 3, 4, 5, 6, 7, 8, 9, 10 or more) recognition sites of an RNA binding protein may be placed upstream of and are operably linked to the nucleotide sequence encoding the output molecule, and binding of RNA binding proteins to the recognition sites can block translation. The one or more recognition sites of the RNA binding protein are "operably linked to" the nucleotide sequence encoding the output molecule, when binding of the RNA binding protein to the recognition sites can inhibit the expression of the output molecule.

In some embodiments, the RNA repressor is an RNA binding protein. An "RNA binding protein," as used herein, refers to a protein that binds to an RNA molecule. The binding of an RNA binding protein to RNA may be dependent on the RNA sequence, or the structure of the RNA. As such, the targets sites of the RNA binding protein, may comprise a specific sequence motif, or form a specific structure (e.g., a stem-loop structure). Any RNA binding protein may be used as the RNA repressor of the present disclosure. Non-limiting examples of RNA binding proteins and their respective recognition site sequences are provided in Table 5.

TABLE 5

Non-limiting Examples of RNA Binding Proteins and Target Sites

| RNA binding protein | Amino acid sequence | Gene sequence | Target site sequence |
|---|---|---|---|
| TetR | MSRLDKSKVINSALELLNE VGIEGLTTRKLAQKLGVE QPTLYWHVKNKRALLDA LAIEMLDRHHTHFCPLEGE SWQDFLRNNAKSFRCALL SHRDGAKVHLGTRPTEKQ YETLENQLAFLCQQGFSLE NALYALSAVGHFTLGCVL EDQEHQVAKEERETPTTD SMPPLLRQAIELFDHQGAE PAFLFGLELIICGLEKQLKC ESGS (SEQ ID NO: 41) | ATGTCAAGACTCGACAAGAGCAAGGTGATT AACAGTGCACTGGAACTTCTCAATGAAGTT GGGATCGAGGGGCTGACTACTAGAAAACTC GCACAGAAACTGGGGGTTGAGCAGCCCACC TTGTACTGGCACGTTAAAAACAAAAGGGCC CTGCTGGATGCTCTGGCCATCGAGATGCTGG ATAGGCATCATACCCACTTCTGCCCTCTGGA AGGAGAATCCTGGCAGGATTTCCTTAGAAA CAACGCCAAGTCCTTTCGCTGTGCTCTTCTT AGCCACCGGGATGGTGCTAAAGTCCATCTC GGCACACGACCAACTGAGAAGCAGTACGAA ACTCTCGAGAACCAGCTGGCCTTTCTCTGTC AACAGGGCTTTTCTCTTGAAAACGCCCTGTA CGCACTGAGTGCAGTTGGGCACTTTACACTC GGATGTGTTCTGGAGGACCAAGAACATCAG GTGGCAAAGGAAGAGAGGGAGACCCCTAC GACTGACTCCATGCCCCCTCTCTTGAGGCAG GCAATAGAATTGTTCGACCATCAGGGCGCA GAACCCGCCTTTCTGTTTGGGCTGGAACTGA TTATCTGCGGTCTTGAGAAACAGCTGAAGT GCGAGTCCGGGAGC (SEQ ID NO: 42) | ATCCAGG CAGAGAA AGGTCGA TACGGAC GGAATGT GGTGCC TGGATCA ACAACAA CAAAATC CAGGCAG AGAAAGG TCGATAC GGACGGA ATGTGGT GGCCTGG ATCAACA ACAACAA CACTG (SEQ ID NO: 43) |
| PPR10 | MLPLDSLLLHLTAPAPAPA PAPRRSHQTPTPPHSFLSP DAQVLVLAISSHPLPTLAA FLASRRDELLRADITSLLK ALELSGHWEWALALLRW AGKEGAADASALEMVVR ALGREGQHDAVCALLDET PLPPGSRLDVRAYTTVLH ALSRAGRYERALELFAEL RRQGVAPTLVTYNVVLDV YGRMGRSWPRIVALLDE MRAAGVEPDGFTASTVIA ACCRDGLVDEAVAFFEDL KARGHAPCVVTYNALLQ VFGKAGNYTEALRVLGE MEQNGCQPDAVTYNELA GTYARAGFFEEAAR (SEQ ID NO: 44) | ATGCTCCCCTTGGACAGTCTCCTGCTGCATC TCACCGCCCCCGCCCCGCCCCAGCCCCTGC TCCAAGAAGGTCTCATCAAACGCCGACCCC CCCTCACAGCTTCCTGTCCCCTGATGCTCAG GTGTTGGTACTCGCAATCAGTTCTCACCCTC TGCCTACCCTGGCTGCTTTCCTCGCTAGCAG GCGGGATGAGTTGCTGAGGGCCGATATCAC CTCTCTCCTTAAGGCACTTGAGCTGTCTGGG CACTGGGAATGGGCATTGGCCCTGCTGCGA TGGGCAGGTAAGGAGGGAGCTGCCGATGCT AGCGCTTTGGAGATGGTCGTAAGAGCACTC GGTAGAGAAGGCCAGCATGACGCAGTCTGT GCTCTGCTGGACGAAACTCCATTGCCTCCAG GCAGCAGACTGGACGTACGGGCCTACACCA CCGTGCTTCACGCCCTCTCAAGAGCCGGTAG GTACGAGAGAGCTCTCGAGCTGTTCGCTGA ACTCAGAAGACAGGGCGTGGCCCCAACCTT GGTAACTTATAACGTGGTACTGGACGTCTAC GGCCGAATGGGGAGAAGTTGGCCGCGCATC GTCGCATTGCTCGACGAAATGCGGGCCGCA GGCGTCGAGCCAGATGGGTTTACCGCAAGC ACGGTGATCGCTGCTTGCTGCCGGGATGTT TGGTGGATGAAGCCGTGGCCTTCTTTGAGG ACTTGAAGGCCAGGGGTCACGCACCTTGTG TCGTAACCTATAACGCACTGTTGCAGGTGTT CGGCAAGGCTGGGAATTATACTGAGGCCCT GAGAGTTCTTGGCGAAATGGAGCAGAACGG GTGCCAGCCAGATGCTGTGACATATAATGA GCTGGCCGGAACCTACGCACGCGCCGGCTT CTTTGAGGAGGCCGCCCGGTGTCTGGACAC GATGGCCAGTAAGGGCCTGCTTCCTAACGC ATTCACATACAATACCGTGATGACAGCATA TGGAAATGTGGGGAAGGTCGACGAAGCTCT CGCCCTTTTCGATCAGATGAAAAAGACTGG CTTCGTTCCCAACGTGAACACGTACAACCTG GTCCTGGGGATGCTGGGAAAGAAATCAAGA TTCACGGTAATGTTGGAAATGTTGGGCGAA ATGAGCAGGTCAGGATGTACCCCTAACAGG GTTACTTGGAATACTATGCTCGCTGTGTGTG GAAAGCGAGGGATGGAAGATTACGTGACAC GGGTTCTGGAGGGCATGCGGAGTTGCGGTG TCGAGCTGTCCCGAGACACATACAACACCC TCATCGCTGCTTATGGGAGGTGCGGTAGCC GGACAAATGCTTTTAAGATGTATAACGAAA TGACGTCCGCAGGGTTCACTCCCTGCATCAC TACATATAACGCTCTGCTGAATGTGCTCTCT CGGCAAGGAGACTGGTCCACTGCTCAGTCA ATCGTTTCAAAGATGCGGACTAAGGGCTTT AAGCCCAACGAGCAATCTTACTCACTCCTCC TGCAGTGTTACGCAAAGGGGGGCAATGTGG CAGGAATTGCAGCCATCGAAAACGAAGTTT ACGGGTCCGGCGCTGTTTTCCCATCTTGGGT | ATTGTAT CCTTAAC CATTTCTT TTATTGTA TCCTTAA CCATTTCT T (SEQ ID NO: 46) |

TABLE 5-continued

Non-limiting Examples of RNA Binding Proteins and Target Sites

| RNA binding protein | Amino acid sequence | Gene sequence | Target site sequence |
|---|---|---|---|
| | | GATCCTGAGGACTCTTGTAATCGCTAATTTC AAATGTCGCCGCTTGGACGGCATGGAAACT GCTTTCCAGGAGGTAAAGGCCAGGGGGTAT AATCCTGATTTGGTGATATTCAACTCAATGC TTTCCATCTACGCTAAGAATGGTATGTATAG CAAAGCAACTGAGGTCTTCGACTCAATTAA GAGGTCAGGTCTGTCCCCAGACCTTATAACT TACAATTCCTTGATGGATATGTATGCCAAGT GTAGCGAGTCCTGGGAAGCTGAAAAGATTC TTAATCAGCTGAAATGTTCCCAGACTATGAA GCCCGATGTTGTTAGCTATAATACAGTTATC AACGGATTCTGCAAACAGGGCCTTGTGAAA GAAGCCCAGAGAGTGCTGTCCGAAATGGTC GCCGACGGCATGGCTCCTTGCGCTGTGACCT ACCATACATTGGTCGGCGGCTATTCCTCTCT CGAGATGTTCTCCGAGGCCAGGGAGGTCAT CGGCTACATGGTGCAACATGGACTGAAACC TATGGAACTGACCTATAGGAGGGTGGTGGA ATCATACTGCAGAGCCAAGCGATTCGAGGA AGCTCGGGGTTTCCTGTCCGAAGTGTCTGAG ACTGATCTGGACTTCGACAAAAAAGCTTTG GAAGCATACATCGAGGACGCTCAATTTGGG CGCTA (SEQ ID NO: 45) | |
| MS2CP | MASNFTQFVLVDNGGTG DVTVAPSNFANGVAEWIS SNSRSQAYKVTCSVRQSS AQKRKYTIKVEVPKVATQ TVGGEELPVAGWRSYLN MELTIPIFATNSDCELIVKA MQGLLKDGNPIPSAIAANS GIY (SEQ ID NO: 47) | ATGGCTTCTAACTTTACTCAGTTCGTTCTCG TCGACAATGGCGGAACTGGCGACGTGACTG TCGCCCCAAGCAACTTCGCTAACGGGGTCG CTGAATGGATCAGCTCTAACTCGCGTTCACA GGCTTACAAAGTAACCTGTAGCGTTCGTCA GAGCTCTGCGCAGAAGCGCAAATACACCAT CAAAGTCGAGGTGCCTAAAGTGGCAACCCA GACTGTTGGTGGTGAGGAGCTTCCTGTAGCC GGTTGGCGTTCGTACTTAAATATGGAACTAA CCATTCCAATTTTCGCCACGAATTCCGACTG CGAGCTTATTGTTAAGGCAATGCAAGGCCT CCTAAAAGATGGAAACCCGATTCCCTCGGC CATCGCAGCAAACTCCGGCATCTAC (SEQ ID NO: 48) | ACATGAG GATCACC CATGTCT GCAGGTC GACTCTA GAAAACA TGAGGAT CACCCAT GTCCTGC AGGTCGA CTCTAGA AA (SEQ ID NO: 49) |
| L7Ae | MYVRFEVPEDMQNEALSL LEKVRESGKVKKGTNETT KAVERGLAKLVYIAEDVD PPEIVAHLPLLCEEKNVPYI YVKSKNDLGRAVGIEVPC ASAAIINEGELRKELGSLV EKIKGLQK (SEQ ID NO: 50) | ATGTACGTGAGATTTGAGGTTCCTGAGGAC ATGCAGAACGAAGCTCTGAGTCTGCTGGAG AAGGTTAGGGAGAGCGGTAAGGTAAAGAA AGGTACCAACGAGACGACAAAGGCTGTGGA GAGGGGACTGGCAAAGCTCGTTTACATCGC AGAGGATGTTGACCCGCCTGAGATCGTTGC TCATCTGCCCCTCCTCTGCGAGGAGAAGAAT GTGCCGTACATTTACGTTAAAAGCAAGAAC GACCTTGGAAGGGCTGTGGGCATTGAGGTG CCATGCGCTTCGGCAGCGATAATCAACGAG GGAGAGCTGAGAAAGGAGCTTGGAAGCCTT GTGGAGAAGATTAAAGGCCTTCAGAAG (SEQ ID NO: 51) | GGGCGTG ATCCGAA AGGTGAC CCGGATC TGGGGCG TGATCCG AAAGGTG ACCCGGA TCCACCG GTC (SEQ ID NO: 52) |

In some embodiments, to repress translation, the recognition sites of RNA binding proteins are placed upstream of the coding sequence. For example, in some embodiments, the one or more (e.g., 1, 2, 3, 4, 5, 6, 7, 8, 9, 10 or more) recognition sites of the RNA binding protein is placed immediately upstream (no spacer between them) of the nucleotide sequence encoding the output molecule. The start of the coding sequence is marked by a start codon, usually AUG. In some embodiments, the one or more (e.g., 1, 2, 3, 4, 5, 6, 7, 8, 9, 10 or more) recognition sites of the RNA binding protein is placed upstream of the nucleotide sequence encoding the output molecule and is separated by a ribonucleotide spacer. The ribonucleotide spacer may be 2-30 nucleotides long. For example, the ribonucleotide spacer may be 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides long). Shorter and longer ribonucleotide spacers may also be used. In some embodiments, the binding of RNA binding proteins to the recognition sites blocks translation. In some embodiments, translation is blocked via inhibition of translation initiation.

In some embodiments, the RNA repressor is fused to a modifying domain. A "modifying domain" as used herein, refers to a protein or polypeptide, or a functional domain thereof, that is capable of modifying a ribonucleoprotein complex formed between the RNA molecule and the RNA binding protein. The modification may be to the ribonucleotide bases (with or without changing the ribonucleotide sequence), to the structure of the RNA molecule containing the RNA binding protein target sites, or the remodeling of the ribonucleoprotein complex. Such modifying domains have been described in the art. For example, Cooke et al. (*J*

Biol Chem. 285(37): 28506-28513, 2010, incorporated herein by reference) describes a CCR4-CAF1-NOT deadenylation complex that, when associated with RNA binding proteins, represses translation in mammalian cells. Cooke further demonstrates that CAF1 (also known as CNOT7) represses translation independent of deadenylation. In another example, Weston et al. (*Nucleic Acids Res.* 34(10): 3082-3094, 2006, incorporated herein by reference) demonstrates that DEAD-box RNA helicase family proteins (e.g., DDX6, Xp54, etc.) play key roles in mRNA degradation and in earlier remodeling of messenger ribonucleoprotein complexes during translation initiation. Accordingly, in some embodiments, the RNA binding protein is fused to a CNOT7 protein. In some embodiments, the RNA binding protein is fused a DEAD-box RNA helicase protein (e.g., DDX6, or Xp54). The amino acid and nucleotide sequences of non-limiting, exemplary modifying domains are provided in Table 6.

TABLE 6

Non-limiting, Exemplary Modifying Domains for Translation Repression

| Modifying domain | Amino acid sequence | Nucleotide sequence (cDNA) |
|---|---|---|
| CNOT7 | MPAATVDHSQRICEVWACN LDEEMKKIRQVIRKYNYVA MDTEFPGVVARPIGEFRSNA DYQYQLLRCNVDLLKIIQLG LTFMNEQGEYPPGTSTWQF NFKFNLTEDMYAQDSIELLT TSGIQFKKHEEEGIETQYFAE LLMTSGVVLCEGVKWLSFH SGYDFGYLIKILTNSNLPEEE LDFFEILRLFFPVIYDVKYLM KSCKNLKGGLQEVAEQLEL ERIGPQHQAGSDSLLTGMAF FKMREMFFEDHIDDAKYCG HLYGLGSGSSYVQNGTGNA YEEEANKQSV (SEQ ID NO: 53) | ATGCCAGCGGCAACTGTAGATCATAGCCAAAGAATT TGTGAAGTTTGGGCTTGCAACTTGGATGAAGAGATG AAGAAAATTCGTCAAGTTATCCGAAAATATAATTAC GTTGCTATGGACACCGAGTTTCCAGGTGTGGTTGCA AGACCCATTGGAGAATTCAGGAGCAATGCTGACTAT CAATACCAACTATTGCGGTGTAATGTAGACTTGTTAA AGATAATTCAGCTAGGACTGACATTTATGAATGAGC AAGGAGAATACCCTCCAGGAACTTCAACTTGGCAGT TTAATTTTAAATTTAATTTGACGGAGGACATGTATGC CCAGGACTCTATAGAGCTACTAACAACATCTGGTAT CCAGTTTAAAAAACATGAGGAGGAAGGAATTGAAA CCCAGTACTTTGCAGAACTTCTTATGACTTCTGGAGT GGTCCTCTGTGAAGGGGTCAAATGGTTGTCATTTCAT AGCGGTTACGACTTTGGCTACTTAATCAAAATCCTAA CCAACTCTAACTTGCCTGAAGAAGAACTTGACTTCTT TGAGATCCTTCGATTGTTTTTTCCTGTCATTTATGATG TGAAGTACCTCATGAAGAGCTGCAAAAATCTCAAAG GTGGATTACAGGAGGTGGCAGAACAGTTAGAGCTGG AACGGATAGGACCACAACATCAGGCAGGATCTGATT CATTGCTCACAGGAATGGCCTTTTTCAAAATGAGAG AAATGTTCTTTGAAGATCATATTGATGATGCCAAATA TTGTGGTCATTTGTATGGCCTTGGTTCTGGTTCATCCT ATGTACAGAATGGCACAGGGAATGCATATGAAGAG GAAGCCAACAAGCAGTCAGTT (SEQ ID NO: 54) |
| DDX6 | MSTARTENPVIMGLSSQNGQ LRGPVKASAGPGGGGTQPQ PQLNQLKNTSTINNGTPQQA QSMAATIKPGDDWKKTLKL PPKDLRIKTSDVTSTKGNEFE DYCLKRELLMGIFEMGWEK PSPIQEESIPIALSGRDILARA KNGTGKSGAYLIPLLERLDL KKDNIQAMVIVPTRELALQV SQICIQVSKHMGGAKVMAT TGGTNLRDDIMRLDDTVHV VIATPGRILDLIKKGVAKVD HVQMIVLDEADKLLSQDFV QIMEDIILTLPKNRQILLYSA TFPLSVQKFMNSHLQKPYEI NLMEELTLKGVTQYYAYVT ERQKVHCLNTLFSRLQINQSI IFCNSSQRVELLAKKISQLGY SCFYIHAKMRQEHRNRVFH DFRNGLCRNLVCTDLFTRGI DIQAVNVVINFDFPKLAETY LHRIGRSGRFGHLGLAINLIT YDDRFNLKSIEEQLGTEIKPI PSNIDKSLYVAEYHSEPAED EKP (SEQ ID NO: 55) | ATGAGCACAGCTCGCACCGAGAACCCGGTGATTATG GGCCTGTCCAGCCAGAACGGACAGCTCAGAGGGCCT GTAAAGGCTTCAGCAGGCCCCGGCGGAGGCGGCACA CAACCACAACCACAGCTTAATCAGCTTAAGAATACT AGCACTATTAATAACGGAACACCGCAGCAGGCCCAA AGCATGGCTGCCACAATTAAACCCGGAGATGACTGG AAGAAGACCCTGAAGCTCCCTCCAAAAGATCTCAGG ATTAAAACTAGCGATGTTACTTCAACAAAGGGAAAT GAGTTCGAAGACTACTGTCTGAAGCGAGAGTTGCTG ATGGGGATTTTCGAAATGGGCTGGGAGAAGCCCTCT CCTATTCAAGAAGAGAGCATCCCCATCGCTCTGTCC GGGAGGGACATCCTTGCCAGGGCTAAAAATGGGACC GGAAAATCAGGAGCTTACTTGATCCCACTCCTTGAA AGGCTTGATCTCAAGAAGGACAACATCCAAGCTATG GTTATCGTGCCAACTAGAGAACTCGCCCTCCAGGTC AGCCAGATTTGCATCCAGGTGAGTAAGCACATGGGC GGAGCTAAGGTGATGGCTACAACTGGAGGGACTAAC CTGCGAGACGACATAATGAGACTTGATGACACAGTC CATGTGGTCATCGCTACACCTGGGAGGATTCTGGAT CTGATCAAAAAAGGAGTGGCAAAGGTGGATCATGTG CAGATGATAGTCTTGGACGAGGCCGACAAACTGCTG AGCCAAGACTTTGTGCAGATCATGGAGGATATCATC TTGACACTCCCCAAGAACCGACAGATTCTGCTGTACT CCGCAACATTTCCTCTTTCCGTTCAGAAATTCATGAA CTCCACATCTCCAGAAACCTTATGAGATCAATTTGATG GAAGAACTGACACTGAAGGGCGTGACCCAGTATTAT GCCTACGTTACTGAGAGGCAAAAGGTCCACTGCCTG AATACTCTCTTCTCCAGGCTCCAGATCAACCAGTCTA TCATCTTTTGCAATAGCTCCCAGCGAGTCGAGCTGCT GGCTAAGAAGATCTCACAGCTTGGATATTCCTGTTTC TACATCCATGCTAAGATGAGACAAGAGCACAGAAAC CGCGTCTTTCATGATTTCCGGAACGGACTCTGTCGCA ACCTGGTTTGCACAGATCTTTTTACTAGAGGCATCGA TATCCAAGCAGTGAACGTGGTTATCAACTTCGACTTT CCCAAACTCGCCGAGACTTATCTTCATAGAATTGGCC GATCCGGTAGGTTTGGGCACCTGGGGCTCGCCATCA ATCTCATTACGTATGATGATAGGTTCAACCTCAAGTC AATAGAAGAGCAGTTGGGGACCGAGATCAAACCAA |

TABLE 6-continued

Non-limiting, Exemplary Modifying Domains for Translation Repression

| Modifying domain | Amino acid sequence | Nucleotide sequence (cDNA) |
|---|---|---|
| | | TCCCGAGCAATATTGACAAATCACTCTATGTGGCCG AATACCATTCAGAGCCTGCCGAGGATGAGAAGCCT (SEQ ID NO: 56) |

In some embodiments, the expression of the output molecule is considered to be "repressed" by the RNA repressor if the expression of the gene is at least 20% lower in the presence of the RNA repressor, compared to without the RNA repressor. For example, the expression of the output molecule is considered to be repressed by the RNA repressor if the expression of the genes is at least 20%, at least 30%, at least 40%, at least 50%, at least 60%, at least 70%, at least 80%, at least 90%, at least 95%, at least 99% or lower in the presence of the RNA repressor, compared to without the RNA repressor. In some embodiments, the expression of the output molecule is considered to be repressed by the RNA repressor if the expression of the genes is 20%, 30%, 40%, 50%, 60%, 70%, 80%, 90%, 95%, 99%, or even 100% in the presence of the RNA repressor, compared to without the RNA repressor.

In some embodiments, expression of the RNA repressor can be controlled by the RNA cleaver, e.g., by incorporating one or more (e.g., 1, 2, 3, 4, 5, 6, 7, 8, 9, 10 or more) cleavage sites for the RNA cleaver into the transcript encoding the RNA repressor. The RNA cleaver cleaves at the cleavage sites, leading to the degradation of the transcript encoding the RNA repressor and no expression of the RNA repressor.

In the absence of the RNA cleaver ("off" state), the RNA transcript encoding the output molecule is degraded, and the RNA repressor expresses, further repressing the expression of the output molecule. This leads to very low or no expression of the output molecule. Conversely, in the presence of the RNA cleaver ("on" state), the transcript encoding the RNA repressor is cleaved and degraded, leading to no expression of the RNA repressor. Further, the RNA cleaver removes the degradation signal from the RNA transcript encoding the output molecule, stabilizing the RNA transcript and allowing expression of the output molecule. In the absence of the RNA repressor, the translation of the output molecule is not repressed, further ensuring its expression. In some embodiments, the level of the RNA repressor may be modulated (e.g., by modulating the strength of the promoter that controls its expression) such that the threshold of the cleavage-induced transcript stabilizer is modulated, allowing it to detect a range of RNA cleaving activities.

An "output molecule," as used herein, refers to a signal produced by the cleavage-induced transcript stabilizer in the presence of the RNA cleaver. In some embodiments, the output molecule has a basal expression level and the expression level increases (e.g., by at least 20%) when an RNA cleaver is present, compared to when the RNA cleaver is not present. For example, the expression level of the output molecule may be at least 20%, at least 30%, at least 40%, at least 50%, at least 60%, at least 70%, at least 80%, at least 90%, at least 100%, at least 2-fold, at least 5-fold, at least 10-fold, at least 100-fold, at least 1000-fold, or higher when the RNA cleaver is present, compared to when the RNA cleaver is not present. In some embodiments, the expression level of the output molecule is 20%, 30%, 40%, 50%, 60%, 70%, 80%, 90%, 100%, 2-fold, 5-fold, 10-fold, 100-fold, 1000-fold, or higher when an RNA cleaver is present, compared to when the RNA cleaver is not present.

The output molecule, in some embodiments, is a detectable protein. In some embodiments, a detectable protein is a fluorescent protein. A fluorescent protein is a protein that emits a fluorescent light when exposed to a light source at an appropriate wavelength (e.g., light in the blue or ultraviolet range). Suitable fluorescent proteins that may be used in accordance with the present disclosure include, without limitation, eGFP, eYFP, eCFP, mKate2, mCherry, mPlum, mGrape2, mRaspberry, mGrape1, mStrawberry, mTangerine, mBanana, and mHoneydew. In some embodiments, a detectable protein is an enzyme that hydrolyzes an substrate to produce a detectable signal (e.g., a chemiluminescent signal). Such enzymes include, without limitation, beta-galactosidase (encoded by LacZ), horseradish peroxidase, or luciferase. In some embodiments, the output molecule is a fluorescent RNA. A fluorescent RNA is an RNA aptamer that emits a fluorescent light when bound to a fluorophore and exposed to a light source at an appropriate wavelength (e.g., light in the blue or ultraviolet range). Suitable fluorescent RNAs that may be used as an output molecule in the sensor circuit of the present disclosure include, without limitation, Spinach and Broccoli (e.g., as described in Paige et al., Science Vol. 333, Issue 6042, pp. 642-646, 2011, incorporated herein by reference).

In some embodiments, the output molecule is a therapeutic molecule. A "therapeutic molecule" is a molecule that has therapeutic effects on a disease or condition, and may be used to treat a diseases or condition. Therapeutic molecules of the present disclosure may be nucleic acid-based or protein or polypeptide-based.

In some embodiments, nucleic acid-based therapeutic molecule may be an RNA interference (RNAi) molecule (e.g., a microRNA, siRNA, or shRNA) or an nucleic acid enzyme (e.g., a ribozyme). RNAi molecules and there use in silencing gene expression are familiar to those skilled in the art. In some embodiments, the RNAi molecule targets an oncogene. An oncogene is a gene that in certain circumstances can transform a cell into a tumor cell. An oncogene may be a gene encoding a growth factor or mitogen (e.g., c-Sis), a receptor tyrosine kinase (e.g., EGFR, PDGFR, VEGFR, or HER2/neu), a cytoplasmic tyrosine kinase (e.g., Src family kinases, Syk-ZAP-70 family kinases, or BTK family kinases), a cytoplasmic serine/threonine kinase or their regulatory subunits (e.g., Raf kinase or cyclin-dependent kinase), a regulatory GTPase (e.g., Ras), or a transcription factor (e.g., Myc). In some embodiments, the oligonucleotide targets Lipocalin (Lcn2) (e.g., a Lcn2 siRNA). One skilled in the art is familiar with genes that may be targeted for the treatment of cancer.

Non-limiting examples of protein or polypeptide-based therapeutic molecules include enzymes, regulatory proteins (e.g., immuno-regulatory proteins), antigens, antibodies or antibody fragments, and structural proteins. In some embodiments, the protein or polypeptide-based therapeutic molecules are for cancer therapy.

Suitable enzymes (for operably linking to a synthetic promoter) for some embodiments of this disclosure include, for example, oxidoreductases, transferases, polymerases, hydrolases, lyases, synthases, isomerases, and ligases, digestive enzymes (e.g., proteases, lipases, carbohydrases, and nucleases). In some embodiments, the enzyme is selected from the group consisting of lactase, beta-galactosidase, a pancreatic enzyme, an oil-degrading enzyme, mucinase, cellulase, isomaltase, alginase, digestive lipases (e.g., lingual lipase, pancreatic lipase, phospholipase), amylases, cellulases, lysozyme, proteases (e.g., pepsin, trypsin, chymotrypsin, carboxypeptidase, elastase), esterases (e.g. sterol esterase), disaccharidases (e.g., sucrase, lactase, beta-galactosidase, maltase, isomaltase), DNases, and RNases.

Non-limiting examples of antibodies and fragments thereof include: bevacizumab (AVASTIN®), trastuzumab (HERCEPTIN®), alemtuzumab (CAMPATH®, indicated for B cell chronic lymphocytic leukemia), gemtuzumab (MYLOTARG®, hP67.6, anti-CD33, indicated for leukemia such as acute myeloid leukemia), rituximab (RITUXAN®), tositumomab (BEXXAR®, anti-CD20, indicated for B cell malignancy), MDX-210 (bispecific antibody that binds simultaneously to HER-2/neu oncogene protein product and type I Fc receptors for immunoglobulin G (IgG) (Fc gamma RI)), oregovomab (OVAREX®, indicated for ovarian cancer), edrecolomab (PANOREX®), daclizumab (ZENAPAX®), palivizumab (SYNAGIS®, indicated for respiratory conditions such as RSV infection), ibritumomab tiuxetan (ZEVALIN®, indicated for Non-Hodgkin's lymphoma), cetuximab (ERBITUX®), MDX-447, MDX-22, MDX-220 (anti-TAG-72), IOR-C5, IOR-T6 (anti-CD1), IOR EGF/R3, celogovab (ONCOSCINT® OV103), epratuzumab (LYMPHOCIDE®), pemtumomab (THERAGYN®), Gliomab-H (indicated for brain cancer, melanoma). In some embodiments, the antibody is an antibody that inhibits an immune check point protein, e.g., an anti-PD-1 antibody such as pembrolizumab (Keytruda®) or nivolumab (Opdivo®), or an anti-CTLA-4 antibody such as ipilimumab (Yervoy®). Other antibodies and antibody fragments may be operably linked to a synthetic promoter, as provided herein.

A regulatory protein may be, in some embodiments, a transcription factor or a immunoregulatory protein. Non-limiting, exemplary transcriptional factors include: those of the NFkB family, such as Rel-A, c-Rel, Rel-B, p50 and p52; those of the AP-1 family, such as Fos, FosB, Fra-1, Fra-2, Jun, JunB and JunD; ATF; CREB; STAT-1, -2, -3, -4, -5 and -6; NFAT-1, -2 and -4; MAF; Thyroid Factor; IRF; Oct-1 and -2; NF-Y; Egr-1; and USF-43, EGR1, Sp1, and E2F1. Other transcription factors may be operably linked to a synthetic promoter, as provided herein.

As used herein, an immunoregulatory protein is a protein that regulates an immune response. Non-limiting examples of immunoregulatory include: antigens, adjuvants (e.g., flagellin, muramyl dipeptide), cytokines including interleukins (e.g., IL-2, IL-7, IL-15 or superagonist/mutant forms of these cytokines), IL-12, IFN-gamma, IFN-alpha, GM-CSF, FLT3-ligand), and immunostimulatory antibodies (e.g., anti-CTLA-4, anti-CD28, anti-CD3, or single chain/antibody fragments of these molecules). Other immunoregulatory proteins may be operably linked to a synthetic promoter, as provided herein.

As used herein, an antigen is a molecule or part of a molecule that is bound by the antigen-binding site of an antibody. In some embodiments, an antigen is a molecule or moiety that, when administered to or expression in the cells of a subject, activates or increases the production of antibodies that specifically bind the antigen. Antigens of pathogens are well known to those of skill in the art and include, but are not limited to parts (coats, capsules, cell walls, flagella, fimbriae, and toxins) of bacteria, viruses, and other microorganisms. Examples of antigens that may be used in accordance with the disclosure include, without limitation, cancer antigens, self-antigens, microbial antigens, allergens and environmental antigens. Other antigens may be operably linked to a synthetic promoter, as provided herein.

In some embodiments, the antigen of the present disclosure is a cancer antigen. A cancer antigen is an antigen that is expressed preferentially by cancer cells (i.e., it is expressed at higher levels in cancer cells than on non-cancer cells) and, in some instances, it is expressed solely by cancer cells. Cancer antigens may be expressed within a cancer cell or on the surface of the cancer cell. Cancer antigens that may be used in accordance with the disclosure include, without limitation, MART-1/Melan-A, gp100, adenosine deaminase-binding protein (ADAbp), FAP, cyclophilin b, colorectal associated antigen (CRC)-C017-1A/GA733, carcinoembryonic antigen (CEA), CAP-1, CAP-2, etv6, AML1, prostate specific antigen (PSA), PSA-1, PSA-2, PSA-3, prostate-specific membrane antigen (PSMA), T cell receptor/CD3-zeta chain and CD20. The cancer antigen may be selected from the group consisting of MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4 and MAGE-C5. The cancer antigen may be selected from the group consisting of GAGE-1, GAGE-2, GAGE-3, GAGE-4, GAGE-5, GAGE-6, GAGE-7, GAGE-8 and GAGE-9. The cancer antigen may be selected from the group consisting of BAGE, RAGE, LAGE-1, NAG, GnT-V, MUM-1, CDK4, tyrosinase, p53, MUC family, HER2/neu, p2iras, RCAS1, α-fetoprotein, E-cadherin, α-catenin, β-catenin, γ-catenin, p120ctn, gp100Pmel117, PRAME, NY-ESO-1, cdc27, adenomatous polyposis coli protein (APC), fodrin, Connexin 37, Ig-idiotype, p15, gp75, GM2 ganglioside, GD2 ganglioside, human papilloma virus proteins, Smad family of tumor antigens, lmp-1, P1A, EBV-encoded nuclear antigen (EBNA)-1, brain glycogen phosphorylase, SSX-1, SSX-2 (HOM-MEL-40), SSX-3, SSX-4, SSX-5, SCP-1 and CT-7, CD20 and c-erbB-2. Other cancer antigens may be operably linked to a synthetic promoter, as provided herein.

In some embodiments, a protein or polypeptide-based therapeutic molecule is a fusion protein. A fusion protein is a protein comprising two heterologous proteins, protein domains, or protein fragments, that are covalently bound to each other, either directly or indirectly (e.g., via a linker), via a peptide bond. In some embodiments, a fusion protein is encoded by a nucleic acid comprising the coding region of a protein in frame with a coding region of an additional protein, without intervening stop codon, thus resulting in the translation of a single protein in which the proteins are fused together.

In some embodiments, the output molecule is a functional molecule. A "function molecule" refers to a molecule that is able to interact with other molecules or circuits to exert a function (e.g., transcription regulation, DNA or RNA cleavage, or any enzymatic activities). Exemplary functional molecules include, without limitation, enzymes (e.g., without limitation, nucleases), transcriptional regulators (e.g., without limitation, activators and repressors), RNAi molecules (e.g., without limitation, siRNA, miRNA, shRNA), and antibodies. In some embodiments, the functional molecule is a nuclease (e.g., a site-specific nuclease such as Csy4, Cas6, CasE, and Cse3). In some embodiments, the functional molecule is a transcriptional repressor (e.g., without limitation, TetR, CNOT7, DDX6, PPR10, and L7Ae). In some embodiments, having a functional molecule as the output molecule of the cleavage-induced transcript stabilizers described herein allows the cleavage-induced transcript stabilizer to further interact with downstream genetic circuits that contain elements responsive to the functional molecule produced by the cleavage-induced transcript stabilizer. Thus, "layering" of genetic circuits can be achieved, allowing multiple levels of complex regulation.

A "promoter" refers to a control region of a nucleic acid sequence at which initiation and rate of transcription of the remainder of a nucleic acid sequence are controlled. A promoter drives expression or drives transcription of the nucleic acid sequence that it regulates. A promoter may also contain sub-regions at which regulatory proteins and molecules may bind, such as RNA polymerase and other transcription factors. Promoters may be constitutive, inducible, activatable, repressible, tissue-specific or any combination thereof. A promoter is considered to be "operably linked" when it is in a correct functional location and orientation in relation to a nucleic acid sequence it regulates to control ("drive") transcriptional initiation and/or expression of that sequence.

A promoter may be one naturally associated with a gene or sequence, as may be obtained by isolating the 5' non-coding sequences located upstream of the coding segment of a given gene or sequence. Such a promoter can be referred to as "endogenous." In some embodiments, a coding nucleic acid sequence may be positioned under the control of a recombinant or heterologous promoter, which refers to a promoter that is not normally associated with the encoded sequence in its natural environment. Such promoters may include promoters of other genes; promoters isolated from any other cell; and synthetic promoters or enhancers that are not "naturally occurring" such as, for example, those that contain different elements of different transcriptional regulatory regions and/or mutations that alter expression through methods of genetic engineering that are known in the art. In addition to producing nucleic acid sequences of promoters and enhancers synthetically, sequences may be produced using recombinant cloning and/or nucleic acid amplification technology, including polymerase chain reaction (PCR) (see U.S. Pat. Nos. 4,683,202 and 5,928,906).

In some embodiments, a promoter is an "inducible promoter," which refer to a promoter that is characterized by regulating (e.g., initiating or activating) transcriptional activity when in the presence of, influenced by or contacted by an inducer signal. An inducer signal may be endogenous or a normally exogenous condition (e.g., light), compound (e.g., chemical or non-chemical compound) or protein that contacts an inducible promoter in such a way as to be active in regulating transcriptional activity from the inducible promoter. Thus, a "signal that regulates transcription" of a nucleic acid refers to an inducer signal that acts on an inducible promoter. A signal that regulates transcription may activate or inactivate transcription, depending on the regulatory system used. Activation of transcription may involve directly acting on a promoter to drive transcription or indirectly acting on a promoter by inactivation a repressor that is preventing the promoter from driving transcription. Conversely, deactivation of transcription may involve directly acting on a promoter to prevent transcription or indirectly acting on a promoter by activating a repressor that then acts on the promoter.

The administration or removal of an inducer signal results in a switch between activation and inactivation of the transcription of the operably linked nucleic acid sequence. Thus, the active state of a promoter operably linked to a nucleic acid sequence refers to the state when the promoter is actively regulating transcription of the nucleic acid sequence (i.e., the linked nucleic acid sequence is expressed). Conversely, the inactive state of a promoter operably linked to a nucleic acid sequence refers to the state when the promoter is not actively regulating transcription of the nucleic acid sequence (i.e., the linked nucleic acid sequence is not expressed).

An inducible promoter of the present disclosure may be induced by (or repressed by) one or more physiological condition(s), such as changes in light, pH, temperature, radiation, osmotic pressure, saline gradients, cell surface binding, and the concentration of one or more extrinsic or intrinsic inducing agent(s). An extrinsic inducer signal or inducing agent may comprise, without limitation, amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones or combinations thereof.

Inducible promoters of the present disclosure include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some embodiments, an inducer signal of the present disclosure is an N-acyl homoserine lactone (AHL), which is a class of signaling molecules involved in bacterial quorum sensing. Quorum sensing is a method of communication between bacteria that enables the coordination of group based behavior based on population density. AHL can diffuse across cell membranes and is stable in growth media over a range of pH values. AHL can bind to transcriptional activators such as LuxR and stimulate transcription from cognate promoters.

In some embodiments, an inducer signal of the present disclosure is anhydrotetracycline (aTc), which is a derivative of tetracycline that exhibits no antibiotic activity and is designed for use with tetracycline-controlled gene expression systems, for example, in bacteria.

In some embodiments, an inducer signal of the present disclosure is isopropyl β-D-1-thiogalactopyranoside (IPTG), which is a molecular mimic of allolactose, a lactose metabolite that triggers transcription of the lac operon, and it is therefore used to induce protein expression where the gene is under the control of the lac operator. IPTG binds to the lac repressor and releases the tetrameric repressor from the lac operator in an allosteric manner, thereby allowing the transcription of genes in the lac operon, such as the gene coding for beta-galactosidase, a hydrolase enzyme that catalyzes the hydrolysis of β-galactosides into monosaccharides. The sulfur (S) atom creates a chemical bond which is non-hydrolyzable by the cell, preventing the cell from metabolizing or degrading the inducer. IPTG is an effective inducer of protein expression, for example, in the concentration range of 100 μM to 1.0 mM. Concentration used depends on the strength of induction required, as well as the genotype of cells or plasmid used. If lacIq, a mutant that over-produces the lac repressor, is present, then a higher concentration of IPTG may be necessary. In blue-white screen, IPTG is used together with X-gal. Blue-white screen allows colonies that have been transformed with the recombinant plasmid rather than a non-recombinant one to be identified in cloning experiments.

Other inducible promoter systems are known in the art and may be used in accordance with the present disclosure.

In some embodiments, inducible promoters of the present disclosure are from prokaryotic cells (e.g., bacterial cells). Examples of inducible promoters for use prokaryotic cells include, without limitation, bacteriophage promoters (e.g. Pls1con, T3, T7, SP6, PL) and bacterial promoters (e.g., Pbad, PmgrB, Ptrc2, Plac/ara, Ptac, Pm), or hybrids thereof (e.g. PLlacO, PLtetO). Examples of bacterial promoters for use in accordance with the present disclosure include, without limitation, positively regulated E. coli promoters such as positively regulated 670 promoters (e.g., inducible pBad/araC promoter, Lux cassette right promoter, modified lambda Prm promoter, plac Or2-62 (positive), pBad/AraC with extra REN sites, pBad, P(Las) TetO, P(Las) CIO, P(Rhl), Pu, FecA, pRE, cadC, hns, pLas, pLux), aS promoters (e.g., Pdps), a32 promoters (e.g., heat shock) and 654 promoters (e.g., glnAp2); negatively regulated E. coli promoters such as negatively regulated 670 promoters (e.g., Promoter (PRM+), TetR—TetR-4C P(Las) TetO, P(Las) CIO, P(Lac) IQ, RecA_DlexO_DLacO1, dapAp, FecA, Pspac-hy, pcI, plux-cI, plux-lac, CinR, CinL, glucose controlled, modified Pr, modified Prm+, FecA, Pcya, rec A (SOS), Rec A (SOS), EmrR_regulated, BetI_regulated, pLa-c_lux, pTet_Lac, pLac/Mnt, pTet/Mnt, LsrA/cI, pLux/cI, LacI, LacIQ, pLacIQ1, pLas/cI, pLas/Lux, pLux/Las, pRecA with LexA binding site, reverse BBa_R0011, pLacI/ara-1, pLacIq, rrnB P1, cadC, hns, PfhuA, pBad/araC, nhaA, OmpF, RcnR), αS promoters (e.g., Lutz-Bujard LacO with alternative sigma factor σ38), σ32 promoters (e.g., Lutz-Bujard LacO with alternative sigma factor σ32), and σ54 promoters (e.g., glnAp2); negatively regulated B. subtilis promoters such as repressible B. subtilis σA promoters (e.g., Gram-positive IPTG-inducible, Xyl, hyper-spank) and aB promoters. Other inducible microbial promoters may be used in accordance with the present disclosure.

The cleavage-induced transcript stabilizer may be included in one or more (e.g., 2, 3 or more) nucleic acid molecules (e.g., vectors) and introduced into a cell. A "nucleic acid" is at least two nucleotides covalently linked together, and in some instances, may contain phosphodiester bonds (e.g., a phosphodiester "backbone"). A nucleic acid may be DNA, both genomic and/or cDNA, RNA or a hybrid, where the nucleic acid contains any combination of deoxyribonucleotides and ribonucleotides (e.g., artificial or natural), and any combination of bases, including uracil, adenine, thymine, cytosine, guanine, inosine, xanthine, hypoxanthine, isocytosine and isoguanine. Nucleic acids of the present disclosure may be produced using standard molecular biology methods (see, e.g., Green and Sambrook, Molecular Cloning, A Laboratory Manual, 2012, Cold Spring Harbor Press).

In some embodiments, nucleic acids are produced using GIBSON ASSEMBLY® Cloning (see, e.g., Gibson, D. G. et al. Nature Methods, 343-345, 2009; and Gibson, D. G. et al. Nature Methods, 901-903, 2010, each of which is incorporated by reference herein). GIBSON ASSEMBLY® typically uses three enzymatic activities in a single-tube reaction: 5' exonuclease, the 3' extension activity of a DNA polymerase and DNA ligase activity. The 5' exonuclease activity chews back the 5' end sequences and exposes the complementary sequence for annealing. The polymerase activity then fills in the gaps on the annealed regions. A DNA ligase then seals the nick and covalently links the DNA fragments together. The overlapping sequence of adjoining fragments is much longer than those used in Golden Gate Assembly, and therefore results in a higher percentage of correct assemblies.

In some embodiments, the cleavage-induced transcript stabilizer are is delivered to a cell a vector. A "vector" refers to a nucleic acid (e.g., DNA) used as a vehicle to artificially carry genetic material (e.g., an engineered nucleic acid) into a cell where, for example, it can be replicated and/or expressed. In some embodiments, a vector is an episomal vector (see, e.g., Van Craenenbroeck K. et al. Eur. J. Biochem. 267, 5665, 2000, incorporated by reference herein). A non-limiting example of a vector is a plasmid. Plasmids are double-stranded generally circular DNA sequences that are capable of automatically replicating in a host cell. Plasmid vectors typically contain an origin of replication that allows for semi-independent replication of the plasmid in the host and also the transgene insert. Plasmids may have more features, including, for example, a "multiple cloning site," which includes nucleotide overhangs for insertion of a nucleic acid insert, and multiple restriction enzyme consensus sites to either side of the insert. Another non-limiting example of a vector is a viral vector (e.g., retroviral, adenoviral, adeno-association, helper-dependent adenoviral systems, hybrid adenoviral systems, herpes simplex, pox virus, lentivirus, Epstein-Barr virus). In some embodiments, the viral vector is derived from an adeno-associated virus (AAV). In some embodiments, the viral vector is derived from an herpes simplex virus (HSV).

The nucleic acids or vectors containing the genetic circuits of the cleavage-induced transcript stabilizer may be delivered to a cell by any methods known in the art for delivering nucleic acids. For example, for delivering nucleic acids to a prokaryotic cell, the methods include, without limitation, transformation, transduction, conjugation, and electroporation. For delivering nucleic acids to a eukaryotic cell, methods include, without limitation, transfection, electroporation, and using viral vectors.

Cells containing the cleavage-induced transcript stabilizer are also provided herein. A "cell" is the basic structural and functional unit of all known independently living organisms. It is the smallest unit of life that is classified as a living thing. Some organisms, such as most bacteria, are unicellular (consist of a single cell). Other organisms, such as humans, are multicellular.

In some embodiments, a cell for use in accordance with the present disclosure is a prokaryotic cell, which may comprise a cell envelope and a cytoplasmic region that contains the cell genome (DNA) and ribosomes and various sorts of inclusions. In some embodiments, the cell is a bacterial cell. As used herein, the term "bacteria" encompasses all variants of bacteria, for example, prokaryotic organisms and cyanobacteria. Bacteria are small (typical linear dimensions of around 1 micron), non-compartmentalized, with circular DNA and ribosomes of 70S. The term bacteria also includes bacterial subdivisions of Eubacteria and Archaebacteria. Eubacteria can be further subdivided into gram-positive and gram-negative Eubacteria, which depend upon a difference in cell wall structure. Also included herein are those classified based on gross morphology alone (e.g., cocci, bacilli). In some embodiments, the bacterial cells are gram-negative cells, and in some embodiments, the bacterial cells are gram-positive cells. Examples of bacterial cells that may be used in accordance with the invention include, without limitation, cells from *Yersinia* spp., *Escherichia* spp., *Klebsiella* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., *Erysipelothrix* spp., *Salmonella* spp., *Stremtomyces* spp. In some embodiments, the bacterial cells are from *Staphylococcus aureus, Bacillus subtilis, Clostridium butyricum, Brevibacterium lactofermentum, Streptococcus agalactiae, Lactococcus lactis, Leuconostoc lactis, Streptomyces, Actinobacillus actinobycetemcomitans, Bacteroides*, cyanobacteria, *Escherichia coli, Helobacter pylori, Selnomonas ruminatium, Shigella sonnei, Zymomonas mobilis, Mycoplasma mycoides, Treponema denticola, Bacillus thuringiensis, Staphylococcus lugdunensis, Leuconostoc oenos, Corynebacterium xerosis, Lactobacillus planta rum, Streptococcus faecalis, Bacillus coagulans, Bacillus ceretus, Bacillus popillae, Synechocystis* strain PCC6803, *Bacillus liquefaciens, Pyrococcus abyssi, Selenomonas nominantium, Lactobacillus hilgardii, Streptococcus ferus, Lactobacillus pentosus, Bacteroides fragilis, Staphylococcus epidermidis, Zymomonas mobilis, Streptomyces phaechromogenes, Streptomyces ghanaenis, Halobacterium* strain GRB, or *Halobaferax* sp. strain Aa2.2.

In some embodiments, a cell for use in accordance with the present disclosure is a eukaryotic cell, which comprises membrane-bound compartments in which specific metabolic activities take place, such as a nucleus. Examples of eukaryotic cells for use in accordance with the invention include, without limitation, mammalian cells, insect cells, yeast cells (e.g., *Saccharomyces cerevisiae*) and plant cells. In some embodiments, the eukaryotic cells are from a vertebrate animal. In some embodiments, the cell is a mammalian cell. In some embodiments, the cell is a human cell. In some embodiments, the cell is from a rodent, such as a mouse or a rat. Examples of vertebrate cells for use in accordance with the present disclosure include, without limitation, reproductive cells including sperm, ova and embryonic cells, and non-reproductive cells, including kidney, lung, spleen, lymphoid, cardiac, gastric, intestinal, pancreatic, muscle, bone, neural, brain and epithelial cells. Stem cells, including embryonic stem cells, can also be used.

In some embodiments, the cell is a diseased cell. A "diseased cell," as used herein, refers to a cell whose biological functionality is abnormal, compared to a non-diseased (normal) cell. In some embodiments, the diseased cell is a cancer cell.

In some embodiments, the cleavage-induced transcript stabilizer is inserted into the genome of the cell. Methods of inserting genetic circuits into the genome of a cell are known to those skilled in the art (e.g., via site-specific recombination, using any of the known genome-editing tools, or using other recombinant DNA technology). In some instances, integrating the cleavage-induced transcript stabilizer into the genome of a cell is advantageous for its applications (e.g., therapeutic application or biomanufacturing application), compared to a cell engineered to simply express a transgene (e.g., via transcription regulation). It is known that genetically engineered cells suffer from epigenetic silencing of the integrated transgene. However, continuous transcription of transgenes helps to prevent their silencing, which is not possible with transcriptionally-regulated gene circuits relying on transcriptional repression. In contrast, the cleavage-induced transcript stabilizer described herein relies on RNA-level regulation and can achieve continuous transcription of the transgenes.

Applications

Further provided herein are the functionality of the cleavage-induced transcript stabilizer and methods of using them. In some embodiments, the methods comprising delivering the cleavage-induced transcript stabilizers described herein into a cell (e.g., by any of the methods described herein and known to one skilled in the art). In some embodiments, the methods comprises maintaining the cell containing the cleavage-induced transcript stabilizer. In some embodiments, the maintaining is carried out under conditions to allow the cleavage-induced transcript stabilizer to function.

In some embodiments, the cleavage-induced transcript stabilizer described herein is used in a method for detecting an RNA cleaver activity (e.g., in a cell). The RNA cleaver may be any RNA cleavers described herein, e.g., an endoribonuclease, an RNAi molecule such as a microRNA, or a ribozyme. In some embodiments, the RNA cleaver is naturally expressed by the cell. In some embodiments, the RNA cleaver is introduced into the cell, e.g., on an expression vector. As described herein, expression of the RNA cleaver leads to the expression of the output molecule. Accordingly, the expression of the output molecule indicates the presence of the RNA cleaver (e.g., in a cell). Thus, in some embodiments, the method for detecting an RNA cleaver activity further comprises detecting the output molecule.

The cleavage-induced transcript stabilizer described herein may be used for a variety of applications. In some embodiments, the cleavage-induced transcript stabilizer is used for diagnostic purposes. The presence of certain RNA cleavers (e.g., microRNAs), in some embodiments, may be used for determining the cell type. For example, diseased cells such as cancer cells may express cancer-cell specific RNA cleavers (e.g., microRNAs). The present disclosure further contemplates the use of the cleavage-induced transcript stabilizer in classifying cell types. For example, the cleavage-induced transcript stabilizer may be designed to detect an RNA cleaver (e.g., microRNA) that is specific to a diseased cell (e.g., cancer cell), and in the presence of the RNA cleaver (e.g., microRNA), the cleavage-induced transcript stabilizer expresses the output molecule. For diagnostic purposes, the output molecules of the cleavage-induced transcript stabilizer is typically a detectable molecule (e.g., a fluorescent protein or chemiluminescent protein). Depending on the specific RNA cleaver (e.g., microRNA) a diseased cell produces, in some embodiments, detection of the output molecule indicates that the cell is a diseased cell (e.g., cancer cell). In some embodiments, the lack of expression of the output molecule indicates a diseased cell.

In another example, the cleavage-induced transcript stabilizer is used for therapeutic purposes. For example, in some embodiments, the cleavage-induced transcript stabilizer is designed to detect an RNA cleaver (e.g., a microRNA) in a diseased cell (e.g., a cancer cell) and to produce an output molecule that is a therapeutic molecule (e.g., a therapeutic protein or RNA). Upon detecting of the RNA cleaver in the diseased cell, the cleavage-induced transcript stabilizer produces the therapeutic molecule, thus treating the disease. Such therapeutic methods are highly specific to the diseased cell and have low impact on healthy cells because the cleavage-induced transcript stabilizer will not detect the RNA cleaver in a healthy cell and thus will not produce the output molecule. Further, the therapeutic effect of the cleavage-induced transcript stabilizer is long lasting. For example, the cleavage-induced transcript stabilizer will continuing to produce the therapeutic molecule until the diseased cell no longer expresses the RNA cleaver that is specific to the disease (e.g., cancer). Once therapeutic effects have taken place, the cleavage-induced transcript stabilizer can sense the change in the expression of the RNA cleaver and stop the production of the therapeutic molecule.

For either diagnostic or treatment purposes, the cell may be in vitro (e.g., cultured cell), ex vivo (e.g., isolated from a subject), or in vivo in a subject. For in vivo applications, in some embodiments, the method comprises administering an effective amount of a composition comprising the cleavage-induced transcript stabilizer described herein to a subject in need thereof. The composition can further comprise additional agents (e.g. for specific delivery, increasing half-life, or other therapeutic agents). In some embodiments, the composition further comprises a pharmaceutically acceptable carrier. The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. A "pharmaceutically acceptable carrier" is a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation.

Some examples of materials which can serve as pharmaceutically-acceptable carriers include, without limitation: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as peptides and amino acids (23) serum component, such as serum albumin, HDL and LDL; (24) C2-C12 alcohols, such as ethanol; and (25) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient," "carrier," "pharmaceutically acceptable carrier" or the like are used interchangeably herein.

An "effective amount" refers to the amount of the cleavage-induced transcript stabilizer or composition comprising such required to confer therapeutic effect on the subject, either alone or in combination with one or more other therapeutic agents. Effective amounts vary, as recognized by those skilled in the art, depending on the particular condition being treated, the severity of the condition, the individual subject parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a subject may insist upon a lower dose or tolerable dose for medical reasons, psychological reasons or for virtually any other reasons.

Empirical considerations, such as the half-life, generally will contribute to the determination of the dosage. Frequency of administration may be determined and adjusted over the course of therapy, and is generally, but not necessarily, based on treatment and/or suppression and/or amelioration and/or delay of a disorder. Alternatively, sustained continuous release formulations of agent may be appropriate. Various formulations and devices for achieving sustained release are known in the art.

An effective amount of the cleavage-induced transcript stabilizer or composition comprising such may be administered repeatedly to a subject (e.g., 2, 3, 4, 5, 6, 7, 8, 9, 10 times or more). In some embodiments, dosage is daily, every other day, every three days, every four days, every five days, or every six days. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the agents used) can vary over time.

In some embodiments, for an adult subject of normal weight, doses ranging from about 0.01 to 1000 mg/kg may be administered. In some embodiments, the dose is between 1 to 200 mg. The particular dosage regimen, i.e., dose, timing and repetition, will depend on the particular subject and that subject's medical history, as well as the properties of the agent (such as the half-life of the agent, and other considerations well known in the art).

For the purpose of the present disclosure, the appropriate dosage of the cleavage-induced transcript stabilizer or compositions comprising such will depend on the specific agent (or compositions thereof) employed, the formulation and route of administration, the type and severity of the disorder, previous therapy, the subject's clinical history and response to the agents, and the discretion of the attending physician. Typically the clinician will administer an agent until a dosage is reached that achieves the desired result. Administration can be continuous or intermittent, depending, for example, upon the recipient's physiological condition, and other factors known to skilled practitioners. The administration of an agent may be essentially continuous over a preselected period of time or may be in a series of spaced dose, e.g., either before, during, or after developing a disorder.

A "subject" refers to human and non-human animals, such as apes, monkeys, horses, cattle, sheep, goats, dogs, cats, rabbits, guinea pigs, rats, and mice. In one embodiment, the subject is human. In some embodiments, the subject is an experimental animal or animal substitute as a disease model. A "subject in need thereof" refers to a subject who has or is at risk of a disease or disorder (e.g., cancer).

The cleavage-induced transcript stabilizer of the present disclosure may be delivered to a subject (e.g., a mammalian subject, such as a human subject) by any in vivo delivery method known in the art. For example, the cleavage-induced transcript stabilizer may be delivered intravenously. In some embodiments, cleavage-induced transcript stabilizer is delivered in a delivery vehicle (e.g., non-liposomal nanoparticle or liposome). In some embodiments, the cleavage-induced transcript stabilizer is delivered systemically to a subject having a cancer or other disease and produces a therapeutic molecule specifically in cancer cells or diseased cells of the subject. In some embodiments, cleavage-induced transcript stabilizer is delivered to a site of the disease or disorder (e.g., site of cancer).

Non-limiting examples of cancers that may be treated using the cleavage-induced transcript stabilizer methods described herein include: premalignant neoplasms, malignant tumors, metastases, or any disease or disorder characterized by uncontrolled cell growth such that it would be considered cancerous or precancerous. The cancer may be a primary or metastatic cancer. Cancers include, but are not limited to, ocular cancer, biliary tract cancer, bladder cancer, pleura cancer, stomach cancer, ovary cancer, meninges cancer, kidney cancer, brain cancer including glioblastomas and medulloblastomas, breast cancer, cervical cancer, choriocarcinoma, colon cancer, endometrial cancer, esophageal cancer, gastric cancer, hematological neoplasms including acute lymphocytic and myelogenous leukemia, multiple myeloma, AIDS-associated leukemias and adult T-cell leukemia lymphoma, intraepithelial neoplasms including Bowen's disease and Paget's disease, liver cancer, lung cancer, lymphomas including Hodgkin's disease and lymphocytic lymphomas, neuroblastomas, oral cancer including squamous cell carcinoma, ovarian cancer including those arising from epithelial cells, stromal cells, germ cells and mesenchymal cells, pancreatic cancer, prostate cancer, rectal cancer, sarcomas including leiomyosarcoma, rhabdomyosarcoma, liposarcoma, fibrosarcoma, and osteosarcoma, skin cancer including melanoma, Kaposi's sarcoma, basocellular cancer, and squamous cell cancer, testicular cancer including germinal tumors such as seminoma, non-seminoma, teratomas, choriocarcinomas, stromal tumors and germ cell tumors, thyroid cancer including thyroid adenocarcinoma and medullar carcinoma, and renal cancer including adenocarcinoma and Wilms' tumor. Commonly encountered cancers include breast, prostate, lung, ovarian, colorectal, and brain cancer. In some embodiments, the tumor is a melanoma, carcinoma, sarcoma, or lymphoma.

EXAMPLES

Example 1: A Signal Inverter Module for RNA Cleavers: Detecting and Evaluating miRNA, Ribozymes, and Ribonucleases Introduction:

Cellular RNAs are processed in many ways; one important mechanism is by RNA cleavage. Cleavage is mediated by several factors including cis- or trans-acting ribozymes and ribonucleases. For example, a well-known factor for regulating expression is through the RNAi pathway: in some instances (i.e. perfect complementarity) miRNA or siRNA targeting can cleave mRNA, which usually leads to rapid degradation of the transcript. This mechanism in particular has been especially useful for the field of synthetic biology for two reasons, (1) miRNAs have been shown to serve as biomarkers since they tend to vary drastically across different cell types and disease states[1] and (2) building sensors for a given miRNA is as straight forward as engineering the complementary sequence into a reporter transcript[2], where the reporter expression is then inversely related to the miRNA level (i.e. a high miRNA level would lead to degradation and low reporter expression). To detect states where miRNAs of interest are low, this is ideal since the reporter transcript will not be targeted and expression will stay high, however sensors to detect miRNAs that are expected to be at high levels are more complex. They usually involve a double-inversion strategy where the miRNA target sites are engineered into a transcript encoding a translational or transcriptional repressor instead, therefore high levels of miRNA targeting leads to low repressor expression and rescues reporter expression. This method has some drawbacks including failure modes cause by time delays, and the requirement of more than one transcriptional unit and transcript. The need for a mechanism to turn on expression in response to RNA cleavage, which would only require one transcript and would therefore avoid these drawbacks, exists. Such a mechanism would likewise find utility in the activity detection of ribonucleases or ribozymes, which typically lead to transcript cleavage and rapid degradation, and would therefore normally result in reporter expression that is inversely proportional to activity. A mechanism to turn reporter expression "ON" instead of "OFF" in response to RNA cleavage would enable monitoring of in vivo activity of these species in varying contexts, something which is poorly understood.

Herein a novel module that can be added to transgenes to induce expression upon an RNA cleavage event is described. This allows for the inversion of signal and also a monitoring of cleavage activity where increased output indicates increased activity. The transgene may be a fluorescent protein for direct reporting or another protein to link to downstream genetic logic or therapeutic output.

Figure 1B:
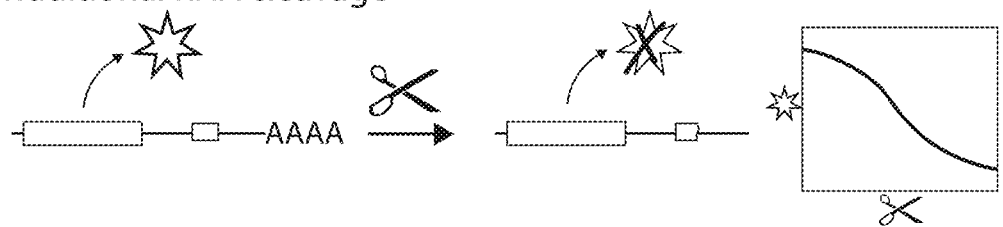
Figure 1B:
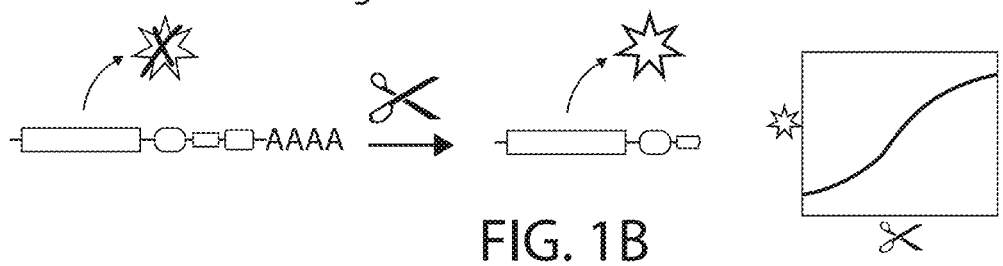

Design:

As depicted in FIG. 1A, this novel signal inverter relies on the ability to cleave a degradation signal from the 3' end of a transcript. The cleavage product would be stable and could be translated to produce a protein of interest. Therefore, in the absence of the RNA cleaver or when the cleaver is inactive, the entire transcript is targeted for rapid degradation leading to low output expression. When the RNA cleaver is present or active the degradation signal is removed allowing for transgene expression due to an upstream stabilizer that prevents transcript degradation in the absence of a poly-A tail. This module will reverse the logic of an RNA cleaver that normally results in transcript degradation and inversely proportional transgene expression to one that results in transcript stabilization after cleavage (FIG. 1B).

Degradation Signal Selection

The degradation signal should be potent enough to decrease expression levels substantially and should ideally function without the need of another synthetic unit. A short 8-nt segment discovered by Geissler et. al.[3] is present in many endogenous transcripts across many mammalian cell types and is shown to bind hnRNPs which recruit deadenylases to degrade the transcript. To ensure maximum repression these signals were repeated in the 3'UR of a reporter transcript.

Stabilizer Selection

The stabilizer portion of this module should act to stabilize the transcript once cleaved. It should not inhibit degradation via the signals mentioned above in the absence of cleavage and once the transcript is cleaved, translation should be facilitated. A triple helix structure has been shown to stabilize the 3' end of transcripts that lack a poly-A tail[4]. When appended to the end of mRNAs, translation was facilitated with high expression. Additionally, it has been shown to stabilize transcripts after Csy4 cleavage.

Ultrasensitive Switch

Figure 2:
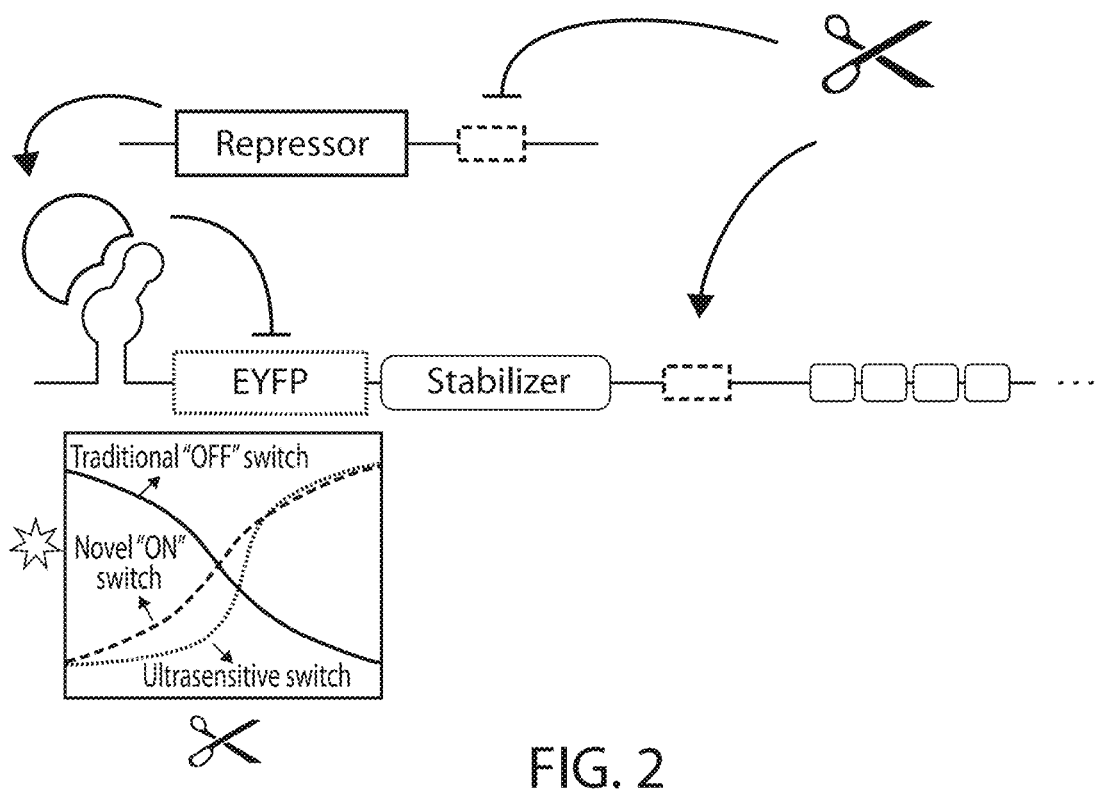
FIG. 2: Ultrasensitive switch schematic. Two separate RNA transcripts are shown. A traditional "off" switch controls the expression of an RNA repressor that represses the output molecule. The output molecule is encoded by an RNA transcript that incorporates the "on" switch described herein. The combined effect of the two switches are also shown.

A typical cleavage "OFF" switch can control the expression of a translational repressor where expression is inversely proportional to the cleaver; this new cleavage "ON" switch controls the expression of an output protein proportionally to the cleaver activity. Therefore, as depicted in FIG. 2, an ultrasensitive cleavage "ON" switch can be achieved by introducing these switches at different levels of a cascades. A cleavage "ON" switch, as described herein, can be added to an output transgene while a cleavage "OFF" switch can be added to a repressor of the transgene. In the absence of the RNA cleaver, transgene expression remains low both because expression is blocked by the repressor and the degradation domains signal transcript degradation. However, in the presence of the cleaver, the repressor transcript is cleaved, relieving the expression inhibition while the degradation domains on the output transcript are also removed to rescue expression. By changing the level of the repressor component, it is possible to modulate the threshold of the ultrasensitive switch to enable a more digital response.

Figure 3A:
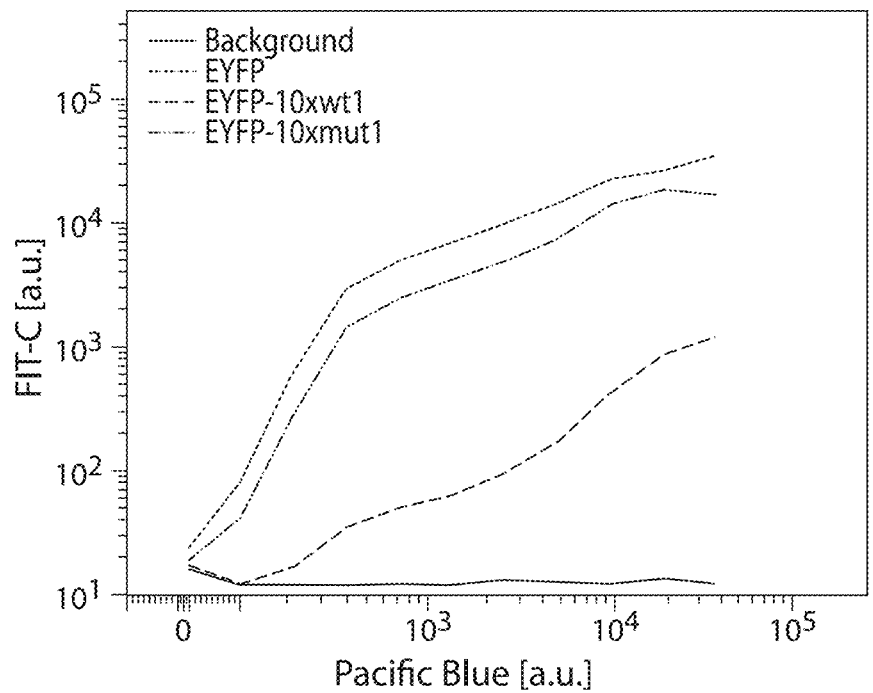
FIGS. 3A-3D: Degradation signals and stabilizers. Solid lines and bars indicate constructs that do not contain the triplex sequence, while dashed lines or bars do contain the triplex sequence.
Figure 3B:
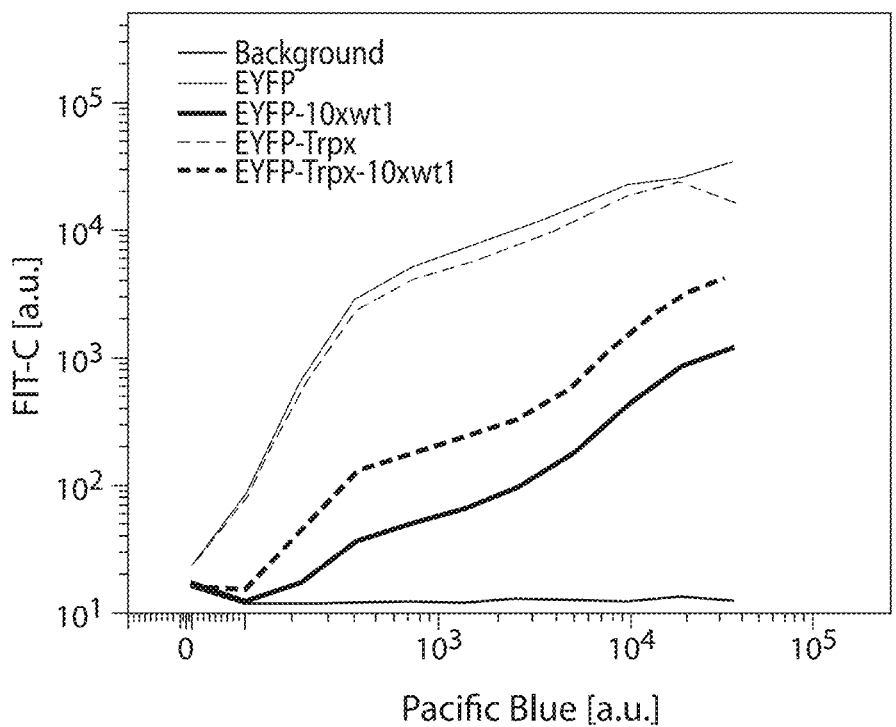
Figure 3C:
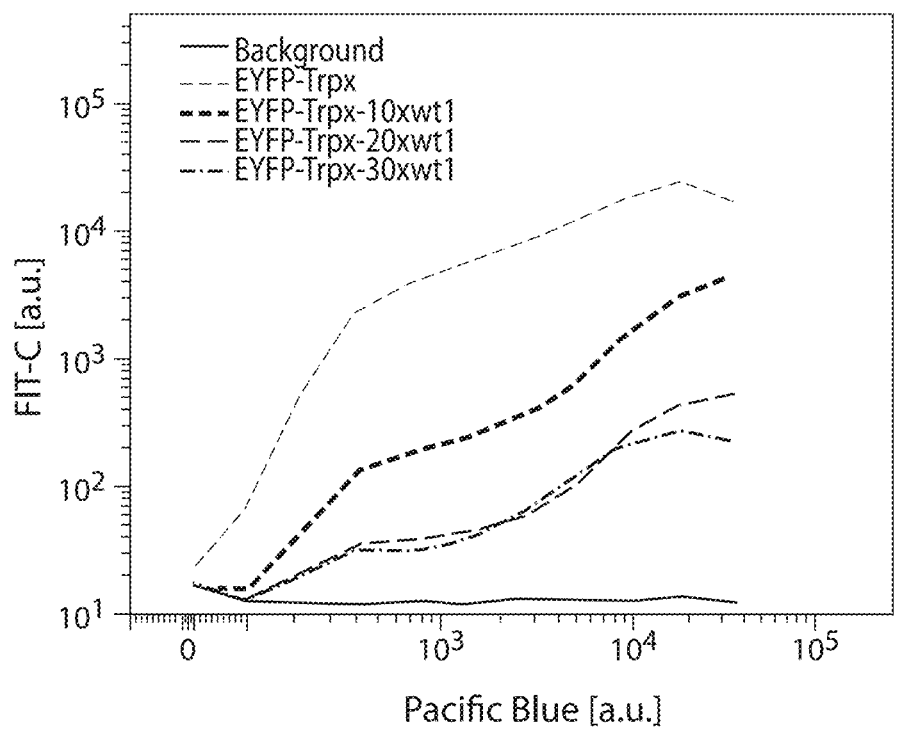
Figure 3D:
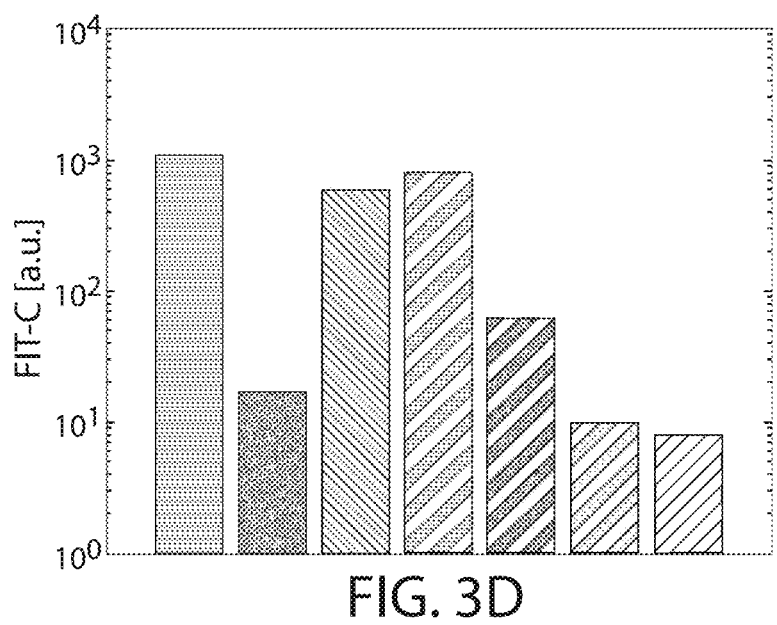

Results:

When 10 copies of the Geissler degradation sequence were cloned into the 3'UTR after the CDS of EYFP driven by a constitutive CMV promoter, expression was 24 fold less than the same construct with 10 repeated copies of a mutated version of this sequence and 42 fold less than a constitutive EYFP (see FIGS. 3A and 3D).

The triplex sequence was cloned after EYFP CDS. As seen in FIG. 3B, the EYFP-triplex construct expressed highly, while adding 10 repeats of the Geissler degradation sequence after the triplex enabled knock-down (FIGS. 3B and 3D). When additional repeats of the Geissler degradation sequence were added after the triplex, expression was further decreased, with 30×repeat performing best enabling a 125 fold decrease compared to constitutive EYFP (see FIGS. 3C and 3D).

Ribonuclease Inverter

Figure 4A:
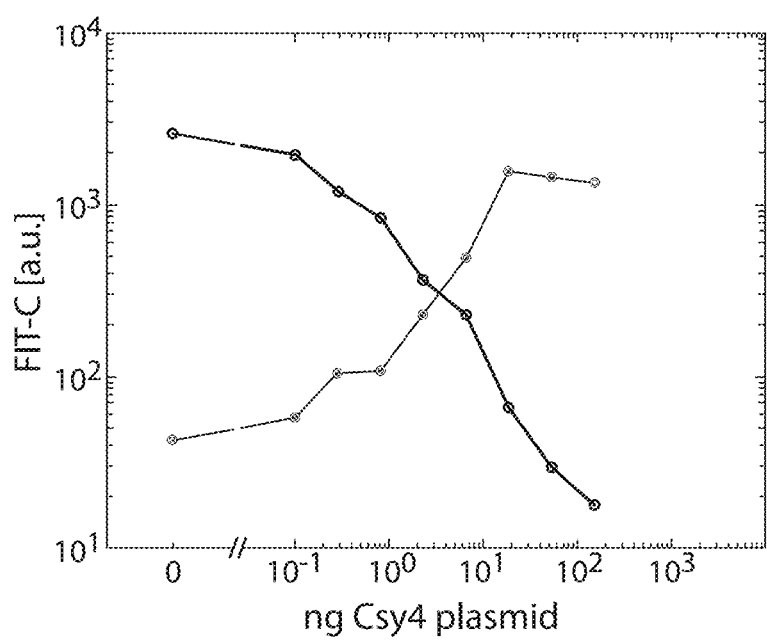
FIGS. 4A-4E: Csy4 signal inverter.
Figure 4B:
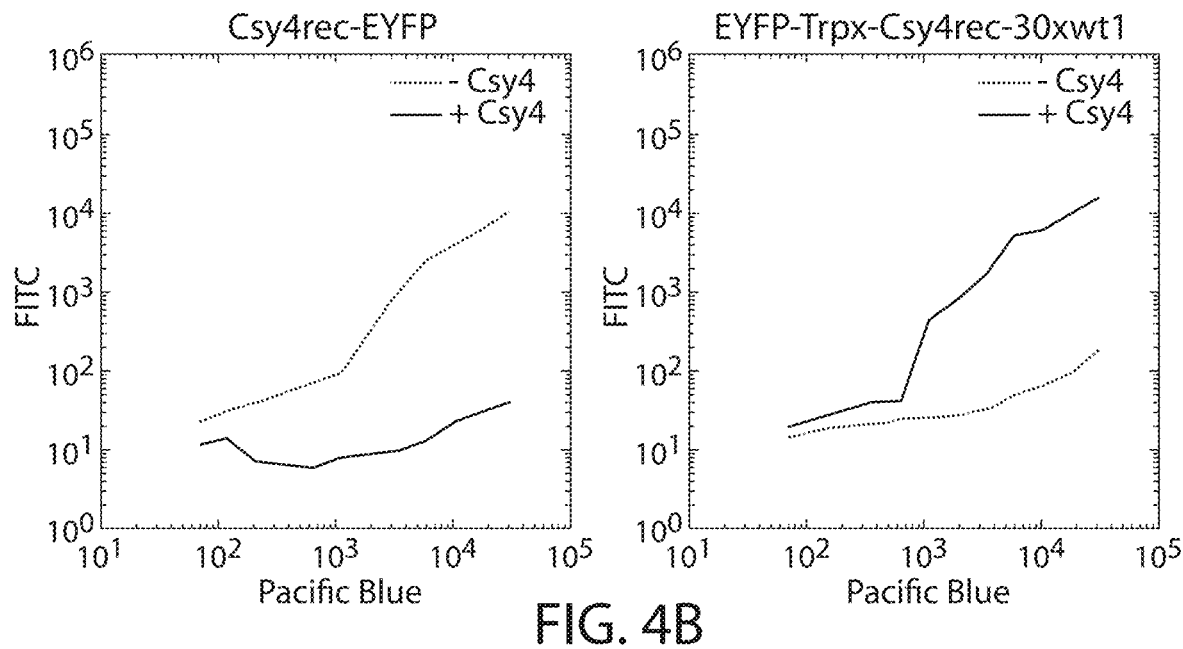
Figure 4C:
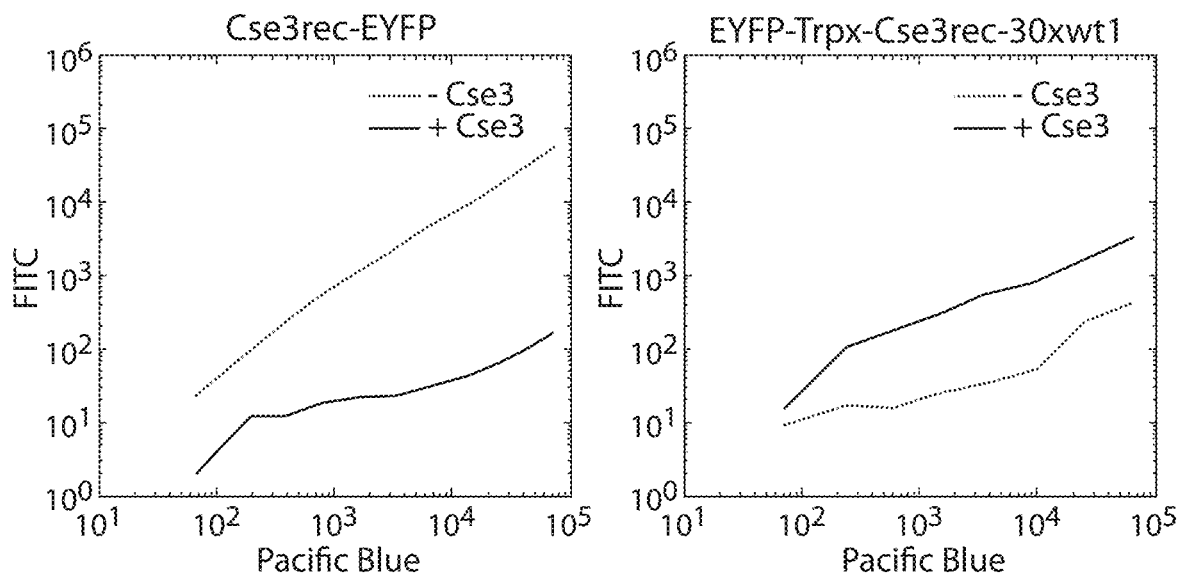
Figure 4D:
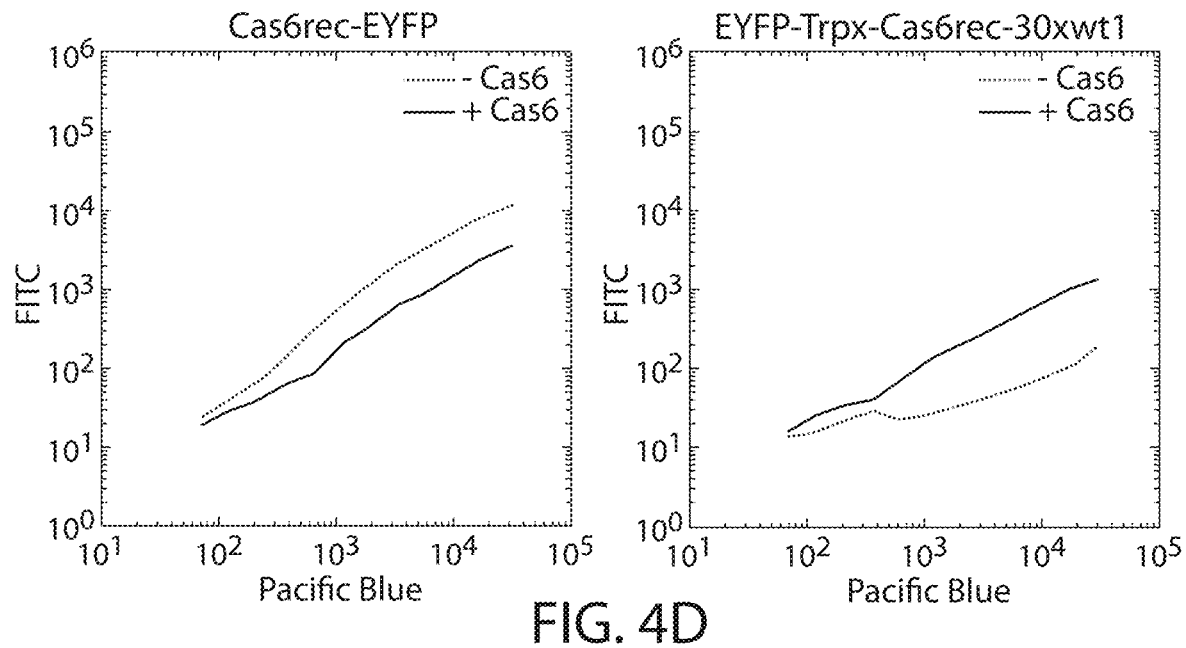
Figure 4E:
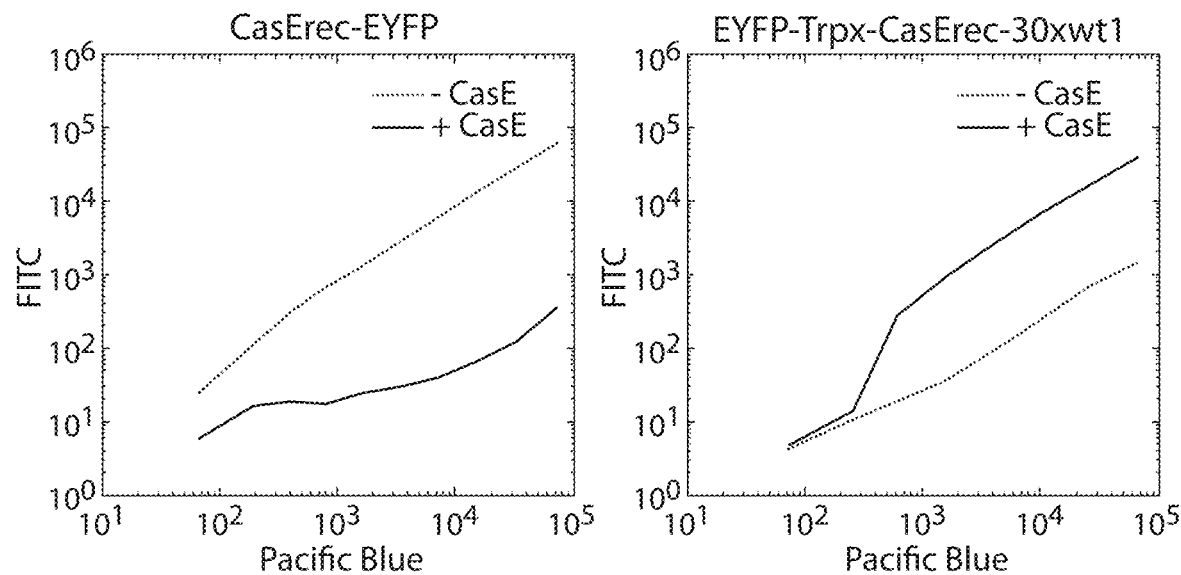

When a Csy4 recognition site (Csy4rec) was inserted into the 5' UTR of a gene constitutively expressing EYFP, the Csy4 inhibited EYFP expression leading to a signal that was inversely proportional to amount of Csy4 (FIG. 4A, blue curve).

Csy4rec was inserted into the cassette between the triplex and 30 repeats of the Geissler degradation signal. Adding the recognition site alone did not disrupt the degradation of the reporter, and when constitutive Csy4, Cse3, Cas6, or CasE plasmid was transfected into the same cells, expression was rescued (see FIGS. 4B to 4E). This therefore inverts the signal of the ribonuclease so that output expression is proportional to Csy4 amount (FIG. 4A, magenta curve).

miRNA Inverter

Figure 5A:
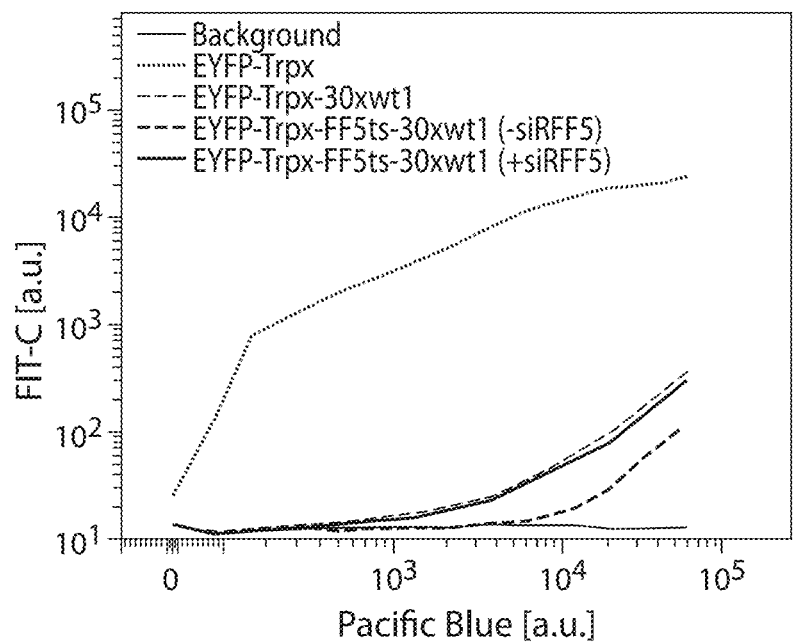
FIGS. 5A-5D: miRNA signal inverter.
Figure 5B:
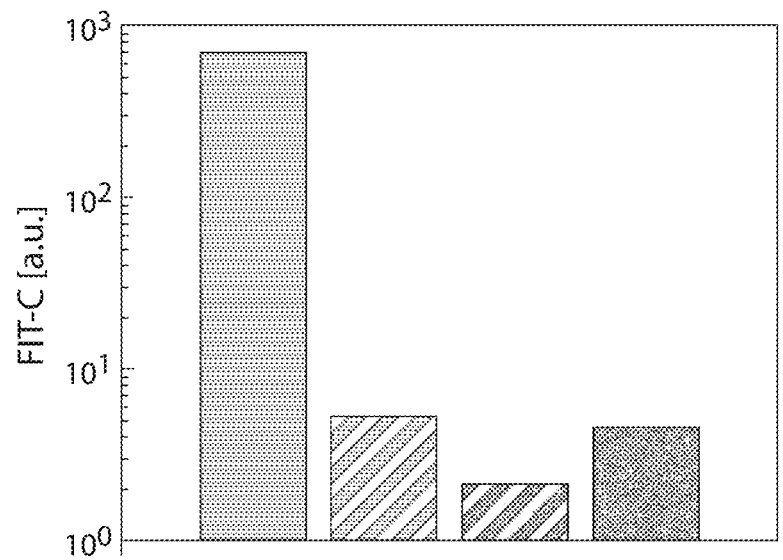
Figure 5C:
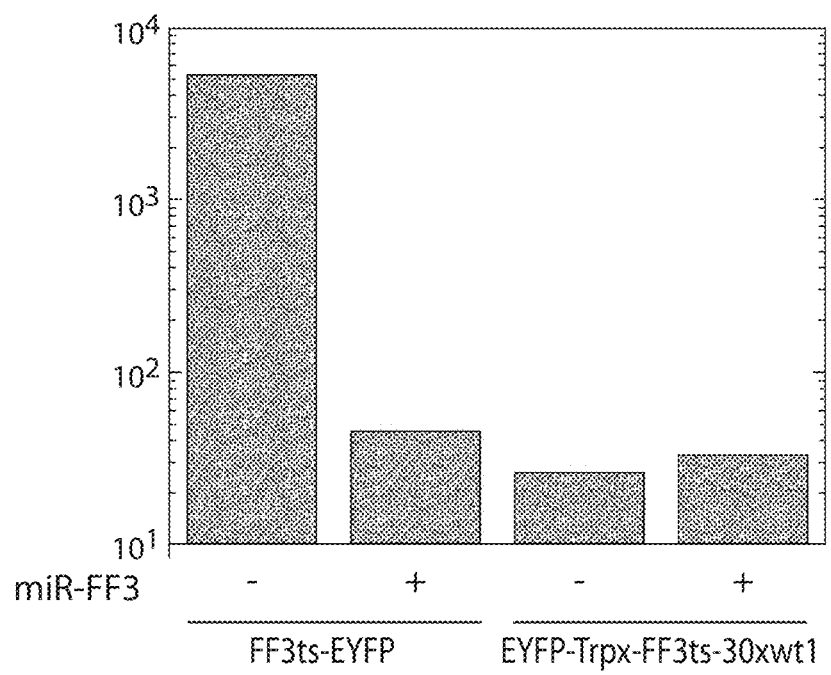
Figure 5D:
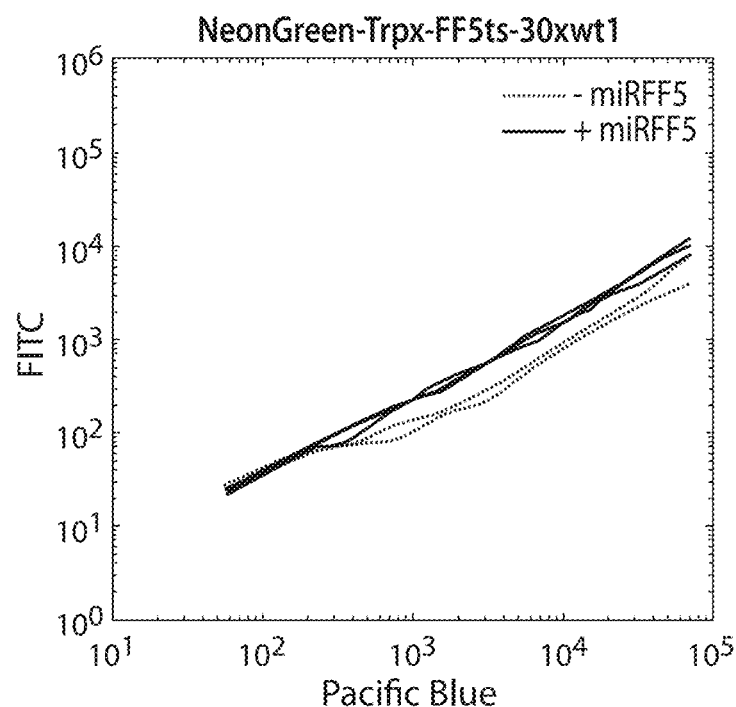

It may also be possible to invert the signal due to miRNA cleavage. FF5 target sites were inserted into the cassette between the triplex and 30 repeats of the Geissler degradation signal. Adding the target site alone did not disrupt the degradation of the reporter, and when siRNA FF5 was transfected into the same cells, expression was rescued 2 fold (see FIGS. 5A-5B). An increase in the output signal in response to siRNA FF3 was also observed (FIG. 5C). An increase in the output signal in response to microRNA FF5 was also observed (FIG. 5D).

Ribozyme Inverter

Figure 6A:
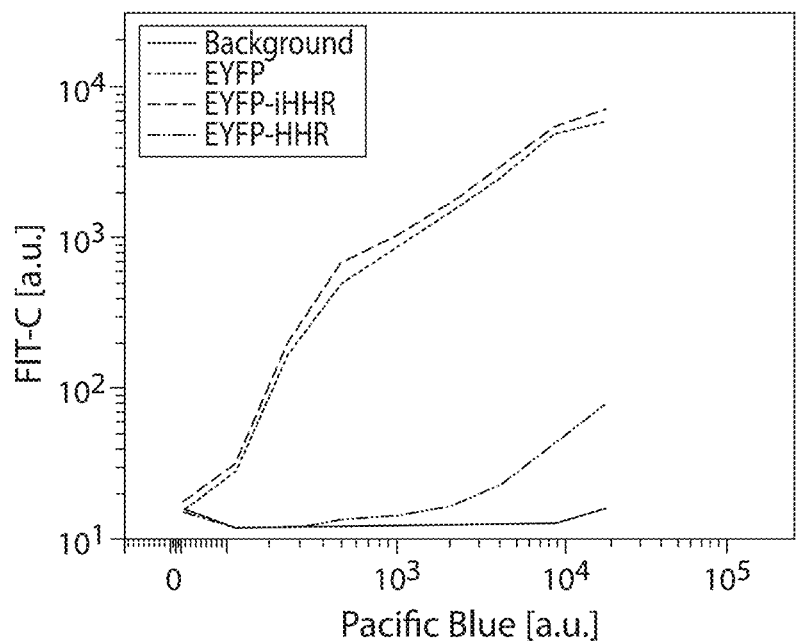
FIGS. 6A-6C: Ribozyme effects.
Figure 6B:
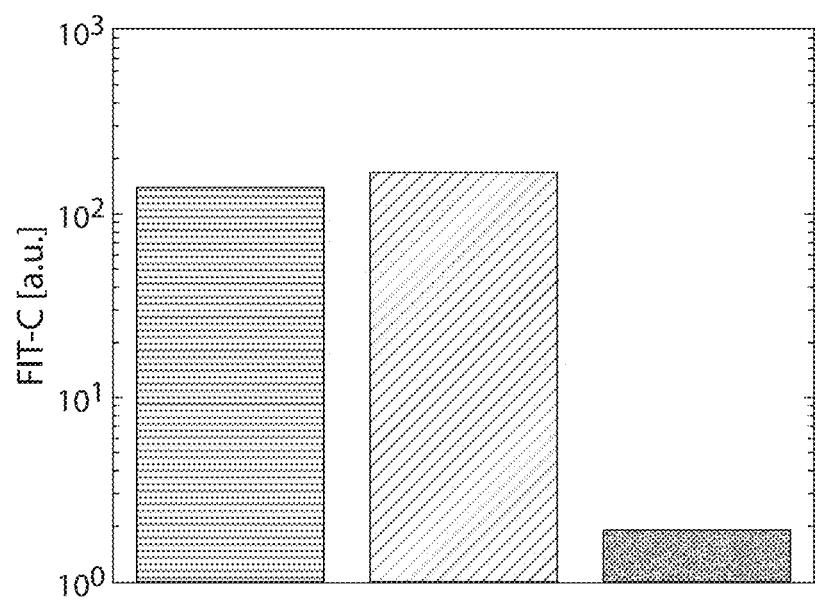
Figure 6C:
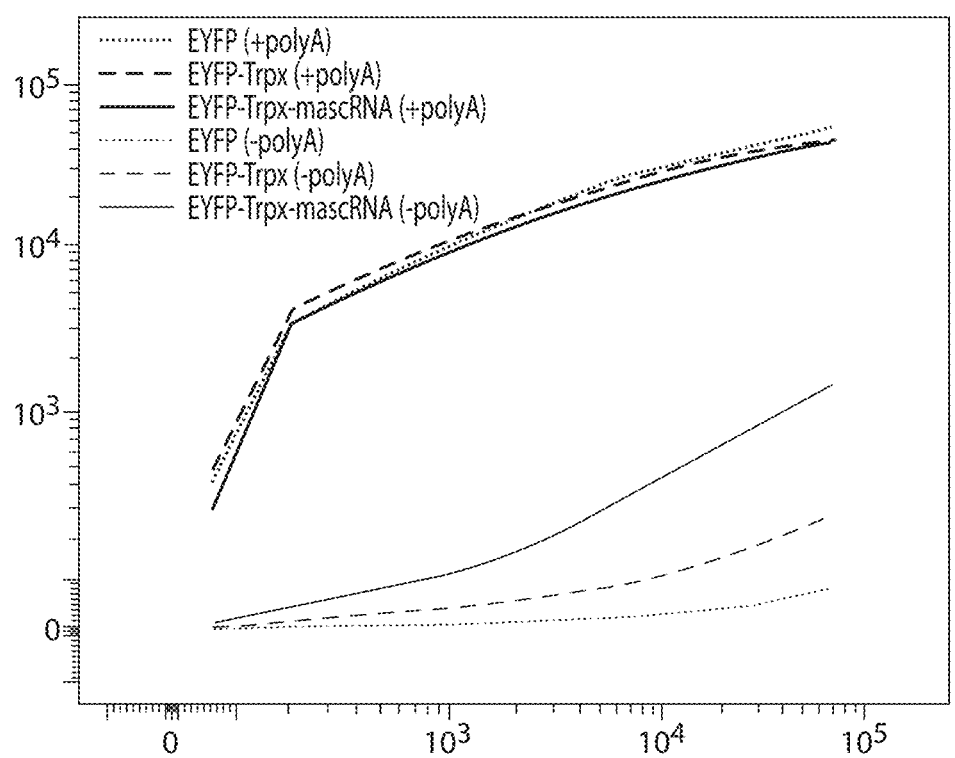

It may also be possible to invert the signal resulting from ribozyme cleavage. An inactive hammerhead ribozyme (iHHR) placed in the 3' UTR of a transgene constitutively expressing EYFP has little effect on its expression, however when the ribozyme is active, the transcript is cleaved resulting in degradation and 89 fold decreased expression (see FIGS. 6A-6B). When the same inactive and active ribozymes are placed in this signal inverter (between the triplex and degradation sequences) the effect should be reversed: when the ribozyme is inactive, the degradation sequences remain intact and the transcript expressing EYFP is quickly degraded resulting in low fluorescence, while when the ribozyme is active, the degradation signals are cleaved off resulting in a stable transcript and high expression. Further, in the absence of a polyA tail (the transcript should get degraded) fluorescence is rescued when the mascRNA sequence (which is targeted by RNase P) is added after the triplex (FIG. 6C).

Enabling an Ultrasensitive Switch

Figure 7A:
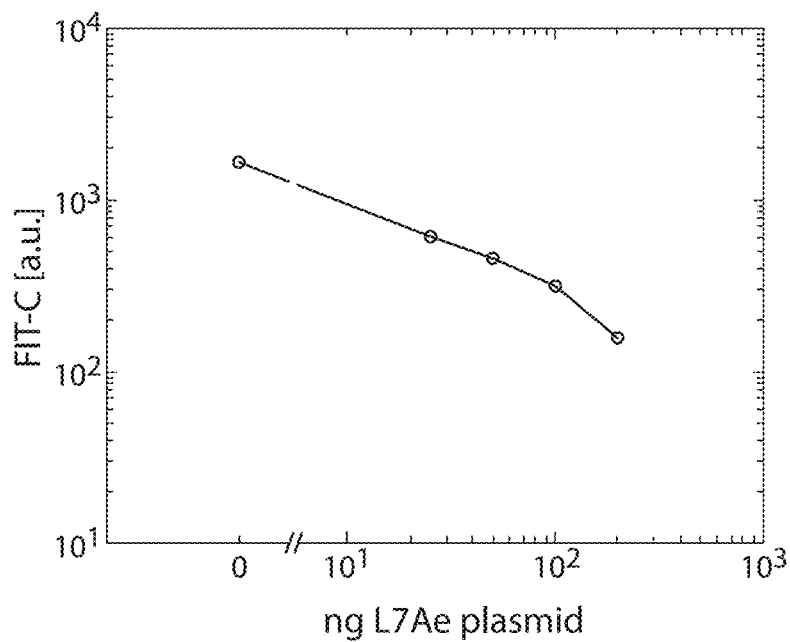
FIGS. 7A-7B: L7Ae effects.

It may be possible to achieve an ultrasensitive switch by interacting at two levels of a cascade. One manifestation of this mechanism might be through the use of L7Ae, which has been shown to inhibit translation by binding a k-turn RNA motif in a transcript[6]. Two repeats of the k-turn motif were inserted in the 5'UTR of EYFP and expression was controlled by the level of plasmid expressing L7Ae (see FIG. 7A).

Figure 7B:
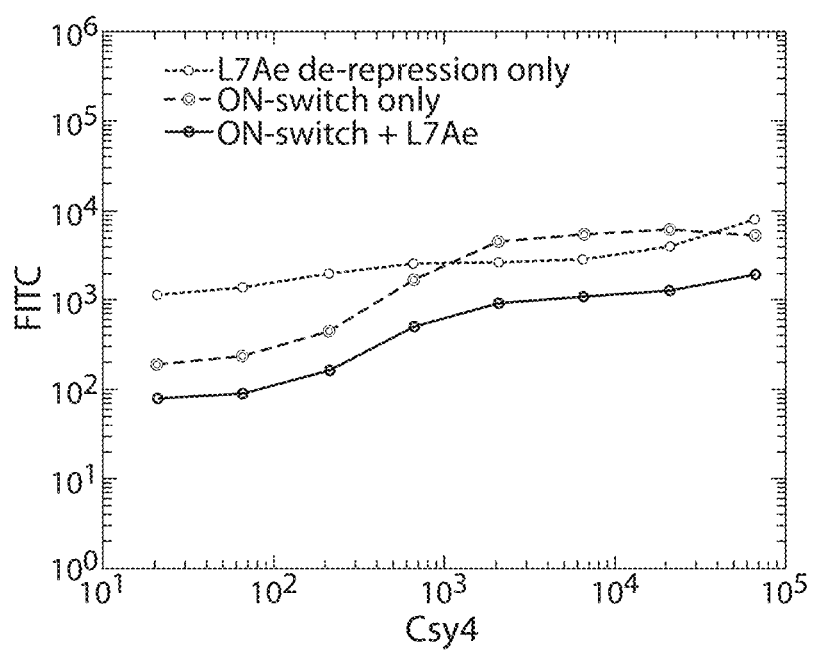

By inserting a cleaving target site in the transcript encoding L7Ae and also between a signal inverter module downstream of EYFP (containing 2 k-turn motifs upstream) as described, it may be possible to control the fluorescence response to the cleaver by varying the level of L7Ae. The background of the "ON"-switch is decreased (as indicated by a shift of the curve to the right) by incorporating the L7Ae construct for an ultrasensitive response (FIG. 7B).

Methods:

Cell Culture and Transfection

HEK293FT cells used in this study were maintained in Dulbecco's modified Eagle medium (DMEM, Corning) supplemented with 10% FBS (VWR), 1% penicillin/streptomycin/L-Glutamine (Corning) and 1% non-essential amino acids (Corning) at 37° C. and 5% $CO_2$.

Transfections were carried out in 24-well plate format with Lipofectamine 3000 transfection reagent (Invitrogen). Cells were harvested by trypsinization and $1.5 \times 10^6$ cells were seeded in 500 uL culture medium in each well. Immediately following, 600 ng total DNA was diluted in 25 uL Opti-MEM (Thermo Fisher) and 1.2 uL of P300 was added to the dilution. 1.2 uL of Lipoectamine 3000 was diluted in 25 uL Opti-MEM and this dilution was added to the DNA dilution and mixed well. The complexes were incubated for 5-10 minutes before being added dropwise to the freshly seeded cells, followed by gentle rocking.

Flow Cytometry & Data Analysis

Cells were analyzed by flow cytometry 48 hours after transfection using the LSR-II Fortessa Flow Cytometer. 20,000 events were collected per sample.

For each sample, data were segmented by constitutive transfection marker fluorescence in the Pacific Blue channel into bins and geometric mean and variance computed for the data points in each bin. For bar plots the geometric mean of these bin values was calculated for bins greater than the autoflourescence cutoff which was calculated from the 99$^{th}$ percentile Pacific Blue value of non-transfected cells.

DNA Cloning and Plasmid Construction

Plasmid vectors were created using the Golden Gate cloning system. DNA oligos were ordered as necessary from IDT.

CONCLUSIONS

Herein the Geissler domain is shown to be a potent "degradation domain" for transcripts which alone may be a mechanism for designing mRNA stability. The triplex sequence can stabilize the 3' end of transcripts that do not contain a polyA tail, but does not block the degradation mechanism utilized by the Geissler sequences. When used in combination within a transcript, these sequences represent an "inverter module": cleaving target sites such as ribonuclease recognition sites, miRNA target sites, or ribozymes can be inserted between the triplex and degradation signals to induce expression only in a cleavage event. This mechanism can be useful in the detection of disease-specific miRNAs or for the activity monitoring of ribonucleases and ribozymes. When combined with the traditional "OFF" switch of RNA cleavers, it is shown that it may also be possible to create an RNA-level ultrasensitive switch.

REFERENCES

1. Lu, J. et al. MicroRNA expression profiles classify human cancers. Nature 435, 834-838 (2005).
2. Xie, Z., Wroblewska, L., Prochazka, L., Weiss, R. & Benenson, Y. Multi-Input RNAi-Based Logic Circuit for Identification of Specific Cancer Cells. Science (80). 333, 1307-1311 (2011).
3. Geissler, R. et al. A widespread sequence-specific mRNA decay pathway mediated by hnRNP A1 and A2/B1. 1-23 (2016). doi:10.1101/gad.277392.116
4. Wilusz, J. E. et al. A triple helix stabilizes the 3 9 ends of long noncoding RNAs that lack poly (A) tails. Genes & Dev. 26, 2392-2407 (2012).
5. Zhang, Q., Bhattacharya, S. & Andersen, M. E. Ultrasensitive response motifs: basic amplifiers in molecular signalling networks. Open Biol. 3, 130031 (2013).
6. Saito, H. et al. Synthetic translational regulation by an L7Ae-kink-turn RNP switch. Nat. Chem. Biol. 6, 71-78 (2010).

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A composition comprising:
   (i) a first genetic circuit encoding an RNA transcript, the genetic circuit comprising
   a first promoter operably linked to a nucleotide sequence encoding an output molecule followed, from 5' to 3', by an RNA stabilizer, a cleavage site for an RNA cleaver, and a degradation signal, wherein the RNA transcript comprises one or more recognition sites for an RNA repressor operably linked to the nucleotide sequence encoding the output molecule; and
   (ii) a second genetic circuit comprising a second promoter operably linked to a nucleotide sequence encoding the RNA repressor, and one or more cleavage sites for the RNA cleaver.

2. The composition of claim 1, further comprising:
   (iii) a third genetic circuit comprising a third promoter operably linked to a nucleotide sequence encoding the RNA cleaver.

3. The composition of claim 1, wherein the RNA cleaver is selected from the group consisting of: endoribonucleases, RNAi molecules, and ribozymes.

4. The composition of claim 1, wherein the RNA repressor is an RNA binding protein.

5. The composition of claim 4, wherein the RNA binding protein is fused to a modifying domain.

6. The composition of claim 1, wherein the RNA stabilizer is selected from the group consisting of: MALAT1 triplex, MENβ triplex, KSHV PAN triplex, histone stem loop, and a polyA signal.

7. A cell comprising the first and second genetic circuits of claim 1.

8. The cell of claim 7, wherein the first and second genetic circuits are inserted into the genome of the cell.

9. A method comprising maintaining the cell of claim 7.

10. The method of claim 2, further comprising detecting the output molecule.

11. The method of claim 10, further comprising classifying the cell.

12. A method comprising delivering the RNA transcript encoded by the first genetic circuit of claim 1 to a cell and detecting the output molecule.

13. A method of treating a disease or disorder comprising administering an effective amount of a composition comprising the composition of claim 2 to a subject in need thereof, wherein the output molecule is a therapeutic molecule that is effective for treating the disease or disorder.

14. An RNA transcript encoded by the first genetic circuit of claim 1.

* * * * *

UNITED STATES PATENT AND TRADEMARK OFFICE
CERTIFICATE OF CORRECTION

| | | |
|---|---|---|
| PATENT NO. | : 11,795,455 B2 | Page 1 of 1 |
| APPLICATION NO. | : 16/049042 | |
| DATED | : October 24, 2023 | |
| INVENTOR(S) | : Ron Weiss et al. | |

It is certified that error appears in the above-identified patent and that said Letters Patent is hereby corrected as shown below:

In the Claims

Claim 10, at Column 80, Line 28: "The method of claim 2…" should read --The method of claim 9…--

Signed and Sealed this
Twenty-sixth Day of December, 2023

Katherine Kelly Vidal
*Director of the United States Patent and Trademark Office*

SEQUENCE LISTING

```
<160> NUMBER OF SEQ ID NOS: 56

<210> SEQ ID NO 1
<211> LENGTH: 8
<212> TYPE: DNA
<213> ORGANISM: Artificial Sequence
<220> FEATURE:
<223> OTHER INFORMATION: Synthetic Polynucleotide

<400> SEQUENCE: 1 taasttat                                                                 8

<210> SEQ ID NO 2
<211> LENGTH: 8
<212> TYPE: DNA
<213> ORGANISM: Artificial Sequence
<220> FEATURE:
<223> OTHER INFORMATION: Synthetic Polynucleotide

<400> SEQUENCE: 2 taagttat                                                                 8

<210> SEQ ID NO 3
<211> LENGTH: 8
<212> TYPE: DNA
<213> ORGANISM: Artificial Sequence
<220> FEATURE:
<223> OTHER INFORMATION: Synthetic Polynucleotide
```

```
<400> SEQUENCE: 3 taagacat                                                                        8

<210> SEQ ID NO 4
<211> LENGTH: 8
<212> TYPE: DNA
<213> ORGANISM: Artificial Sequence
<220> FEATURE:
<223> OTHER INFORMATION: Synthetic Polynucleotide

<400> SEQUENCE: 4 taacttat                                                                        8

<210> SEQ ID NO 5
<211> LENGTH: 8
<212> TYPE: RNA
<213> ORGANISM: Artificial Sequence
<220> FEATURE:
<223> OTHER INFORMATION: Synthetic Polynucleotide

<400> SEQUENCE: 5 uaasuuau                                                                        8

<210> SEQ ID NO 6
<211> LENGTH: 8
<212> TYPE: RNA
<213> ORGANISM: Artificial Sequence
<220> FEATURE:
<223> OTHER INFORMATION: Synthetic Polynucleotide

<400> SEQUENCE: 6 uaaguuau                                                                        8

<210> SEQ ID NO 7
<211> LENGTH: 8
<212> TYPE: RNA
<213> ORGANISM: Artificial Sequence
<220> FEATURE:
<223> OTHER INFORMATION: Synthetic Polynucleotide

<400> SEQUENCE: 7 uaacuuau                                                                        8

<210> SEQ ID NO 8
<211> LENGTH: 8
<212> TYPE: RNA
<213> ORGANISM: Artificial Sequence
<220> FEATURE:
<223> OTHER INFORMATION: Synthetic Polynucleotide

<400> SEQUENCE: 8 uaagacau                                                                        8

<210> SEQ ID NO 9
<211> LENGTH: 264
<212> TYPE: PRT
<213> ORGANISM: Pyrococcus furiosus

<400> SEQUENCE: 9

Met Arg Phe Leu Ile Arg Leu Val Pro Glu Asp Lys Asp Arg Ala Phe
1               5                   10                  15

Lys Val Pro Tyr Asn His Gln Tyr Tyr Leu Gln Gly Leu Ile Tyr Asn
            20                  25                  30
```

```
Ala Ile Lys Ser Ser Asn Pro Lys Leu Ala Thr Tyr Leu His Glu Val
            35                  40                  45
Lys Gly Pro Lys Leu Phe Thr Tyr Ser Leu Phe Met Ala Glu Lys Arg
 50                  55                  60
Glu His Pro Lys Gly Leu Pro Tyr Phe Leu Gly Tyr Lys Lys Gly Phe
 65                  70                  75                  80
Phe Tyr Phe Ser Thr Cys Val Pro Glu Ile Ala Glu Ala Leu Val Asn
                 85                  90                  95
Gly Leu Leu Met Asn Pro Glu Val Arg Leu Trp Asp Glu Arg Phe Tyr
            100                 105                 110
Leu His Glu Ile Lys Val Leu Arg Glu Pro Lys Lys Phe Asn Gly Ser
        115                 120                 125
Thr Phe Val Thr Leu Ser Pro Ile Ala Val Thr Val Arg Lys Gly
130                 135                 140
Lys Ser Tyr Asp Val Pro Pro Met Glu Lys Glu Phe Tyr Ser Ile Ile
145                 150                 155                 160
Lys Asp Asp Leu Gln Asp Lys Tyr Val Met Ala Tyr Gly Asp Lys Pro
                165                 170                 175
Pro Ser Glu Phe Glu Met Glu Val Leu Ile Ala Lys Pro Lys Arg Phe
            180                 185                 190
Arg Ile Lys Pro Gly Ile Tyr Gln Thr Ala Trp His Leu Val Phe Arg
        195                 200                 205
Ala Tyr Gly Asn Asp Asp Leu Leu Lys Val Gly Tyr Glu Val Gly Phe
    210                 215                 220
Gly Glu Lys Asn Ser Leu Gly Phe Gly Met Val Lys Val Glu Gly Asn
225                 230                 235                 240
Lys Thr Thr Lys Glu Ala Glu Glu Gln Glu Lys Ile Thr Phe Asn Ser
                245                 250                 255
Arg Glu Glu Leu Lys Thr Gly Val
            260

<210> SEQ ID NO 10
<211> LENGTH: 795
<212> TYPE: DNA
<213> ORGANISM: Pyrococcus furiosus

<400> SEQUENCE: 10
atgcgcttcc tcattcgtct cgtgcctgag gataaggatc gggccttaa agtgccatat      60 aaccatcagt attacctgca gggcctcatc tataatgcca tcaaatcctc caatccgaag    120
ctggccacct acctgcatga ggtgaagggt cccaaactgt tcacctacag cctgtttatg    180
gccgaaaaac gcgaacaccc taaggggctg ccttactttt ggggtacaa gaagggcttc    240 ttctactttt ctacctgcgt gccggagatc gctgaagcac tggtcaacgg actcctgatg    300
aatccagagg tgcgcctgtg gacgaacgc ttctacctgc acgaaattaa ggttttgaga    360
gagcctaaga agttcaacgg ctctaccttc gtcacctgt ctccgattgc tgtgactgtc    420
gtgaggaagg gtaagagtta tgatgtcccc cctatggaga aggagttta cagtatcatc    480 aaagacgacc tgcaagataa ggatgtgatg gcctacggcg acaagcccc atccgaattc    540 gagatggagg tgctgattgc taagccgaaa cggtttcgta ttaagcctgg catctatcag    600
acagcctggc acctggtttt tagggcctac ggaaacgacg acctgctgaa ggttggttac    660
gaggttgggt tcggagaaaa gaactccctg ggattcggca tggtgaaggt ggaggggaac    720
```

```
aagaccacaa aagaagctga agagcaggaa aagatcacct tcaactctcg cgaggagctg    780
aagaccggcg tgtga                                                     795
```

<210> SEQ ID NO 11
<211> LENGTH: 29
<212> TYPE: DNA
<213> ORGANISM: Pyrococcus furiosus

<400> SEQUENCE: 11

```
gttacaataa gactaaatag aattgaaag                                       29
```

<210> SEQ ID NO 12
<211> LENGTH: 187
<212> TYPE: PRT
<213> ORGANISM: Pseudomonas aeruginosa

<400> SEQUENCE: 12

```
Met Asp His Tyr Leu Asp Ile Arg Leu Arg Pro Asp Pro Glu Phe Pro
 1               5                  10                  15

Pro Ala Gln Leu Met Ser Val Leu Phe Gly Lys Leu His Gln Ala Leu
            20                  25                  30

Val Ala Gln Gly Gly Asp Arg Ile Gly Val Ser Phe Pro Asp Leu Asp
        35                  40                  45

Glu Ser Arg Ser Arg Leu Gly Glu Arg Leu Arg Ile His Ala Ser Ala
    50                  55                  60

Asp Asp Leu Arg Ala Leu Leu Ala Arg Pro Trp Leu Glu Gly Leu Arg
65                  70                  75                  80

Asp His Leu Gln Phe Gly Glu Pro Ala Val Val Pro His Pro Thr Pro
                85                  90                  95

Tyr Arg Gln Val Ser Arg Val Gln Ala Lys Ser Asn Pro Glu Arg Leu
            100                 105                 110

Arg Arg Arg Leu Met Arg Arg His Asp Leu Ser Glu Glu Ala Arg
        115                 120                 125

Lys Arg Ile Pro Asp Thr Val Ala Arg Ala Leu Asp Leu Pro Phe Val
    130                 135                 140

Thr Leu Arg Ser Gln Ser Thr Gly Gln His Phe Arg Leu Phe Ile Arg
145                 150                 155                 160

His Gly Pro Leu Gln Val Thr Ala Glu Glu Gly Gly Phe Thr Cys Tyr
                165                 170                 175

Gly Leu Ser Lys Gly Gly Phe Val Pro Trp Phe
            180                 185
```

<210> SEQ ID NO 13
<211> LENGTH: 564
<212> TYPE: DNA
<213> ORGANISM: Pseudomonas aeruginosa

<400> SEQUENCE: 13

```
atggaccact atctggacat cagactgagg cccgatcctg agttccctcc cgcccagctg    60
atgagcgtgc tgtttggcaa gctgcatcag gctctggtcg cccaaggcgg agacagaatc   120
ggcgtgtcct tccccgacct ggacgagtcc cggagtcgcc tgggcgagcg gctgagaatc   180
cacgccagcg cagacgatct gcgcgccctg ctggcccggc cttggctgga gggcctgcgg   240
gatcatctgc agtttggcga gcccgccgtg gtgccacacc caaccccta ccgccaggtg   300 agccgcgtga aggccaagtc aaatcccgag agactgcggc ggaggctgat gaggcgacat   360
gatctgagcg aggaggaggc cagaaagaga atccccgaca cagtggccag agccctggat   420
```

```
ctgccatttg tgaccctgcg agccagagc actggccagc atttcagact gttcatcaga      480
cacgggcccc tgcaggtgac agccgaggag ggcggattta catgctatgg cctgtctaaa      540
ggcggcttcg tgccctggtt ctga                                             564
```

<210> SEQ ID NO 14
<211> LENGTH: 28
<212> TYPE: DNA
<213> ORGANISM: Pseudomonas aeruginosa

<400> SEQUENCE: 14

```
gttcactgcc gtataggcag ctaagaaa                                          28
```

<210> SEQ ID NO 15
<211> LENGTH: 199
<212> TYPE: PRT
<213> ORGANISM: Escherichia coli

<400> SEQUENCE: 15

```
Met Tyr Leu Ser Lys Ile Ile Ile Ala Arg Ala Trp Ser Arg Asp Leu
1               5                   10                  15

Tyr Gln Leu His Gln Glu Leu Trp His Leu Phe Pro Asn Arg Pro Asp
            20                  25                  30

Ala Ala Arg Asp Phe Leu Phe His Val Glu Lys Arg Asn Thr Pro Glu
        35                  40                  45

Gly Cys His Val Leu Leu Gln Ser Ala Gln Met Pro Val Ser Thr Ala
    50                  55                  60

Val Ala Thr Val Ile Lys Thr Lys Gln Val Glu Phe Gln Leu Gln Val
65                  70                  75                  80

Gly Val Pro Leu Tyr Phe Arg Leu Arg Ala Asn Pro Ile Lys Thr Ile
                85                  90                  95

Leu Asp Asn Gln Lys Arg Leu Asp Ser Lys Gly Asn Ile Lys Arg Cys
            100                 105                 110

Arg Val Pro Leu Ile Lys Glu Ala Glu Gln Ile Ala Trp Leu Gln Arg
        115                 120                 125

Lys Leu Gly Asn Ala Ala Arg Val Glu Asp Val His Pro Ile Ser Glu
130                 135                 140

Arg Pro Gln Tyr Phe Ser Gly Glu Gly Lys Asn Gly Lys Ile Gln Thr
145                 150                 155                 160

Val Cys Phe Glu Gly Val Leu Thr Ile Asn Asp Ala Pro Ala Leu Ile
                165                 170                 175

Asp Leu Leu Gln Gln Gly Ile Gly Pro Ala Lys Ser Met Gly Cys Gly
            180                 185                 190

Leu Leu Ser Leu Ala Pro Leu
        195
```

<210> SEQ ID NO 16
<211> LENGTH: 597
<212> TYPE: DNA
<213> ORGANISM: Escherichia coli

<400> SEQUENCE: 16

```
atgtacctca gtaagatcat catcgcccgc gcttggtccc gtgacctgta ccaactgcac      60
caagagctct ggcacctctt ccccaacagg ccagatgccg ctagagactt cctgttccac     120
gtggagaagc gtaacacccc cgaagggtgc cacgtgctgt tgcagagtgc ccagatgcca     180
gtgagtaccg ctgttgccac tgtcatcaag actaaacaag ttgaattcca actgcaagtg     240
```

| | | |
|---|---|---|
| ggcgtccctc tgtatttccg cctcagggcc aaccccatca aaaccatcct ggacaaccag | 300 | |
| aagcggctgg atagcaaagg taatatcaag agatgccgcg tgcctctgat caaggaggcc | 360 | |
| gagcagatcg cttggctgca acgcaagctg ggtaacgccg cgagagtgga agatgtgcac | 420 | |
| ccaatctccg agcgcccgca gtatttctcc ggggagggga agaacggcaa aattcagact | 480 | |
| gtctgcttcg aggggtgct cactattaac gacgcccctg ctctgatcga cctcctgcag | 540 | |
| cagggcattg ggcccgcgaa gagcatggga tgcggattgt tgagcctggc accctg | 597 | |

<210> SEQ ID NO 17
<211> LENGTH: 29
<212> TYPE: DNA
<213> ORGANISM: Escherichia coli

<400> SEQUENCE: 17
gagttccccg cgccagcggg gataaaccg    29

<210> SEQ ID NO 18
<211> LENGTH: 211
<212> TYPE: PRT
<213> ORGANISM: Thermus thermophilus

<400> SEQUENCE: 18

Met Trp Leu Thr Lys Leu Val Leu Asn Pro Ala Ser Arg Ala Ala Arg
1               5                   10                  15

Arg Asp Leu Ala Asn Pro Tyr Glu Met His Arg Thr Leu Ser Lys Ala
            20                  25                  30

Val Ser Arg Ala Leu Glu Glu Gly Arg Glu Arg Leu Leu Trp Arg Leu
        35                  40                  45

Glu Pro Ala Arg Gly Leu Glu Pro Val Val Leu Val Gln Thr Leu
    50                  55                  60

Thr Glu Pro Asp Trp Ser Val Leu Asp Glu Gly Tyr Ala Gln Val Phe
65                  70                  75                  80

Pro Pro Lys Pro Phe His Pro Ala Leu Lys Pro Gly Gln Arg Leu Arg
                85                  90                  95

Phe Arg Leu Arg Ala Asn Pro Ala Lys Arg Leu Ala Ala Thr Gly Lys
            100                 105                 110

Arg Val Ala Leu Lys Thr Pro Ala Glu Lys Val Ala Trp Leu Glu Arg
        115                 120                 125

Arg Leu Glu Glu Gly Gly Phe Arg Leu Leu Glu Gly Glu Arg Gly Pro
    130                 135                 140

Trp Val Gln Ile Leu Gln Asp Thr Phe Leu Glu Val Arg Arg Lys Lys
145                 150                 155                 160

Asp Gly Glu Glu Ala Gly Lys Leu Leu Gln Val Gln Ala Val Leu Phe
                165                 170                 175

Glu Gly Arg Leu Glu Val Val Asp Pro Glu Arg Ala Leu Ala Thr Leu
            180                 185                 190

Arg Arg Gly Val Gly Pro Gly Lys Ala Leu Gly Leu Gly Leu Leu Ser
        195                 200                 205

Val Ala Pro
    210

<210> SEQ ID NO 19
<211> LENGTH: 636
<212> TYPE: DNA
<213> ORGANISM: Thermus thermophilus

<400> SEQUENCE: 19

```
atgtggttga ccaaattggt tctgaatcct gcgagccgcg cagcacggcg cgatttggct      60
aacccttacg agatgcatcg gactctttca aaagcggtta gcagggcttt ggaagaaggg     120
cgcgagcgcc ttttgtggag gctggagcca gctcggggac tggagccccc tgtcgtcctg     180
gtgcagaccc tcactgagcc tgattggtcc gtacttgatg aaggttacgc acaggtcttt     240
cctcctaagc ctttccaccc agcattgaag ccgggccagc ggctccgctt taggctccgg     300
gcgaatcccg ccaaacggtt ggctgccacc ggaaagcgag ttgcgttgaa aacgcccgcc     360
gaaaaagtgg cgtggcttga gaggcggctg gaggagggtg gttttcgact ccttgaaggg     420
gaaaggggac catgggtaca gatacttcaa gatacgttcc tggaggtgcg agaaaaaaa     480
gacggagaag aggcaggcaa gctgcttcaa gtccaagccg tcttgttcga ggggagactc     540
gaagttgttg atcctgagag agcacttgcg acactgagac gaggggtggg acctggtaaa     600
gcgctgggtc ttggacttct tagtgttgca ccatga                              636
```

<210> SEQ ID NO 20
<211> LENGTH: 29
<212> TYPE: DNA
<213> ORGANISM: Thermus thermophilus

<400> SEQUENCE: 20

```
gtagtcccca cgcgtgtggg gatggaccg                                       29
```

<210> SEQ ID NO 21
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 21

```
caccacgaac ctgatgagtc cgtgaggacg aaacgagcta gctcgtcgtt cgtgctg        57
```

<210> SEQ ID NO 22
<211> LENGTH: 65
<212> TYPE: DNA
<213> ORGANISM: Artificial Sequence
<220> FEATURE:
<223> OTHER INFORMATION: Synthetic Polynucleotide

<400> SEQUENCE: 22

```
ggcgtcggag tatccaatca gtggatgtac tactccctga tgagtcccaa ataggacgaa     60
acgcc                                                                 65
```

<210> SEQ ID NO 23
<211> LENGTH: 64
<212> TYPE: DNA
<213> ORGANISM: Artificial Sequence
<220> FEATURE:
<223> OTHER INFORMATION: Synthetic Polynucleotide

<400> SEQUENCE: 23

```
gggtgccctg tcggaggatg tgctttcctc cctgatgagt ccgtgaggac gaaacagggc     60
accc                                                                  64
```

<210> SEQ ID NO 24
<211> LENGTH: 68
<212> TYPE: DNA
<213> ORGANISM: Artificial Sequence

```
<220> FEATURE:
<223> OTHER INFORMATION: Synthetic Polynucleotide

<400> SEQUENCE: 24
ggccggcatg gtcccagcct cctcgctggc gccggctggg caacatgctt cggcatggcg    60
aatgggac                                                             68

<210> SEQ ID NO 25
<211> LENGTH: 341
<212> TYPE: DNA
<213> ORGANISM: Artificial Sequence
<220> FEATURE:
<223> OTHER INFORMATION: Synthetic Polynucleotide

<400> SEQUENCE: 25
atagggcgga gggaagctca tcagtggggc cacgagctga gtgcgtcctg tcactccact    60
cccatgtccc ttgggaaggt ctgagactag gccagaggc ggccctaaca gggctctccc   120
tgagcttcgg ggaggtgagt tcccagagaa cggggctccg cgcgaggtca gactgggcag   180
gagatgccgt ggaccccgcc cttcggggag gggcccggcg gatgcctcct tgccggagc    240 ttggaacaga ctcacggcca gcgaagtgag ttcaatggct gaggtgaggt accccgcagg   300
ggacctcata acccaattca gactactctc ctccgcccat t                       341

<210> SEQ ID NO 26
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 26
gacgctggtg gctggcactc ctggtttcca ggacggggtt caagtccctg cggtgtct     58

<210> SEQ ID NO 27
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 27
tttgtattca gcccatatcg                                                20

<210> SEQ ID NO 28
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 28
tttaattaaa gacttcaagc g                                              21

<210> SEQ ID NO 29
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 29
taattgtcaa atcagagtgc                                                20
```

```
<210> SEQ ID NO 30
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 30
tttatgagga atctctttgg                                                   20

<210> SEQ ID NO 31
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 31
ttcgaagtat tccgcgtacg                                                   20

<210> SEQ ID NO 32
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 32
aacgatatgg gctgaataca aa                                                22

<210> SEQ ID NO 33
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 33
ccgcttgaag tctttaatta aa                                                22

<210> SEQ ID NO 34
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 34
aagcactctg atttgacaat ta                                                22

<210> SEQ ID NO 35
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 35
aaccaaagag attcctcata aa                                                22

<210> SEQ ID NO 36
<211> LENGTH: 22
<212> TYPE: DNA
<213> ORGANISM: Artificial Sequence
<220> FEATURE:
<223> OTHER INFORMATION: Synthetic Polynucleotide
```

```
<400> SEQUENCE: 36
cacgtacgcg gaatacttcg aa                                          22

<210> SEQ ID NO 37
<211> LENGTH: 110
<212> TYPE: RNA
<213> ORGANISM: Artificial Sequence
<220> FEATURE:
<223> OTHER INFORMATION: Synthetic Polynucleotide

<400> SEQUENCE: 37
gauucgucag uaggguugua aagguuuuuc uuuuccugag aaaacaaccu uuguuuucu   60 cagguuuugc uuuuuggccu ucccuagcu uuaaaaaaaa aaaagcaaaa            110

<210> SEQ ID NO 38
<211> LENGTH: 74
<212> TYPE: RNA
<213> ORGANISM: Artificial Sequence
<220> FEATURE:
<223> OTHER INFORMATION: Synthetic Polynucleotide

<400> SEQUENCE: 38
gccgccgcag guguuucuuu uacugagugc agcccauggc cgcacucagg uuuugcuuuu   60
caccuuccca ucug                                                   74

<210> SEQ ID NO 39
<211> LENGTH: 64
<212> TYPE: RNA
<213> ORGANISM: Artificial Sequence
<220> FEATURE:
<223> OTHER INFORMATION: Synthetic Polynucleotide

<400> SEQUENCE: 39
gcuggguuuu uccuuguucg caccggacac cuccagugac cagacggcaa gguuuuaucc   60
cagu                                                              64

<210> SEQ ID NO 40
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 40
aaaaaggcuc uuuucagagc accca                                       25

<210> SEQ ID NO 41
<211> LENGTH: 207
<212> TYPE: PRT
<213> ORGANISM: Artificial Sequence
<220> FEATURE:
<223> OTHER INFORMATION: Synthetic Polypeptide

<400> SEQUENCE: 41

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60
```

| | | | | | | | | | | | | | | | |
|---|---|---|---|---|---|---|---|---|---|---|---|---|---|---|---|
|Thr|His|Phe|Cys|Pro|Leu|Glu|Gly|Glu|Ser|Trp|Gln|Asp|Phe|Leu|Arg|
|65| | | |70| | | | |75| | | | |80| |

| | | | | | | | | | | | |
|---|---|---|---|---|---|---|---|---|---|---|---|
|Asn|Asn|Ala|Lys|Ser|Phe|Arg|Cys|Ala|Leu|Leu|Ser|His|Arg|Asp|Gly|
| | | | |85| | | | |90| | | | |95| |

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser
        195                 200                 205

<210> SEQ ID NO 42
<211> LENGTH: 621
<212> TYPE: DNA
<213> ORGANISM: Artificial Sequence
<220> FEATURE:
<223> OTHER INFORMATION: Synthetic Polynucleotide

<400> SEQUENCE: 42
atgtcaagac tcgacaagag caaggtgatt aacagtgcac tggaacttct caatgaagtt      60
gggatcgagg ggctgactac tagaaaactc gcacagaaac tgggggttga gcagcccacc     120
ttgtactggc acgttaaaaa caaaagggcc ctgctggatg ctctggccat cgagatgctg     180
gataggcatc ataccccactt ctgccctctg gaaggagaat cctggcagga tttccttaga     240
aacaacgcca agtcctttcg ctgtgctctt cttagccacc gggatggtgc taaagtccat     300
ctcggcacac gaccaactga aaagcagtac gaaactctcg agaaccagct ggcctttctc     360
tgtcaacagg gctttctctc tgaaaacgcc ctgtacgcac tgagtgcagt gggcactttt     420
acactcggat gtgttctgga ggaccaagaa catcaggtgg caaaggaaga gagggagacc     480
cctacgactg actccatgcc ccctctcttg aggcaggcaa tagaattgtt cgaccatcag     540
ggcgcagaac ccgcctttct gtttgggctg gaactgatta tctgcggtct tgagaaacag     600
ctgaagtgcg agtccgggag c                                              621

<210> SEQ ID NO 43
<211> LENGTH: 124
<212> TYPE: DNA
<213> ORGANISM: Artificial Sequence
<220> FEATURE:
<223> OTHER INFORMATION: Synthetic Polynucleotide

<400> SEQUENCE: 43
atccaggcag agaaaggtcg atacggacgg aatgtggtgg cctggatcaa caacaacaaa      60
atccaggcag agaaaggtcg atacggacgg aatgtggtgg cctggatcaa caacaacaac     120
actg                                                                 124

<210> SEQ ID NO 44
<211> LENGTH: 300
<212> TYPE: PRT
<213> ORGANISM: Artificial Sequence
<220> FEATURE:
<223> OTHER INFORMATION: Synthetic Polypeptide

<400> SEQUENCE: 44

Met Leu Pro Leu Asp Ser Leu Leu His Leu Thr Ala Pro Ala Pro
1               5                   10                  15

Ala Pro Ala Pro Ala Pro Arg Arg Ser His Gln Thr Pro Thr Pro Pro
            20                  25                  30

His Ser Phe Leu Ser Pro Asp Ala Gln Val Leu Val Leu Ala Ile Ser
        35                  40                  45

Ser His Pro Leu Pro Thr Leu Ala Ala Phe Leu Ala Ser Arg Arg Asp
    50                  55                  60

Glu Leu Leu Arg Ala Asp Ile Thr Ser Leu Leu Lys Ala Leu Glu Leu
65                  70                  75                  80

Ser Gly His Trp Glu Trp Ala Leu Ala Leu Leu Arg Trp Ala Gly Lys
                85                  90                  95

Glu Gly Ala Ala Asp Ala Ser Ala Leu Glu Met Val Val Arg Ala Leu
            100                 105                 110

Gly Arg Glu Gly Gln His Asp Ala Val Cys Ala Leu Leu Asp Glu Thr
        115                 120                 125

Pro Leu Pro Pro Gly Ser Arg Leu Asp Val Arg Ala Tyr Thr Thr Val
    130                 135                 140

Leu His Ala Leu Ser Arg Ala Gly Arg Tyr Glu Arg Ala Leu Glu Leu
145                 150                 155                 160

Phe Ala Glu Leu Arg Arg Gln Gly Val Ala Pro Thr Leu Val Thr Tyr
                165                 170                 175

Asn Val Val Leu Asp Val Tyr Gly Arg Met Gly Arg Ser Trp Pro Arg
            180                 185                 190

Ile Val Ala Leu Leu Asp Glu Met Arg Ala Ala Gly Val Glu Pro Asp
        195                 200                 205

Gly Phe Thr Ala Ser Thr Val Ile Ala Ala Cys Cys Arg Asp Gly Leu
    210                 215                 220

Val Asp Glu Ala Val Ala Phe Phe Glu Asp Leu Lys Ala Arg Gly His
225                 230                 235                 240

Ala Pro Cys Val Val Thr Tyr Asn Ala Leu Leu Gln Val Phe Gly Lys
                245                 250                 255

Ala Gly Asn Tyr Thr Glu Ala Leu Arg Val Leu Gly Glu Met Glu Gln
            260                 265                 270

Asn Gly Cys Gln Pro Asp Ala Val Thr Tyr Asn Glu Leu Ala Gly Thr
        275                 280                 285

Tyr Ala Arg Ala Gly Phe Phe Glu Glu Ala Ala Arg
    290                 295                 300

<210> SEQ ID NO 45
<211> LENGTH: 2252
<212> TYPE: DNA
<213> ORGANISM: Artificial Sequence
<220> FEATURE:
<223> OTHER INFORMATION: Synthetic Polynucleotide

<400> SEQUENCE: 45
atgctcccct tggacagtct cctgctgcat ctcaccgccc cgcccccgc cccagcccct     60 gctccaagaa ggtctcatca aacgccgacc cccctcaca gcttcctgtc ccctgatgct    120

```
caggtgttgg tactcgcaat cagttctcac cctctgccta ccctggctgc tttcctcgct    180
agcaggcggg atgagttgct gagggccgat atcacctctc tccttaaggc acttgagctg    240
tctgggcact gggaatgggc attggccctg ctgcgatggg caggtaagga gggagctgcc    300
gatgctagcg ctttggagat ggtcgtaaga gcactcggta gagaaggcca gcatgacgca    360
gtctgtgctc tgctggacga aactccattg cctccaggca gcagactgga cgtacgggcc    420
tacaccaccg tgcttcacgc cctctcaaga gccggtaggt acgagagagc tctcgagctg    480
ttcgctgaac tcagaagaca gggcgtggcc ccaaccttgg taacttataa cgtggtactg    540
gacgtctacg gccgaatggg gagaagttgg ccgcgcatcg tcgcattgct cgacgaaatg    600
cgggccgcag gcgtcgagcc agatgggttt accgcaagca cggtgatcgc tgcttgctgc    660
cgggatggtt tggtgatga gccgtggcc ttctttgagg acttgaaggc caggggtcac    720
gcaccttgtg tcgtaaccta taacgcactg ttgcaggtgt tcggcaaggc tgggaattat    780
actgaggccc tgagagttct tggcgaaatg gagcagaacg ggtgccagcc agatgctgtg    840
acatataatg agctggccgg aacctacgca cgcgccggct tctttgagga ggccgccgg    900 tgtctggaca cgatggccag taagggcctg cttcctaacg cattcacata caataccgtg    960
atgacagcat atgaaatgt gggaaggtc gacgaagctc tcgcccttt cgatcagatg    1020 aaaaagactg gcttcgttcc caacgtgaac acgtacaacc tggtcctggg gatgctggga    1080
aagaaatcaa gattcacggt aatgttgaa atgttgggcg aaatgagcag gtcaggatgt    1140 accctaaca gggttacttg gaatactatg ctcgctgtgt gtggaaagcg agggatggaa    1200
gattacgtga cacgggttct ggagggcatg cggagttgcg tgtcgagct gtcccgagac    1260 acatacaaca ccctcatcgc tgcttatggg aggtgcggta gccggacaaa tgcttttaag    1320
atgtataacg aaatgacgtc cgcagggttc actccctgca tcactacata taacgctctg    1380
ctgaatgtgc tctctcggca aggagactgg tccactgctc agtcaatcgt ttcaaagatg    1440
cggactaagg gctttaagcc caacgagcaa tcttactcac tcctcctgca gtgttacgca    1500
aaggggggca atgtggcagg aattgcagcc atcgaaaacg aagtttacgg tccggcgct    1560 gttttcccat cttgggtgat cctgaggact cttgtaatcg ctaatttcaa atgtcgccgc    1620
ttggacggca tggaaactgc tttccaggag gtaaaggcca gggggtataa tcctgatttg    1680
gtgatattca actcaatgct ttccatctac gctaagaatg gtatgtatag caaagcaact    1740
gaggtcttcg actcaattaa gaggtcaggt ctgtccccag accttataac ttacaattcc    1800
ttgatggata tgtatgccaa gtgtagcgag tcctgggaag ctgaaaagat tcttaatcag    1860
ctgaaatgtt cccagactat gaagcccgat gttgttagct ataatacagt tatcaacgga    1920
ttctgcaaac agggccttgt gaagaagcc cagagagtgc tgtccgaaat ggtcgccgac    1980
ggcatggctc cttgcgctgt gacctaccat acattggtcg gcggctattc ctctctcgag    2040
atgttctccg aggccaggga ggtcatcggc tacatggtgc aacatggact gaaacctatg    2100
gaactgacct ataggagggt ggtggaatca tactgcagag ccaagcgatt cgaggaagct    2160
cggggtttcc tgtccgaagt gtctgagact gatctggact tcgacaaaaa agctttggaa    2220
gcatacatcg aggacgctca atttgggcgc ta                                  2252
```

<210> SEQ ID NO 46
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 46
attgtatcct taaccatttc ttttattgta tccttaacca tttctttt        47

<210> SEQ ID NO 47
<211> LENGTH: 130
<212> TYPE: PRT
<213> ORGANISM: Artificial Sequence
<220> FEATURE:
<223> OTHER INFORMATION: Synthetic Polypeptide

<400> SEQUENCE: 47

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Lys Arg Lys Tyr Thr Ile Lys Val Glu
    50                  55                  60

Val Pro Lys Val Ala Thr Gln Thr Val Gly Gly Glu Glu Leu Pro Val
65                  70                  75                  80

Ala Gly Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Ile Tyr
    130

<210> SEQ ID NO 48
<211> LENGTH: 390
<212> TYPE: DNA
<213> ORGANISM: Artificial Sequence
<220> FEATURE:
<223> OTHER INFORMATION: Synthetic Polynucleotide

<400> SEQUENCE: 48
atggcttcta actttactca gttcgttctc gtcgacaatg gcggaactgg cgacgtgact        60
gtcgccccaa gcaacttcgc taacggggtc gctgaatgga tcagctctaa ctcgcgttca       120
caggcttaca agtaaacctg tagcgttcgt cagagctctg cgcagaagcg caaatacacc       180
atcaaagtcg aggtgcctaa agtggcaacc cagactgttg gtggtgagga gcttcctgta       240
gccggttggc gttcgtactt aaatatggaa ctaaccattc caattttcgc cacgaattcc       300
gactgcgagc ttattgttaa ggcaatgcaa ggcctcctaa aagatggaaa cccgattccc       360
tcggccatcg cagcaaactc cggcatctac                                        390

<210> SEQ ID NO 49
<211> LENGTH: 79
<212> TYPE: DNA
<213> ORGANISM: Artificial Sequence
<220> FEATURE:
<223> OTHER INFORMATION: Synthetic Polynucleotide

<400> SEQUENCE: 49
acatgaggat cacccatgtc tgcaggtcga ctctagaaaa catgaggatc acccatgtcc        60
tgcaggtcga ctctagaaa                                                    79

<210> SEQ ID NO 50
<211> LENGTH: 119
<212> TYPE: PRT
<213> ORGANISM: Artificial Sequence
<220> FEATURE:
<223> OTHER INFORMATION: Synthetic Polypeptide

<400> SEQUENCE: 50

```
Met Tyr Val Arg Phe Glu Val Pro Glu Asp Met Gln Asn Glu Ala Leu
1               5                   10                  15

Ser Leu Leu Glu Lys Val Arg Glu Ser Gly Lys Val Lys Lys Gly Thr
            20                  25                  30

Asn Glu Thr Thr Lys Ala Val Glu Arg Gly Leu Ala Lys Leu Val Tyr
        35                  40                  45

Ile Ala Glu Asp Val Asp Pro Pro Glu Ile Val Ala His Leu Pro Leu
    50                  55                  60

Leu Cys Glu Glu Lys Asn Val Pro Tyr Ile Tyr Val Lys Ser Lys Asn
65                  70                  75                  80

Asp Leu Gly Arg Ala Val Gly Ile Glu Val Pro Cys Ala Ser Ala Ala
                85                  90                  95

Ile Ile Asn Glu Gly Glu Leu Arg Lys Glu Leu Gly Ser Leu Val Glu
            100                 105                 110

Lys Ile Lys Gly Leu Gln Lys
        115
```

<210> SEQ ID NO 51
<211> LENGTH: 357
<212> TYPE: DNA
<213> ORGANISM: Artificial Sequence
<220> FEATURE:
<223> OTHER INFORMATION: Synthetic Polynucleotide

<400> SEQUENCE: 51

```
atgtacgtga gatttgaggt tcctgaggac atgcagaacg aagctctgag tctgctggag      60
aaggttaggg agagcggtaa ggtaaagaaa ggtaccaacg agacgacaaa ggctgtggag     120
aggggactgg caaagctcgt ttacatcgca gaggatgttg acccgcctga gatcgttgct     180
catctgcccc tcctctgcga ggagaagaat gtgccgtaca tttacgttaa aagcaagaac     240
gaccttggaa gggctgtggg cattgaggtg ccatgcgctt cggcagcgat aatcaacgag     300
ggagagctga gaaggagct tggaagcctt gtggagaaga ttaaaggcct tcagaag        357
```

<210> SEQ ID NO 52
<211> LENGTH: 66
<212> TYPE: DNA
<213> ORGANISM: Artificial Sequence
<220> FEATURE:
<223> OTHER INFORMATION: Synthetic Polynucleotide

<400> SEQUENCE: 52

```
gggcgtgatc cgaaaggtga cccggatctg ggcgtgatc cgaaaggtga cccggatcca      60
ccggtc                                                                66
```

<210> SEQ ID NO 53
<211> LENGTH: 286
<212> TYPE: PRT
<213> ORGANISM: Artificial Sequence
<220> FEATURE:
<223> OTHER INFORMATION: Synthetic Polypeptide

<400> SEQUENCE: 53

| | | | | | | | | | | | | | | |
|---|---|---|---|---|---|---|---|---|---|---|---|---|---|---|
|Met|Pro|Ala|Ala|Thr|Val|Asp|His|Ser|Gln|Arg|Ile|Cys|Glu|Val|Trp|
|1| | | |5| | | | |10| | | | |15| |

Met Pro Ala Ala Thr Val Asp His Ser Gln Arg Ile Cys Glu Val Trp
1               5                   10                  15

Ala Cys Asn Leu Asp Glu Glu Met Lys Lys Ile Arg Gln Val Ile Arg
            20                  25                  30

Lys Tyr Asn Tyr Val Ala Met Asp Thr Glu Phe Pro Gly Val Val Ala
            35                  40                  45

Arg Pro Ile Gly Glu Phe Arg Ser Asn Ala Asp Tyr Gln Tyr Gln Leu
        50                  55                  60

Leu Arg Cys Asn Val Asp Leu Leu Lys Ile Ile Gln Leu Gly Leu Thr
65                  70                  75                  80

Phe Met Asn Glu Gln Gly Glu Tyr Pro Pro Gly Thr Ser Thr Trp Gln
                85                  90                  95

Phe Asn Phe Lys Phe Asn Leu Thr Glu Asp Met Tyr Ala Gln Asp Ser
            100                 105                 110

Ile Glu Leu Leu Thr Thr Ser Gly Ile Gln Phe Lys Lys His Glu Glu
            115                 120                 125

Glu Gly Ile Glu Thr Gln Tyr Phe Ala Glu Leu Leu Met Thr Ser Gly
        130                 135                 140

Val Val Leu Cys Glu Gly Val Lys Trp Leu Ser Phe His Ser Gly Tyr
145                 150                 155                 160

Asp Phe Gly Tyr Leu Ile Lys Ile Leu Thr Asn Ser Asn Leu Pro Glu
            165                 170                 175

Glu Glu Leu Asp Phe Phe Glu Ile Leu Arg Leu Phe Phe Pro Val Ile
            180                 185                 190

Tyr Asp Val Lys Tyr Leu Met Lys Ser Cys Lys Asn Leu Lys Gly Gly
        195                 200                 205

Leu Gln Glu Val Ala Glu Gln Leu Glu Leu Glu Arg Ile Gly Pro Gln
        210                 215                 220

His Gln Ala Gly Ser Asp Ser Leu Leu Thr Gly Met Ala Phe Lys
225                 230                 235                 240

Met Arg Glu Met Phe Phe Glu Asp His Ile Asp Asp Ala Lys Tyr Cys
            245                 250                 255

Gly His Leu Tyr Gly Leu Gly Ser Gly Ser Ser Tyr Val Gln Asn Gly
            260                 265                 270

Thr Gly Asn Ala Tyr Glu Glu Glu Ala Asn Lys Gln Ser Val
        275                 280                 285

<210> SEQ ID NO 54
<211> LENGTH: 858
<212> TYPE: DNA
<213> ORGANISM: Artificial Sequence
<220> FEATURE:
<223> OTHER INFORMATION: Synthetic Polynucleotide

<400> SEQUENCE: 54

```
atgccagcgg caactgtaga tcatagccaa agaatttgtg aagtttgggc ttgcaacttg      60
gatgaagaga tgaagaaaat tcgtcaagtt atccgaaaat ataattacgt tgctatggac     120
accgagtttc caggtgtggt tgcaagaccc attggagaat caggagcaa tgctgactat      180 caataccaac tattgcggtg taatgtagac ttgttaaaga taattcagct aggactgaca     240
tttatgaatg agcaaggaga atacccctcca ggaacttcaa cttggcagtt taattttaaa   300
tttaatttga cggaggacat gtatgccag gactctatag agctactaac aacatctggt      360
atccagttta aaaaacatga ggaggaagga attgaaaccc agtactttgc agaacttctt     420
```

```
atgacttctg gagtggtcct ctgtgaaggg gtcaaatggt tgtcatttca tagcggttac    480
gactttggct acttaatcaa aatcctaacc aactctaact tgcctgaaga agaacttgac    540
ttctttgaga tccttcgatt gttttttcct gtcatttatg atgtgaagta cctcatgaag    600
agctgcaaaa atctcaaagg tggattacag gaggtggcag aacagttaga gctggaacgg    660
ataggaccac aacatcaggc aggatctgat tcattgctca caggaatggc cttttttcaaa    720 atgagagaaa tgttctttga agatcatatt gatgatgcca atattgtgg tcatttgtat    780 ggccttggtt ctggttcatc ctatgtacag aatggcacag gaatgcata tgaagaggaa    840 gccaacaagc agtcagtt                                                  858
```

```
<210> SEQ ID NO 55
<211> LENGTH: 483
<212> TYPE: PRT
<213> ORGANISM: Artificial Sequence
<220> FEATURE:
<223> OTHER INFORMATION: Synthetic Polypeptide

<400> SEQUENCE: 55

Met Ser Thr Ala Arg Thr Glu Asn Pro Val Ile Met Gly Leu Ser Ser
1               5                   10                  15

Gln Asn Gly Gln Leu Arg Gly Pro Val Lys Ala Ser Ala Gly Pro Gly
            20                  25                  30

Gly Gly Gly Thr Gln Pro Gln Pro Gln Leu Asn Gln Leu Lys Asn Thr
        35                  40                  45

Ser Thr Ile Asn Asn Gly Thr Pro Gln Gln Ala Gln Ser Met Ala Ala
    50                  55                  60

Thr Ile Lys Pro Gly Asp Asp Trp Lys Lys Thr Leu Lys Leu Pro Pro
65                  70                  75                  80

Lys Asp Leu Arg Ile Lys Thr Ser Asp Val Thr Ser Thr Lys Gly Asn
                85                  90                  95

Glu Phe Glu Asp Tyr Cys Leu Lys Arg Glu Leu Leu Met Gly Ile Phe
            100                 105                 110

Glu Met Gly Trp Glu Lys Pro Ser Pro Ile Gln Glu Glu Ser Ile Pro
        115                 120                 125

Ile Ala Leu Ser Gly Arg Asp Ile Leu Ala Arg Ala Lys Asn Gly Thr
    130                 135                 140

Gly Lys Ser Gly Ala Tyr Leu Ile Pro Leu Leu Glu Arg Leu Asp Leu
145                 150                 155                 160

Lys Lys Asp Asn Ile Gln Ala Met Val Ile Val Pro Thr Arg Glu Leu
                165                 170                 175

Ala Leu Gln Val Ser Gln Ile Cys Ile Gln Val Ser Lys His Met Gly
            180                 185                 190

Gly Ala Lys Val Met Ala Thr Thr Gly Gly Thr Asn Leu Arg Asp Asp
        195                 200                 205

Ile Met Arg Leu Asp Asp Thr Val His Val Val Ile Ala Thr Pro Gly
    210                 215                 220

Arg Ile Leu Asp Leu Ile Lys Lys Gly Val Ala Lys Val Asp His Val
225                 230                 235                 240

Gln Met Ile Val Leu Asp Glu Ala Asp Lys Leu Leu Ser Gln Asp Phe
                245                 250                 255

Val Gln Ile Met Glu Asp Ile Ile Leu Thr Leu Pro Lys Asn Arg Gln
            260                 265                 270

Ile Leu Leu Tyr Ser Ala Thr Phe Pro Leu Ser Val Gln Lys Phe Met
        275                 280                 285
```

Asn Ser His Leu Gln Lys Pro Tyr Glu Ile Asn Leu Met Glu Glu Leu
290                 295                 300

Thr Leu Lys Gly Val Thr Gln Tyr Tyr Ala Tyr Val Thr Glu Arg Gln
305                 310                 315                 320

Lys Val His Cys Leu Asn Thr Leu Phe Ser Arg Leu Gln Ile Asn Gln
                325                 330                 335

Ser Ile Ile Phe Cys Asn Ser Ser Gln Arg Val Glu Leu Leu Ala Lys
            340                 345                 350

Lys Ile Ser Gln Leu Gly Tyr Ser Cys Phe Tyr Ile His Ala Lys Met
        355                 360                 365

Arg Gln Glu His Arg Asn Arg Val Phe His Asp Phe Arg Asn Gly Leu
370                 375                 380

Cys Arg Asn Leu Val Cys Thr Asp Leu Phe Thr Arg Gly Ile Asp Ile
385                 390                 395                 400

Gln Ala Val Asn Val Val Ile Asn Phe Asp Phe Pro Lys Leu Ala Glu
                405                 410                 415

Thr Tyr Leu His Arg Ile Gly Arg Ser Gly Arg Phe Gly His Leu Gly
            420                 425                 430

Leu Ala Ile Asn Leu Ile Thr Tyr Asp Asp Arg Phe Asn Leu Lys Ser
        435                 440                 445

Ile Glu Glu Gln Leu Gly Thr Glu Ile Lys Pro Ile Pro Ser Asn Ile
450                 455                 460

Asp Lys Ser Leu Tyr Val Ala Glu Tyr His Ser Glu Pro Ala Glu Asp
465                 470                 475                 480

Glu Lys Pro

<210> SEQ ID NO 56
<211> LENGTH: 1449
<212> TYPE: DNA
<213> ORGANISM: Artificial Sequence
<220> FEATURE:
<223> OTHER INFORMATION: Synthetic Polynucleotide

<400> SEQUENCE: 56

```
atgagcacag ctcgcaccga gaacccggtg attatgggcc tgtccagcca gaacggacag    60
ctcagagggc ctgtaaaggc ttcagcaggc cccggcggag gcggcacaca accacaacca   120
cagcttaatc agcttaagaa tactagcact attaataacg gaacaccgca gcaggcccaa   180
agcatggctg ccacaattaa acccggagat gactggaaga gaccctgaa gctccctcca    240
aaagatctca ggattaaaac tagcgatgtt acttcaacaa agggaaatga gttcgaagac   300
tactgtctga agcgagagtt gctgatgggg attttcgaaa tgggctggga aagccctct    360
cctattcaag aagagagcat ccccatcgct ctgtccggga gggacatcct tgccagggct   420
aaaaatggga ccggaaaatc aggagcttac ttgatcccac tccttgaaag gcttgatctc   480
aagaaggaca acatccaagc tatggttatc gtgccaacta gagaactcgc cctccaggtc   540
agccagattt gcatccaggt gagtaagcac atgggcggag ctaaggtgat ggctacaact   600
ggagggacta acctgcgaga cgacataatg agacttgatg acacagtcca tgtggtcatc   660
gctacacctg gaggattct ggatctgatc aaaaaaggag tggcaaaggt ggatcatgtg   720
cagatgatag tcttggacga ggccgacaaa ctgctgagcc aagactttgt gcagatcatg   780
gaggatatca tcttgacact ccccaagaac cgacagattc tgctgtactc cgcaacattt   840
cctcttccg ttcagaaatt catgaactca catctccaga aacctatga gatcaatttg   900
atggaagaac tgacactgaa gggcgtgacc cagtattatg cctacgttac tgagaggcaa   960
```

```
aaggtccact gcctgaatac tctcttctcc aggctccaga tcaaccagtc tatcatcttt    1020
tgcaatagct cccagcgagt cgagctgctg gctaagaaga tctcacagct tggatattcc    1080
tgtttctaca tccatgctaa gatgagacaa gagcacagaa accgcgtctt tcatgatttc    1140
cggaacggac tctgtcgcaa cctggtttgc acagatcttt ttactagagg catcgatatc    1200
caagcagtga acgtggttat caacttcgac tttcccaaac tcgccgagac ttatcttcat    1260
agaattggcc gatccggtag gtttgggcac ctggggctcg ccatcaatct cattacgtat    1320
gatgataggt tcaacctcaa gtcaatagaa gagcagttgg ggaccgagat caaaccaatc    1380
ccgagcaata ttgacaaatc actctatgtg gccgaatacc attcagagcc tgccgaggat    1440
gagaagcct                                                            1449
```